US00RE49575E

(19) United States
(12) Reissued Patent
Platzek et al.

(10) Patent Number: US RE49,575 E
(45) Date of Reissued Patent: *Jul. 11, 2023

(54) METHOD FOR THE PREPARATION OF (4S)-4-(4-CYANO-2-METHOXYPHENYL)-5-ETHOXY-2,8-DIMETHYL-L,4-DIHYDRO-1-6-NAPHTHYRIDINE-3-CARBOX-AMIDE AND THE PURIFICATION THEREOF FOR USE AS AN ACTIVE PHARMACEUTICAL INGREDIENT

(71) Applicant: Bayer Pharma Aktiengesellschaft, Berlin (DE)

(72) Inventors: Johannes Platzek, Berlin (DE); Gunnar Garke, Solingen (DE); Alfons Grunenberg, Wuppertal (DE)

(73) Assignee: BAYER PHARMA AKTIENGESELLSCHAFT, Berlin (DE)

( * ) Notice: This patent is subject to a terminal disclaimer.

(21) Appl. No.: 17/002,115

(22) Filed: Aug. 25, 2020

Related U.S. Patent Documents

Reissue of:
(64) Patent No.: 10,059,707
Issued: Aug. 28, 2018
Appl. No.: 15/329,043
PCT Filed: Jul. 29, 2015
PCT No.: PCT/EP2015/067340
§ 371 (c)(1),
(2) Date: Jan. 25, 2017
PCT Pub. No.: WO2016/016287
PCT Pub. Date: Feb. 4, 2016

(30) Foreign Application Priority Data

Aug. 1, 2014 (EP) ..... 14179544

(51) Int. Cl.
*C07D 471/04* (2006.01)

(52) U.S. Cl.
CPC ..... *C07D 471/04* (2013.01); *C07B 2200/13* (2013.01)

(58) Field of Classification Search
CPC ..... C07D 471/04; C07B 2200/13; A61P 3/00; A61P 3/04; A61P 3/10; A61P 3/12; A61P 3/14; A61P 7/10; A61P 9/00; A61P 9/04; A61P 9/06; A61P 9/10; A61P 9/12; A61P 9/14; A61P 13/00; A61P 13/12; A61P 25/00; A61P 25/04; A61P 25/06; A61P 25/16; A61P 25/22; A61P 25/24; A61P 25/28; A61P 29/00; A61P 35/00; A61P 43/00; A61K 31/4375
See application file for complete search history.

(56) References Cited

U.S. PATENT DOCUMENTS 6,693,102 B2 2/2004 Stasch et al.
6,743,798 B1 6/2004 Straub et al.
6,833,364 B1 12/2004 Straub et al.
6,864,287 B1 3/2005 Alonso-Alija et al.
7,087,644 B1 8/2006 Alonso-Alija et al.
7,173,037 B2 2/2007 Alonso-Alija et al.
7,674,825 B2 3/2010 Alonso-Alija et al.
7,705,043 B2 4/2010 Alonso-Alija et al.
8,436,180 B2 5/2013 BÄrfacker et al.
10,399,977 B2 * 9/2019 Platzek ..... A61P 3/04
2004/0176446 A1 9/2004 Alonso-Alija et al.
2008/0312209 A1 12/2008 MacDonald et al.
2014/0100243 A1 * 4/2014 Barfacker ..... C07D 471/04 514/300

FOREIGN PATENT DOCUMENTS

WO 00/06568 A1 2/2000
WO 00/6569 A1 2/2000
WO 01/19355 A2 3/2001
WO 01/19776 A2 3/2001
WO 01/19778 A1 3/2001
WO 01/19780 A2 3/2001
(Continued)

OTHER PUBLICATIONS

Abe et al., "Large Scale Synthesis of N-benzyl-4-formylpiperidine through Partial Reduction of Esters using Aluminum Hydride Reagents Modified with Pyrrolidine," Tetrahedron, (2001), vol. 57, No. 14, pp. 2701-2710.

(Continued)

*Primary Examiner* — Alan D Diamond
(74) *Attorney, Agent, or Firm* — Quarles & Brady LLP

(57) ABSTRACT

The present invention relates to a novel and improved process for preparing (4S)-4-(4-cyano-2-methoxyphenyl)-5-ethoxy-2,8-dimethyl-1,4-dihydro-1,6-naphthyridine-3-carboxamide of the formula (I)

(I)

and also the preparation and use of the crystalline polymorph I of (4S)-4-(4-cyano-2-methoxyphenyl)-5-ethoxy-2,8-dimethyl-1,4-dihydro-1,6-naphthyridine-3-carboxamide of the formula (I).

24 Claims, 10 Drawing Sheets

(56) References Cited

FOREIGN PATENT DOCUMENTS

| | | | | |
|---|---|---|---|---|
| WO | WO 02/42301 | A1 | 5/2002 | |
| WO | 02/42301 | A1 | 9/2002 | |
| WO | 02/070462 | A1 | 9/2002 | |
| WO | 02/070510 | A2 | 9/2002 | |
| WO | 03/095451 | A1 | 11/2003 | |
| WO | 2008104306 | A2 | 4/2008 | |
| WO | 2008/104306 | A2 | 9/2008 | |
| WO | WO-2008104306 | A2 * | 9/2008 | ..... C07D 471/04 |

OTHER PUBLICATIONS

Chidambaram, "A Robust Palladium-Catalyzed Cyanation Procedure: Beneficial Effect of Zinc Acetate," Tetrahedron Letters, (2004), vol. 45, No. 7, p. 1441-1444.

Görlitzer et al., "Untersuchungen zum Reaktionsmechanismus der Bildung einer 9-Hydroxy-β-carbolin-4-Darbonsaure aus dem Nifedipin-analogen Biscyanoethylester = Investigations of the reaction mechanism concerning the formation of a 9-hydroxy-|3-carboline-4-carboxylic acid from the nifedipine analogous biscyanoethyl ester" Pharmazie, (2000), vol. 55, No. 10, pp. 747-750.

Grimster et al., "Aromatic Sulfonyl Fluorides Covalently Kinetically Stabilize Transthyretin to Prevent Amyloidogenesis while Affording a Fluorescent Conjugate," Journal of the American Chemical Society, (2013), vol. 135, No. 15, pp. 5656-5668.

Hung et al., "A General Route to 5- and 6-Substituted 4-Amino-2-oxo-1,2-Dihydropyridines," Synthesis, (1984), vol. 1984, No. 9, pp. 765-766.

Patrick et al., "Synthesis and in Vitro Antiprotozoal Activities of Dicationic 3,5-Diphenylisoxazoles," Journal of Medicinal Chemistry, (2007), vol. 50, No. 10, pp. 2468-2485.

Schareina et al., "A new Palladium Catalyst System for the Cyanation of Aryl Chlorides with K4[Fe(CN)6]," Tetrahedron Letters, (2007), vol. 48, No. 7, pp. 1087-1090.

Sundermeier et al., "Ein praktikables Verfahren zur Palladiumkatalysierten Cyanierung von Arylhalogeniden," Angewandte Chemie, (2003), vol. 115, No. 14, pp. 1700-1703.

Zanon et al., "Copper-Catalyzed Domino Halide Exchange-Cyanation of Aryl Bromides," Journal of the American Chemical Society, (2003), vol. 125, No. 10, pp. 2890-2891.

Stahly, G.P., "Diversity in Single- and Multiple-Component Crystals. The Search for and Prevalence of Polymorphs and Cocrystals," Crystal Growth & Design 2007, vol. 7, No. 6, 1007-1026.

Bärfacker et al., "Discovery of BAY 94-8862: A Nonsteroidal Antagonist of the Mineralocorticoid Receptor for the Treatment of Cardiorenal Diseases," ChemMedChem, (2012), vol. 7, No. 8, pp. 1385-1403.

Byrn et al., "Pharmaceutical Solids: A Strategic Approach to Regulatory Considerations," Pharmaceutical Research, (1995), vol. 12, No. 7, pp. 945-954.

Caira, "Crystalline Polymorphism of Organic Compounds," Topics in Current Chemistry, (1999), vol. 198, pp. 163-208.

Chang et al., "Highly Efficient Triarylene Conjugated Dyes for Sensitized Solar Cells," Journal of Materials Chemistry, (2011), vol. 21, pp. 9523-9531.

Glennon et al., "Binding of Phenylalylamine Derivatives at 5-HT1C and 5-HT2 Serotonin Receptors: Evidence for a Lack of Selectivity," Journal of Medicinal Chemistry, (1992), vol. 35, No. 4, pp. 734-740.

Görlitzer et al., "Untersuchungen zum Reaktionsmechanismus der Bildung einer 9-Hydroxy-α-carbolin-4-carbonsäure aus dem Nifedipin-analogen Biscyanoethylester—Investigations of the reaction mechanism concerning the formation of a 9-hyroxy-β-carboline-4-carboylic acid from the nifedipine analogous biscyanoethyl ester"Pharmazie, (2000), vol. 55, No. 10, pp. 747-750.

Hagiya et al., "A Facile and Selective Synthetic Method for the Preparation of Aromatic Dialdehydes from Diesters via the Amine-Modified SMEAH Reduction System," Synthesis, (2003), No. 6, pp. 823-828.

Martin et al., "Open Air Palladium Catalyzed Cyanation-the use of PMHS to Protect from Oxygen," Tetrahedron Letters, (2007), vol. 48, No. 14, pp. 2555-2557.

Ogura et al., "Total Synthesis of Acerogenins E, G and K. and Centrolobol," Tetrahedron, (2013), vol. 69, No. 13, pp. 2807-2815.

Schareina et al., "Improving Palladium-Catalyzed Cyanation of Aryl Halides: Development of a State-of-the-art Methodolody using Potassium Hexacyanoferrate(II) as Cyanating Agent," Journal of Organometallic Chemistry,(2004), vol. 689, No. 24, pp. 4576-4583.

Tromelin et al., "Synthèse et étude biologique préliminaire de dérivès dichlorèthylaminés sur l'homocycle de nitro-2 benzofurannes," European Journal of Medicinal Chemistry,(1986), vol. 21, No. 5, pp. 397-402.

Tschaen et al., "An Improved Procedure for Aromatic Cyanation," Synthetic Communications, (1994), vol. 24, No. 6, pp. 887-890.

Yamamoto et al., "Structure—Activity Relationship Study of 1,4-Dihydropyridine Derivatives Blocking N-type Calcium Channels," Bioorganic & Medicinal Chemistry Letters, (2006), vol. 16, No. 4, pp. 798-802.

* cited by examiner

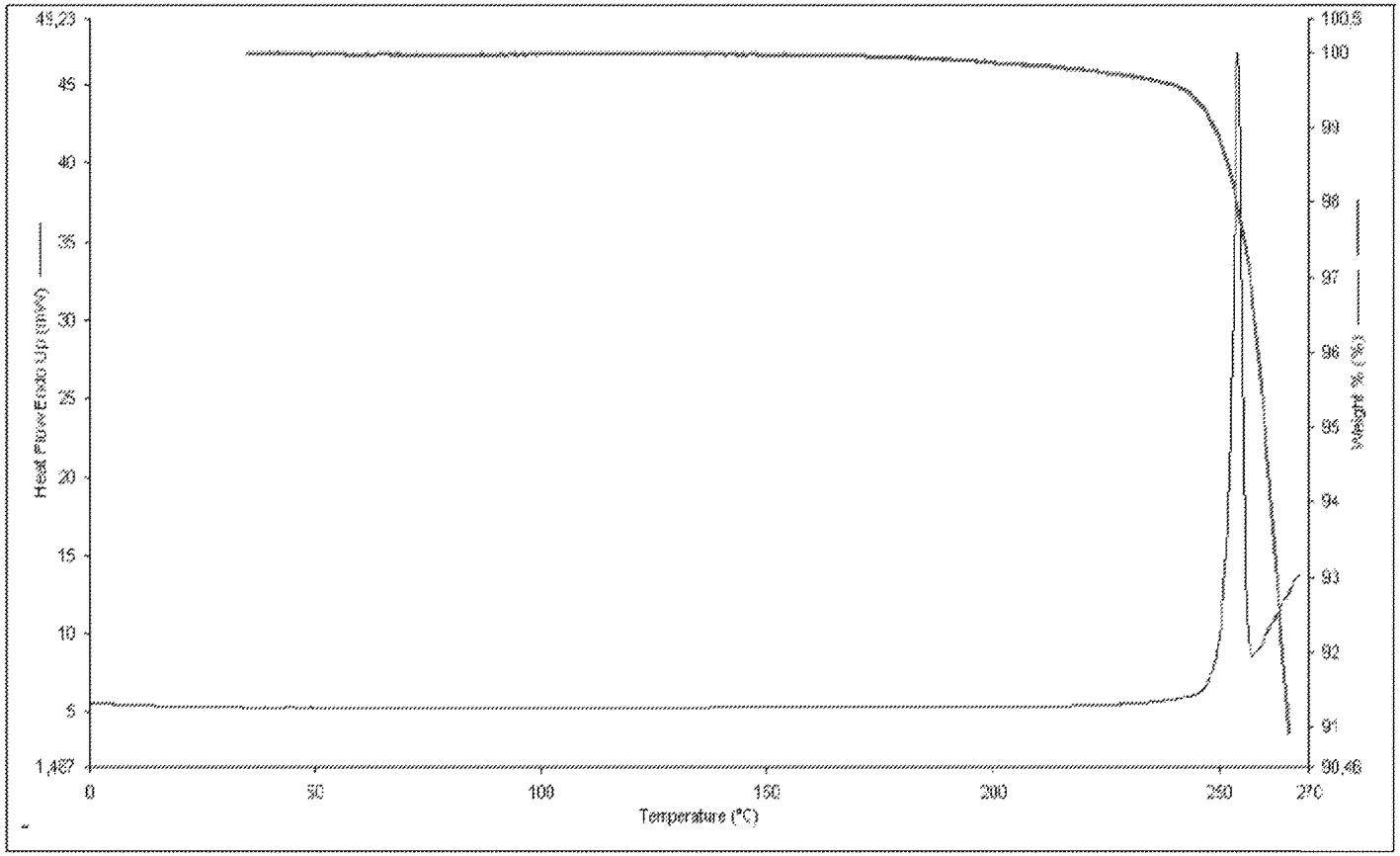
Figure 1: DSC (20Kmin$^{-1}$) and TGA of compound of the formula (I) in crystalline form of polymorph I

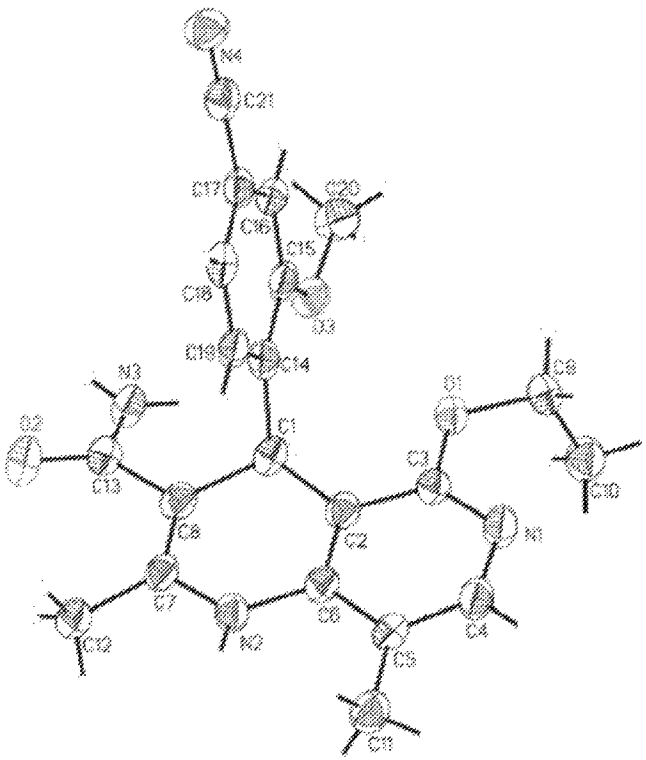
Figure 2: X-ray of a single crystal of polymorph I of (4S)- 4-(4-cyano-2-methoxyphenyl)-5-ethoxy-2,8-dimethyl-1,4-dihydro-1,6-naphthyridine-3-carboxamide (I)

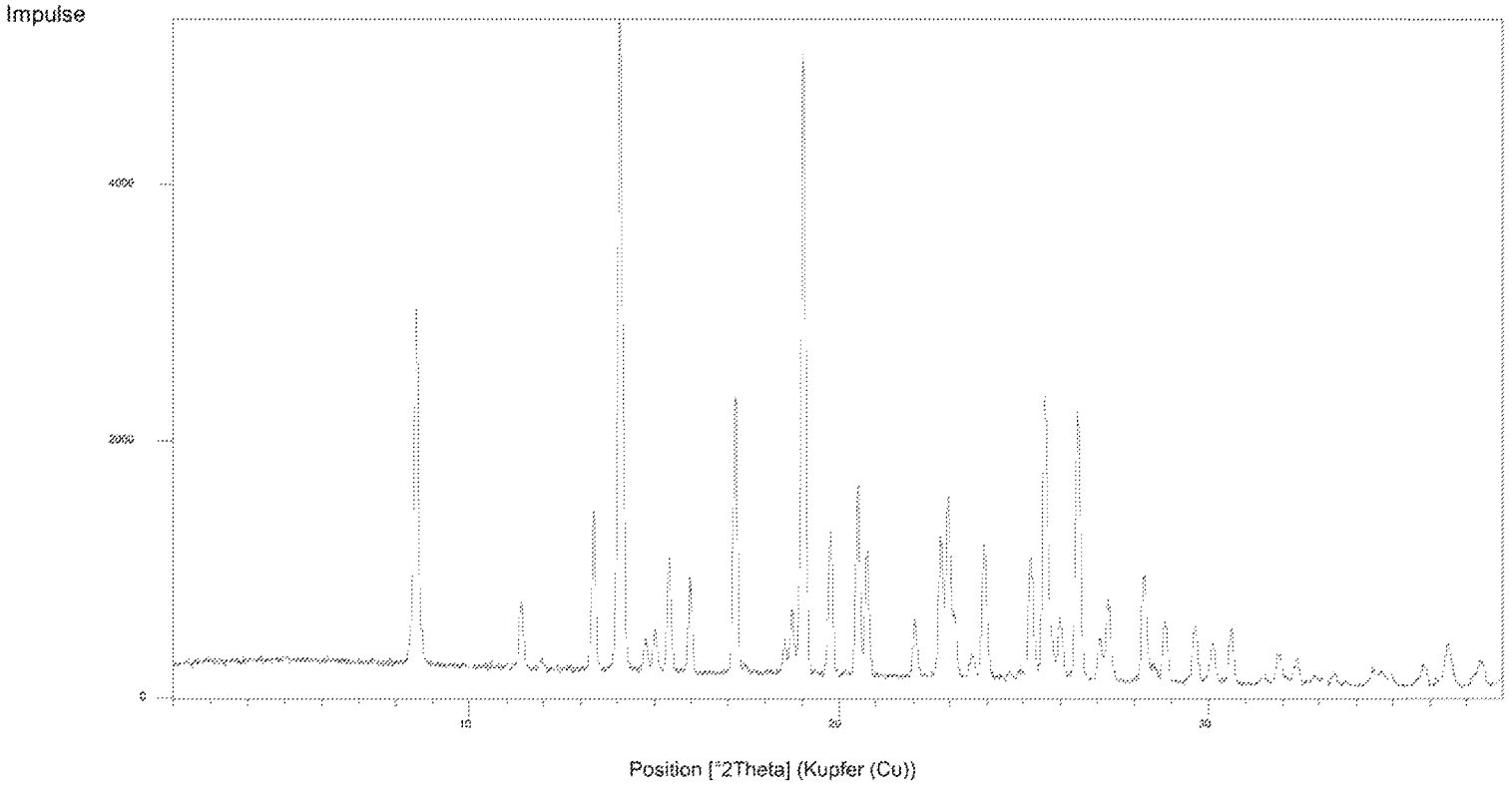
Figure 3: X-ray diffractogram of the compound of the formula (I) in crystalline form of polymorph I

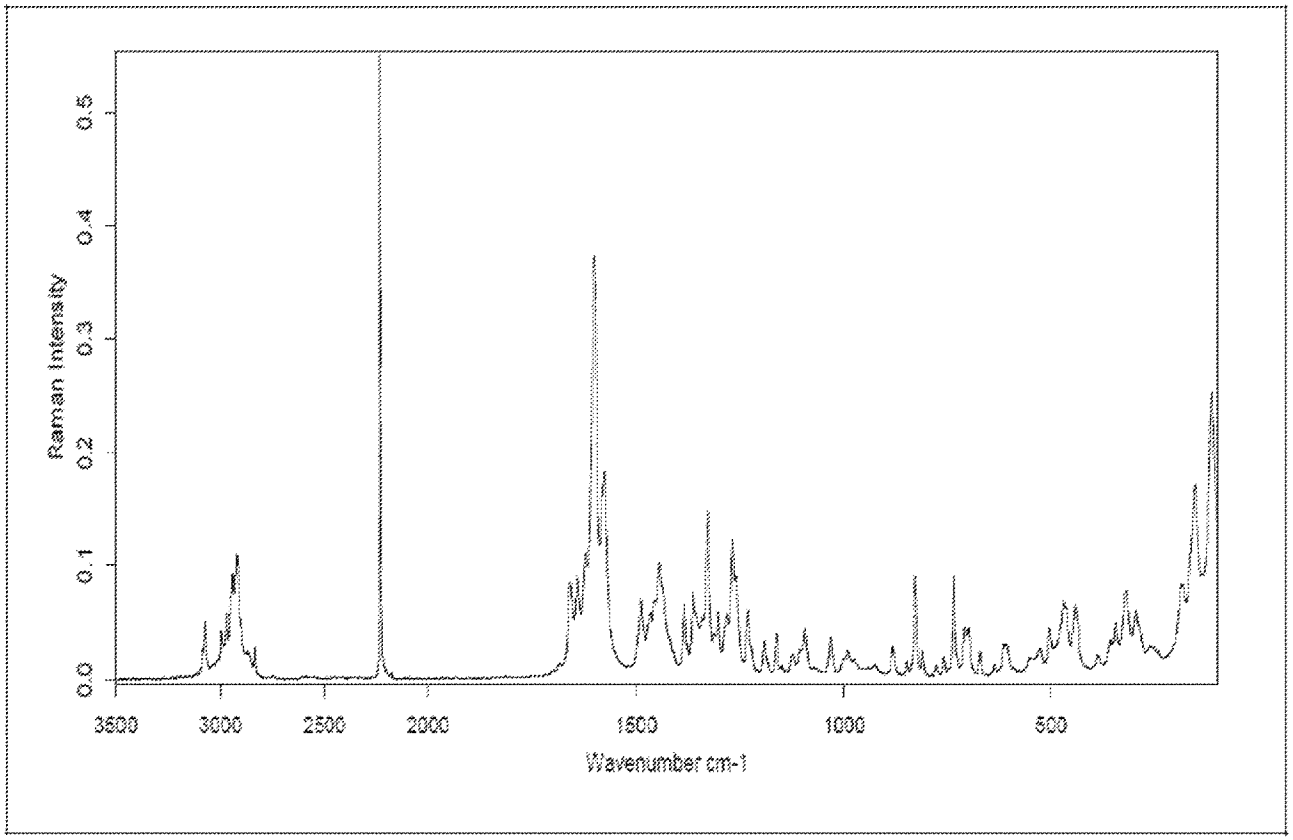
Figure 4: Raman Spectrum of compound of the formula (I) in crystalline form of polymorph I

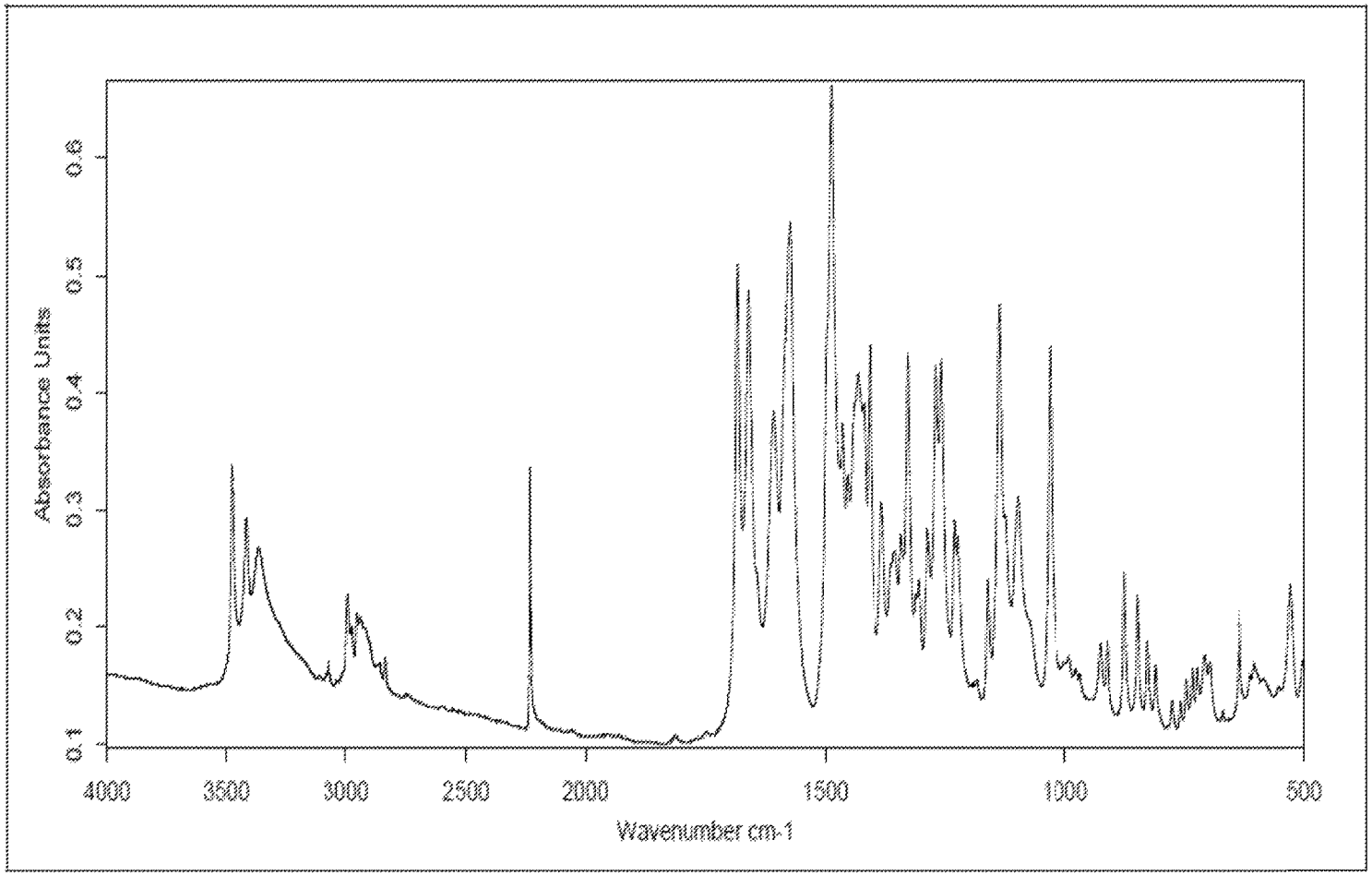
Figure 5: FT-Infrared (IR) spectrum (KBr) of compound of the formula (I) in cyrstalline form of polymorph I

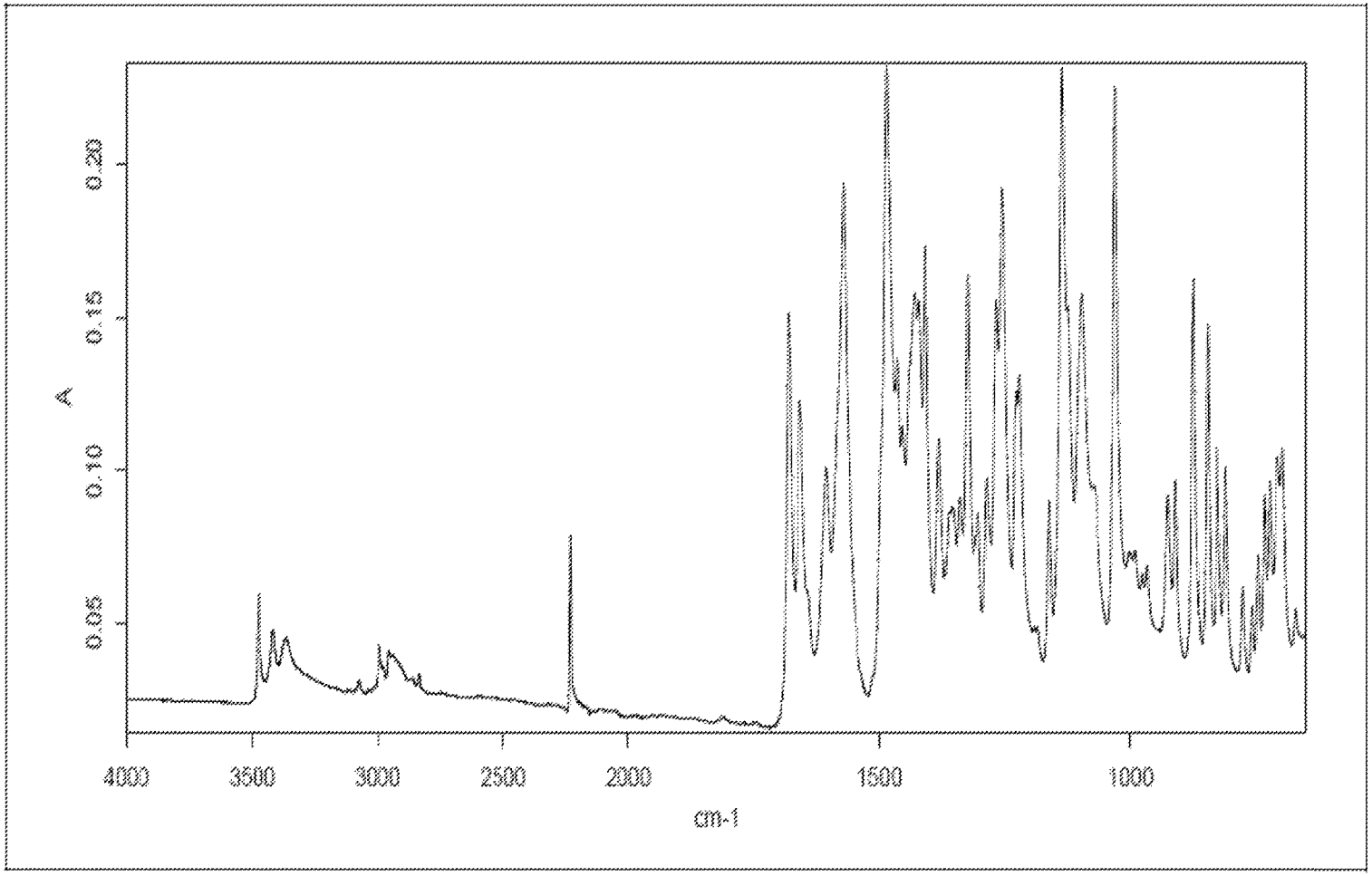
Figure 6: FT-Infrared (IR) spectrum (ATR) of compound of the formula (I) in cyrstalline form of polymorph I

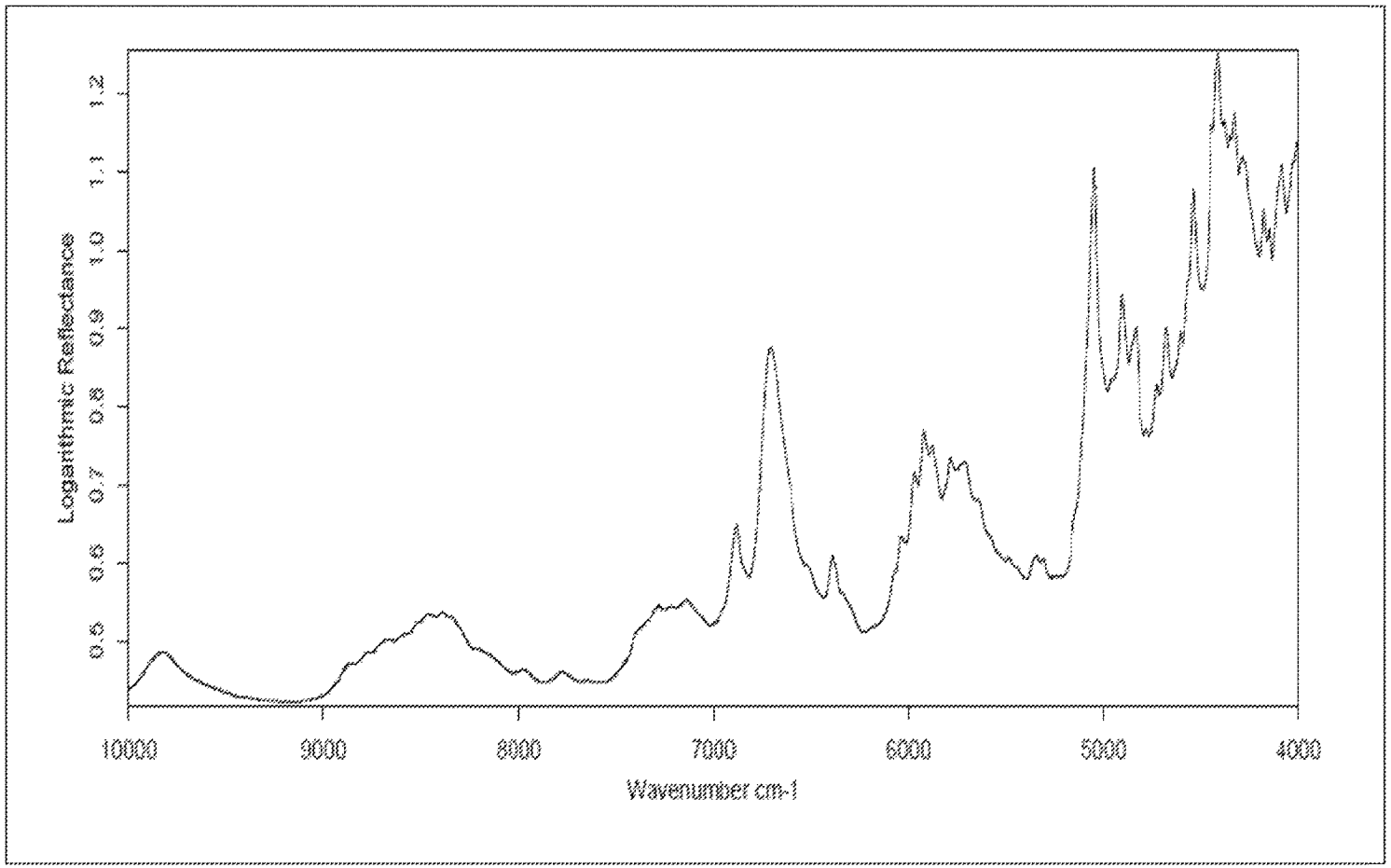
Figure 7: FT-Near-infrared (NIR) spectrum of compound of the formula (I) in cyrstalline form of polymorph I

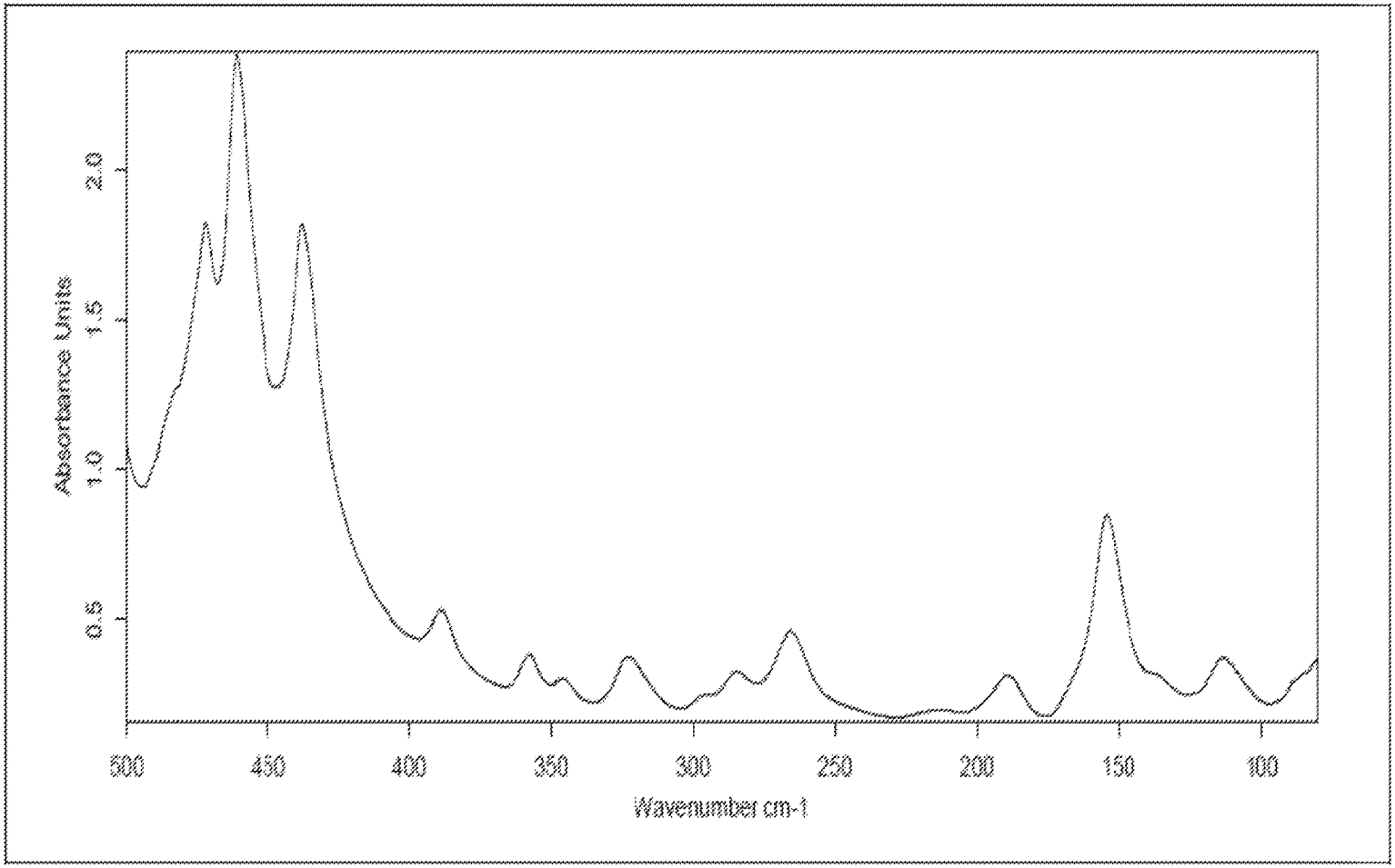
Figure 8: FT-Far-infrared (FIR) spectrum of compound of the formula (I) in cyrstalline form of polymorph I

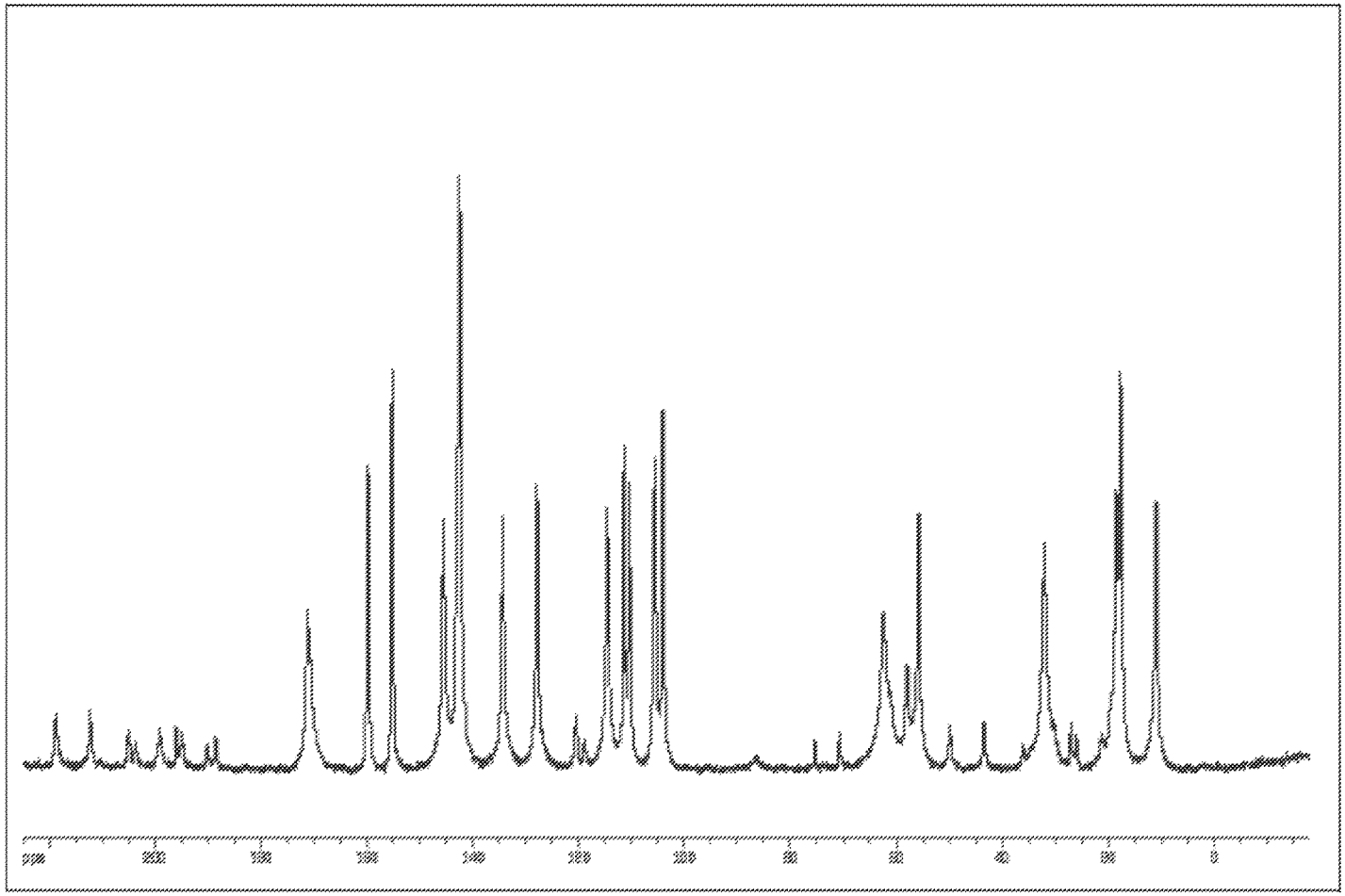
Figure 9: Solidstate $^{13}C$-NMR spectrum of compound of the formula (I) in cyrstalline form of polymorph I

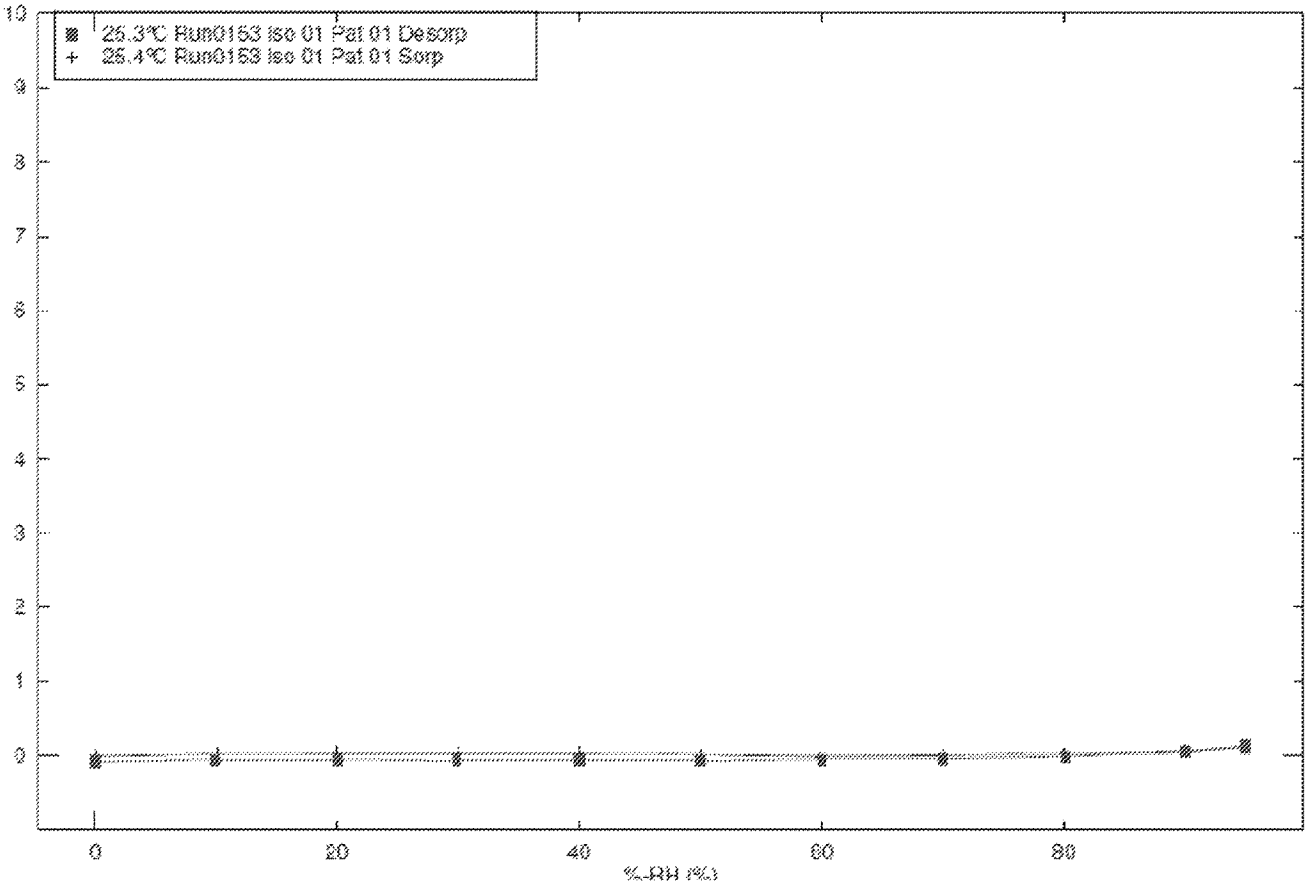
Figure 10: Stability of compound of the formula (I) in crystalline form of polymorph I in air humidity (x-axis % relative humidity/y-axis weight change in %).

METHOD FOR THE PREPARATION OF (4S)-4-(4-CYANO-2-METHOXYPHENYL)-5-ETHOXY-2,8-DIMETHYL-L,4-DIHYDRO-1-6-NAPHTHYRIDINE-3-CARBOX-AMIDE AND THE PURIFICATION THEREOF FOR USE AS AN ACTIVE PHARMACEUTICAL INGREDIENT

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

The present invention relates to a novel and improved process for preparing (4S)-4-(4-cyano-2-methoxyphenyl)-5-ethoxy-2,8-dimethyl-1,4-dihydro-1,6-naphthyridine-3-carboxamide of the formula (I)

(I)

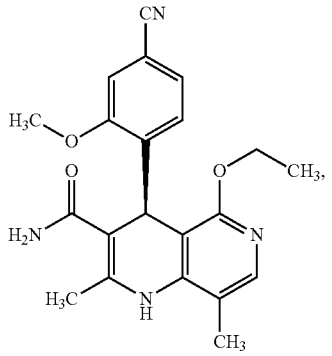

and also the preparation and use of the crystalline polymorph I of (4S)-4-(4-cyano-2-methoxyphenyl)-5-ethoxy-2,8-dimethyl-1,4-dihydro-1,6-naphthyridine-3-carboxamide of the formula (I).

The compound of the formula (I) acts as a non-steriodal antagonist of the mineralocorticoid receptor and may be used as an agent for prophylaxis and/or treatment of cardiovascular and renal disorders such as heart failure and diabetic nephropathy, for example.

The compound of the formula (I) and the preparation process thereof are described in WO 2008/104306 and ChemMedChem 2012, 7, 1385, in which a detailed discussion of the synthetic research is disclosed in both publications. A disadvantage of the synthesis described therein is the fact that this synthesis is unsuitable for a further large-scale process, since many steps proceed at very high dilution, with very high excesses of reagents and therefore afford a relatively low overall yield. Furthermore, many intermediate chromatographic purifications are necessary, which are technically generally very laborious and entail a high consumption of solvents, which are costly and are therefore to be avoided if possible. Some stages are not achievable due to safety and process technology difficulties.

There existed a need, therefore, for an industrially practicable synthesis, which affords the compound of the formula (I) in a reproducible manner in high overall yield, low production costs and high purity and meets all regulatory requirements, in order to provide clinical trials with active ingredient and to be used for later regulatory submission.

In terms of the present invention, a very efficient synthesis has been found which allows the requirements mentioned above to be met.

In the publication ChemMedChem 2012, 7, 1385, which discloses the research scale synthesis of the compound of the formula (I), the compound of the formula (I) is prepared in 10 stages starting from vanillin with an overall yield of 3.76% of theory. The compound of the formula (I) was obtained by evaporation of chromatographic fractions as an amorphous solid; a defined crystallisation process for the final stage for polymorphic adjustment has not been described to date.

The following scheme 1 shows the known process for preparing the compound of the formula (I).

Scheme 1: Research scale synthesis of the compound of the formula (I)

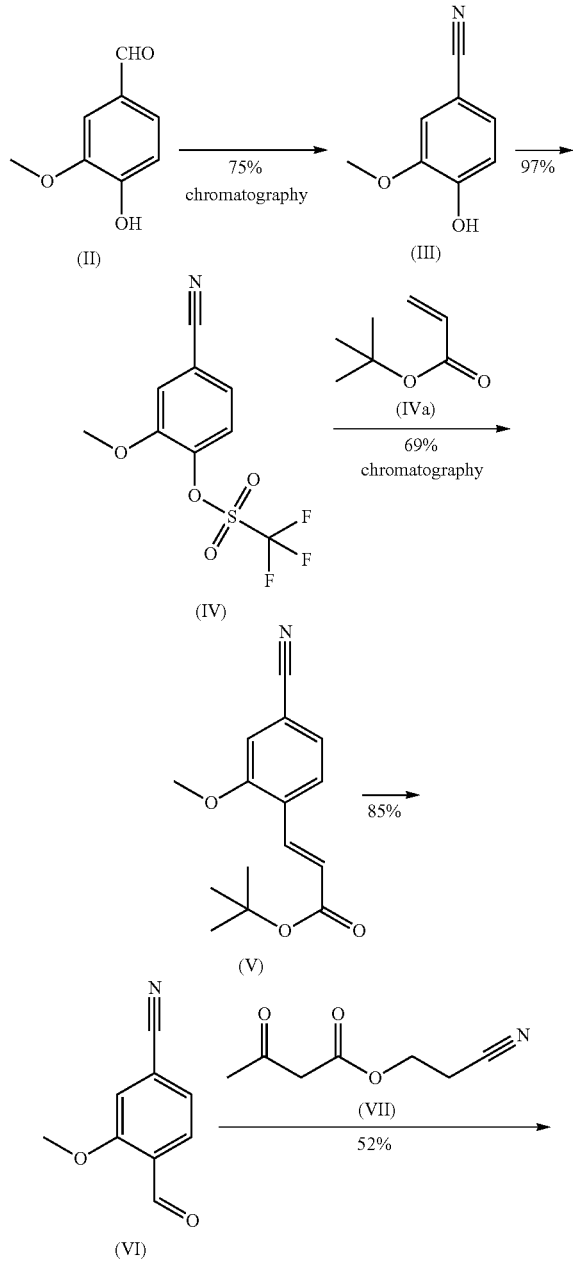

-continued

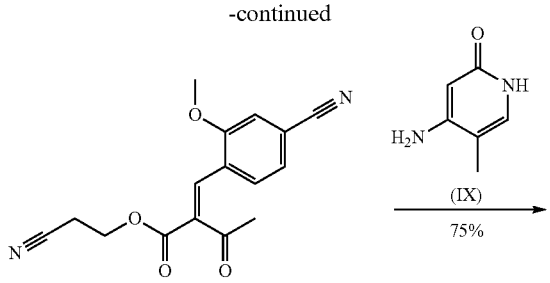

(VIII)

-continued

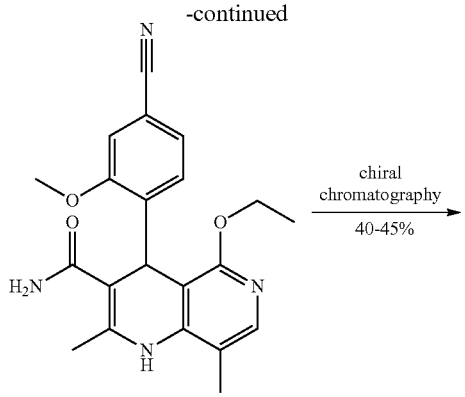

(XIII)

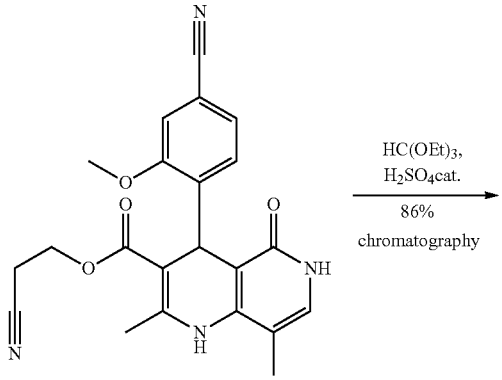

(X)

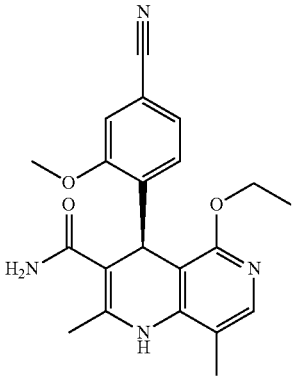

(I)

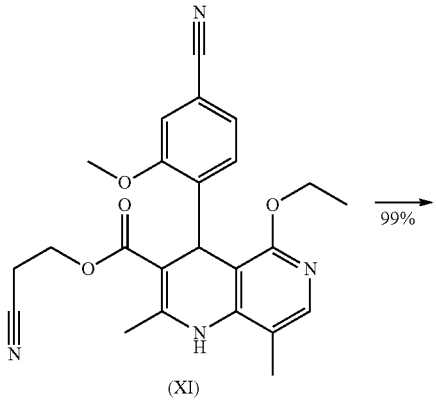

(XI)

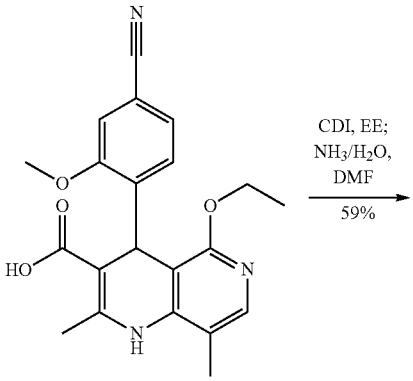

(XII)

Three chromatographic purifications are utilised and also a chiral chromatography stage for separating the enantiomers of the racemate of the formula (XIII). Some of the stages proceed at very high dilution and using very large amounts of reagent.

For instance, the sequence of the preparation of the nitrile-aldehyde intermediate (VI) in particular, which takes on a central role in this synthesis, is unacceptable in terms of atom economy.

Furthermore, this process cannot be transferred to an industrial scale since first of all very expensive reagents are used, such as trifluoromethanesulphonic anhydride [(III)=>(IV)] and excesses of tert-butyl acrylate. On scaling up the Heck reaction (IV)=>(V), a residue similar to plastic forms in the tank, which originates from the polymerisation of the tert-butyl acrylate used in excess. This is unacceptable in an industrial procedure, since the danger exists that it can cause a fracture of the stirrer and would lead to residues in the stirrer mechanism that are too hard to remove.

The subsequent cleavage of the double bond with sodium periodate and the highly toxic osmium tetroxide should also be avoided since, under the experimental conditions described, a delay of the reaction occurs and results in a strong exothermicity and therefore links to a runaway reaction.

Scheme 2 illustrates the novel process according to the invention, which affords the compound of the formula (I) in 9 stages in an overall yield of 27.7% of theory without chromatographic purification of intermediates.

Scheme 2: Process according to the invention for preparing the compound of the formula (I).
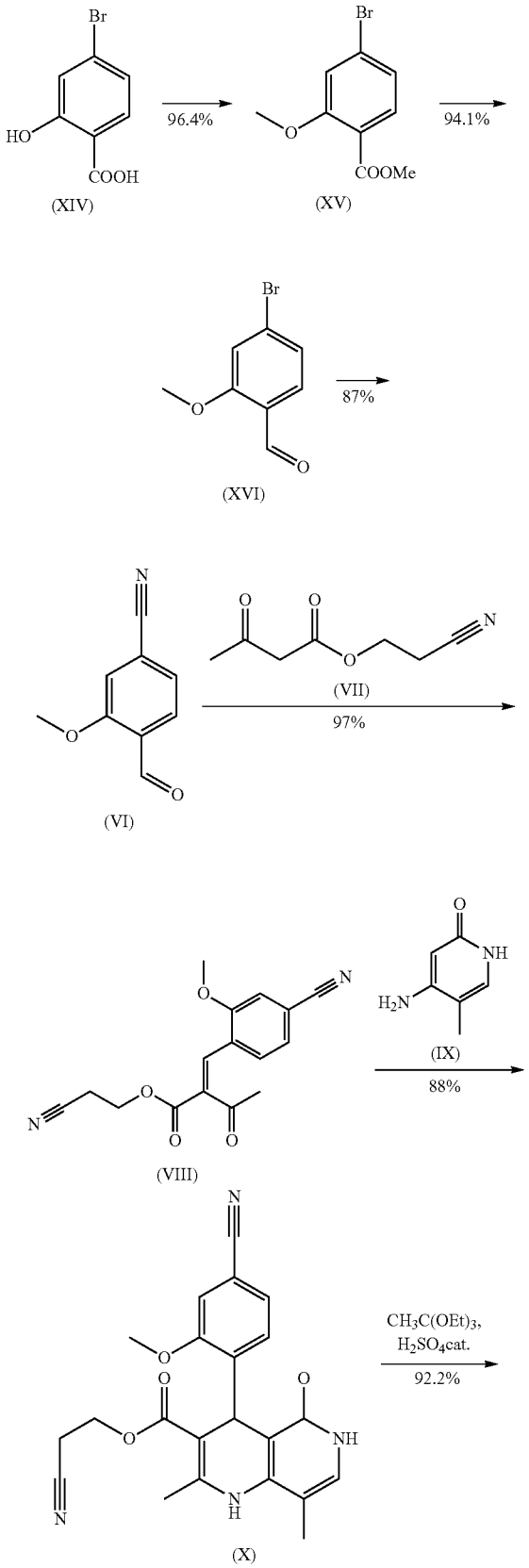
-continued
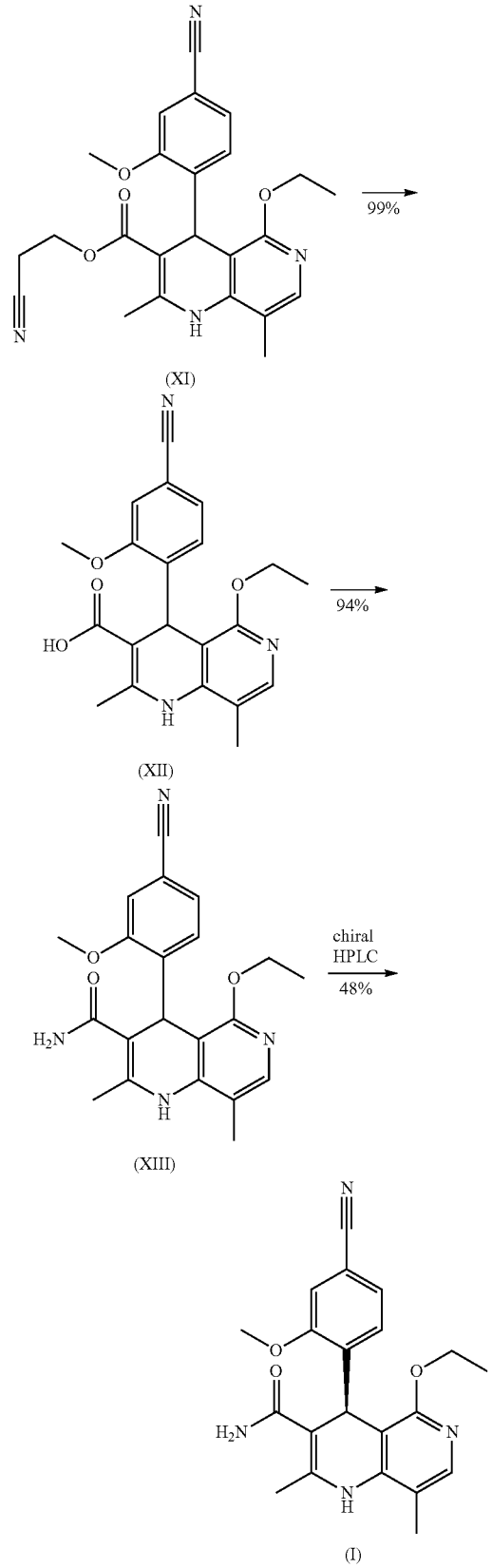
The methyl ester (XV) and the aldehyde (XVI) are not isolated but are further reacted directly in solution, which results in only 7 stages to be isolated. A preparative chiral HPLC method (e.g. SMB Technology, Varicol) is used for the enantiomer separation.

The aldehyde (VI) is known from the literature (J. Med. Chem. 2007, 50, 2468-2485) and is an important intermediate in this synthesis. Meanwhile, there is also the possibility to purchase the compound commercially.

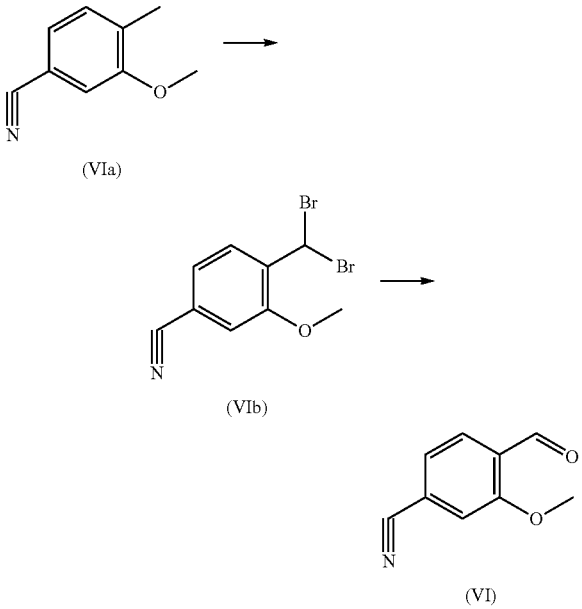

Starting from 4-cyano-2-methoxytoluene (VIa), a dibromide (VIb) is prepared with NBS, which is reacted in ethanol with 2.46 eq. of silver nitrate (in water) to the target aldehyde (VI). This synthesis described in the literature and the process described in the research scale synthesis are completely unsuitable for scaling up to the multi-tonne scale such that a great need existed for a novel, more efficient and economically more viable synthesis.

The halobenzoic acids (XIV) and (XIVa)

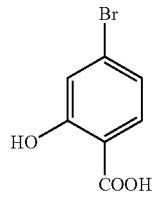

(XIV)

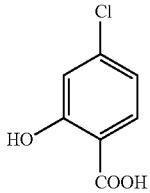

(XIVa)

are commercially available in relatively large amounts. A very efficient and cheaper process has been developed in which the intermediates (XV) and (XVI)

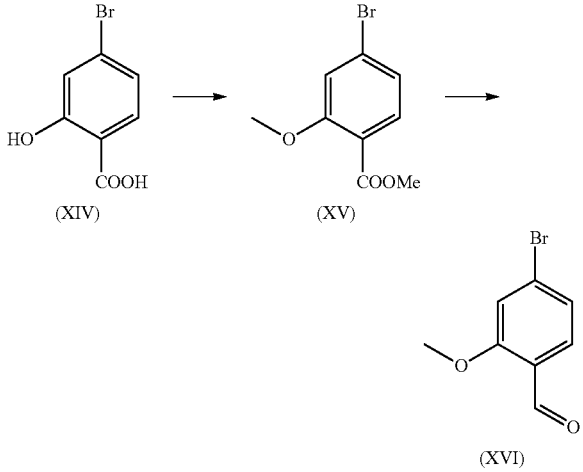

are not isolated but are further reacted dissolved in solution. This is only possible because the yield and purity of each reaction is very high (>95% of theory). The methyl ether ester (XV) is known from the literature (Journal of Medicinal Chemistry, 1992, vol. 35, p. 734-740) and is prepared by reaction with the highly volatile, harmful to health and expensive methyl iodide.

With the new process according to the invention it was possible to show that the non-volatile, less expensive dimethyl sulphate can be used analogously. Starting from the acid (XIV), said acid is reacted in a solvent such as acetone, 2-butanone, THF, 2-methyl-THF, DMF, DMA or NMP with dimethyl sulphate with the aid of an auxiliary base such as potassium carbonate, sodium carbonate, calcium carbonate, lithium carbonate, N-methylimidazole, triethylamine, pyridine or 2,6-lutidine at temperatures of 50-100° C. to give the methyl ether ester (XV). Methods known to those skilled in the art here are esterification of acids and etherification of phenols (Tetrahedron, 2013, vol. 69, p. 2807-2815, Journal of the American Chemical Society, 2013, vol. 135, p. 5656-5668). The reaction in acetone under reflux (56° C.) using dimethyl sulphate and potassium carbonate has been found to be particularly preferred. In this case, dimethyl sulphate is added to the boiling reaction mixture over 4 hours. The acetone is distilled off and replaced by toluene (redistillation). For the work-up, water is added (decomposing the excess dimethyl sulphate), the toluene phase is separated and washed with water and saturated sodium chloride solution and the toluene solution subsequently distilled off to a certain volume (serves as azeotropic drying, i.e. removal of water for the subsequent stage). Determination of the solution content shows virtually complete conversion (>96% of theory). Instead of the bromine compound, the chlorine compound may be used analogously for which the achieved conversions are identical to the bromine compound.

The preparation of the aldehyde (XVI) is described in the literature, examples of which include: Glaxo Group Limited US2008/312209 A1, 2008, European Journal of Medicinal Chemistry, 1986, vol. 21, p. 397-402, Journal of Medicinal Chemistry, 1992, vol. 35, p. 734-740, Journal of Materials Chemistry, 2011, vol. 21, p. 9523-9531. However, the starting materials used in the reactions are very expensive and not obtainable in large amounts, therefore a new method starting from the methyl ether ester (XV) was developed. The conversion of (XV) to the aldehyde (XVI) is possible using REDAL (sodium bis(2-methoxyethoxy)aluminium dihydride) in toluene by addition of N-methylpiperazine. This method is described in the literature (Synthesis 2003, No. 6, 823-828 and Tetrahedron 57 (2001) 2701-2710). If the reaction is carried out analogously to the stoichiometry stated in the literature, a further compound is found in the mixture in addition to the aldehyde. It was shown that this is the corresponding benzyl alcohol which is formed by overreduction of up to 10%. It was shown that it is important to adjust the stoichiometry of the REDAL and N-methylpiperazine to exactly 1.21 eq. of REDAL+1.28 eq. of N-methylpiperazine, making it possible to reduce this by-product, which disrupts the crystallization in the subsequent stage, to <1%. For this purpose, a 65% REDAL solution in toluene at 0-5° C. is charged (preferably 1.21 eq.) and 1.28 eq. of N-methylpiperazine is added. The solution of REDAL with N-methylpiperazine thus obtained is added over ca. 30 minutes to the bromo methyl ester solution (XIV) charged in toluene and the mixture is subsequently stirred for one hour at 0° C. The reaction solution is quenched in water/acid, preferably aqueous sulphuric acid and the toluene phase is separated and washed with water and saturated sodium chloride solution. The toluene is distilled off and redistilled in DMF (solvent for the subsequent stage). The reaction yield is generally >94% of theory. The corresponding reaction with the chloro compound proceeds analogously and the yields are equivalent. The DMF solution is used directly in the subsequent reaction.

In the further course of the synthesis, the bromoaldehyde (XVI) is converted to the nitrile in a manner known per se by methods familiar to those skilled in the art (Synth. Commun. 1994, 887-890, Angew. Chemie 2003, 1700-1703, Tetrahedron Lett. 2007, 2555-2557, Tetrahedron Lett. 2004, 1441-1444, JACS 2003, 125, 2890-2891, Journal of Organometallic Chemistry 689 (2004), 4576-4583), where in this case the nitrile aldehyde (VI) is obtained. It has proven particularly advantageous in the case of the bromo compound to carry out a palladium-catalysed reaction with potassium hexacyanoferrate*3 $H_2O$ as the cyanide source (Tetrahedron Lett. 48 (2007), 1087-1090). For this purpose, the bromoaldehyde (XVI) is charged in DMF (8-10 fold), 0.22 eq. of potassium hexacyanoferrate*3 $H_2O$ and 1 eq. of sodium carbonate is charged and then 0.005 eq. of palladium acetate is added. The mixture is heated to 120° C. for 3 hours. The solution is cooled to 20° C., then water and ethyl acetate is added. The ethyl acetate phase is separated off, the water phase washed again with ethyl acetate and the combined ethyl acetate phases then redistilled in isopropanol. The product precipitates by water precipitation at the boiling temperature. After isolation, the product is dried under vacuum. In some cases, the product was precipitated directly by addition of water to the DMF and used directly in the subsequent stage after isolation and drying. The reaction yields are generally >85% of theory. Palladium acetate is not adequate for the conversion of the chloro compound and it has proven advantageous in this case to use the palladium catalysts familiar to those skilled in the art, such as is described in Tetrahedron Lett. 48 (2007), 1087-1090, where the yields are somewhat lower than with the bromo compound, generally 80-85% of theory.

The cinnamic ester (VIII a,b) is obtained as an E/Z mixture starting from the aldehyde of the formula (VI) by a Knoevenagel reaction with the cyanoester (VIII):

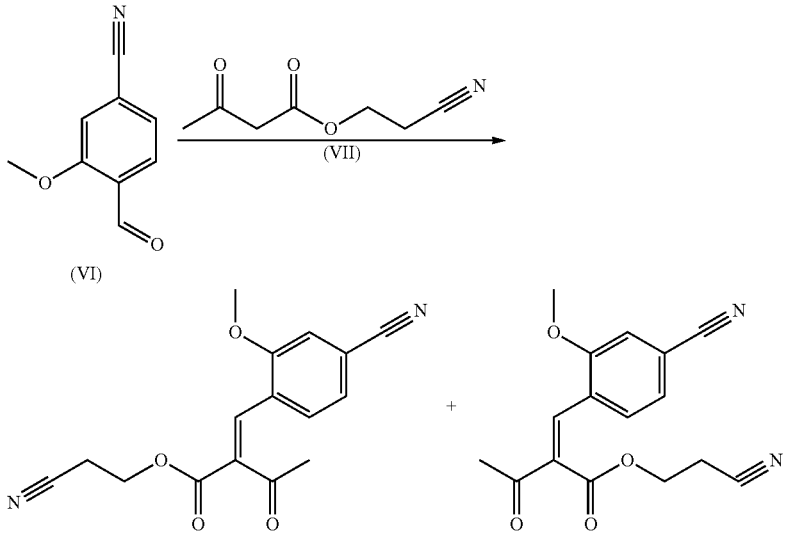

(VIII a + b)
E/Z-cinnamic ester mixture

In the research directive, 16.6 fold dichloromethane and 0.2 eq. of piperidine/0.2 eq. of glacial acetic acid were heated for 20 hours on a water separator. After aqueous work-up, the product is crystallized from methanol after evaporation of the solvent, the target compound being obtained at 52% of theory.

The reaction proceeds preferably in boiling dichloromethane (10-fold) by addition of 5-20 mol % of piperidine, preferably 10 mol % and 5-20 mol % of glacial acetic acid, preferably 5-10 mol %, on a water separator. The reaction time is 4-12 h, but preferably 5-6 h, particularly preferably 6 h. 1.0-1.5 eq, preferably however 1.1 to 1.35 eq. or 1.25 eq to 1.35 eq of the cyanoester (VII) is added. With particular preference 1.1 eq. is added. The preparation of the cyanoester (VII) is described in Pharmazie, 2000, vol. 55, p. 747-750 and Bioorg. Med. Chem. Lett. 16, 798-802 (2006). After completion, the reaction is cooled to 20° C. and the organic phase is washed twice with water. The organic wash is redistilled in 2-butanol and the E/Z cinnamic ester mixture (VIII a+b) is used directly without intermediate isolation in the subsequent reaction with the heterocycle (IX) to give the dihydropyridine (X):

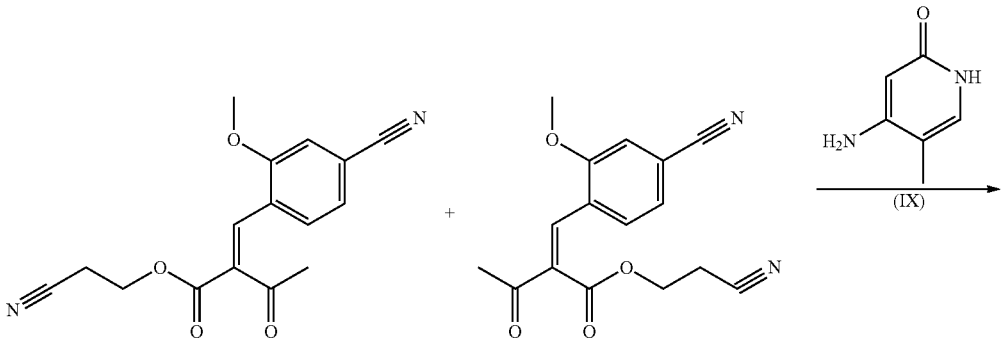

(VIII a + b)
E/Z-cinnamic ester mixture

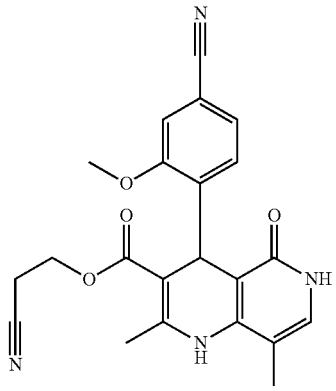

(X)

For the further reaction in the research scale synthesis, the mixture was heated under reflux with the heterocycle (IX) in isopropanol for 40 hours.

It has been found that the reaction may be carried out, preferably in a secondary alcohol such as isopropanol, isobutanol, 2-amyl alcohol or cyclohexanol at temperatures of 80-160° C., at atmospheric pressure and also in autoclaves (2-10 bar), with reaction times of 8-40 h, but preferably for 20-25 h in boiling 2-butanol at atmospheric pressure or else in isopropanol in an autoclave (100° C., 2-10 bar, preferably 3-5 bar, 8-24 h). For work-up, the mixture is cooled to 0° C. to 20° C., the crystals filtered off and washed with isopropanol and then dried (in vacuum, 60° C.).

If the use of dichloromethane should be omitted for environmentally economic reasons, it has proven to be advantageous to prepare the cinammic ester (VIII a,b) in isopropanol, in which case the aldehyde (VI) is charged in isopropanol (3-9 fold, preferably 5-7 fold) and 5-20 mol % of piperidine, preferably 5-10 mol %, 10 mol % and 5-20 mol % of glacial acetic acid, preferably 5-10 mol % or 10 mol % is added. At 30° C., 1.0-1.5 eq, preferably 1.1-1.35 eq. or 1.35 eq., particularly preferably 1.1 eq. of cyanoester (VII) is added over 3 hours, optionally dissolved in a little isopropanol, and the mixture is stirred at 30° C. for 1 hour. The cinammic ester (VIIIa,b) crystallizes out during the reaction. The product is subsequently filtered off, optionally after cooling, preferably at 0° C., washed with a little isopropanol (cooled to 0° C.) and used moist in the subsequent reaction as described above. The yield is >96% of theory. The subsequent reaction is preferably performed in 10-15 fold (with respect to aldehyde (VI)), preferably 11-12 fold isopropanol for 20-24 hours at 100° C. under pressure.

After termination of the reaction and cooling, the product is isolated by filtration or centrifugation. The product is subsequently dried at 40-90° C. under vacuum. Since the conversion to the cinammic ester proceeds virtually quantitatively, the process for the subsequent stage can be readily standardised without having to adjust the amount of heterocyle (IX) in each case, as the product can be used moist with isopropanol. The yields are >87% of theory. The heterocycle (IX) can be prepared by known literature methods such as is described, for example, in Synthesis 1984, 765-766.

Starting from the dihydropyridine (X), the ethyl ether (XI) is obtained by reaction under acidic catalysis with an orthoester, where R is —H or -methyl:

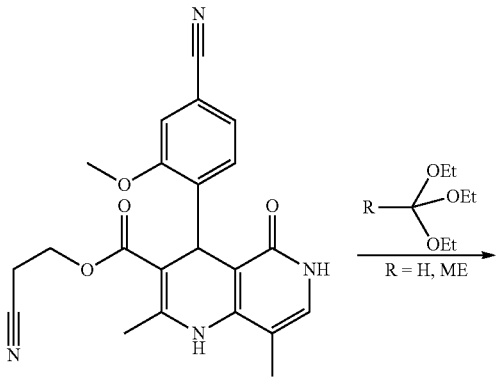

(X)

-continued

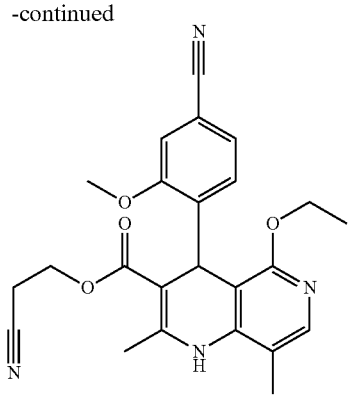

(XI)

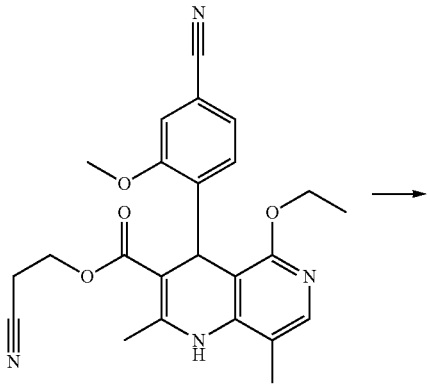

(XI)

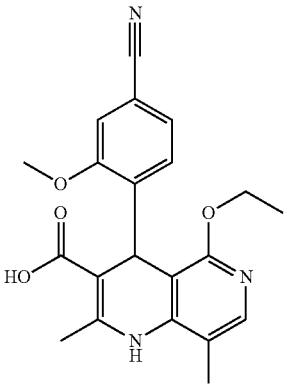

(XII)

In the research scale synthesis, the reaction was carried out in 25 fold DMF with 20.2 eq. of triethyl orthoformate and catalytic amounts of conc. sulphuric acid at 135° C. The mixture was concentrated to dryness and the residue was purified by chromatography with a yield of 86% of theory. This method is unsuitable as a technical procedure due to the high dilution and the use of triethyl orthoformate, highly flammable at low temperature, which is used in very large excess, and the subsequent chromatography.

It has been found, surprisingly, that the reaction can be carried out highly concentrated (up to 1.5 g of solvent per 1 g of reactant) in solvents such as dimethylacetamide, NMP (1-methyl-2-pyrrolidone) or DMF (dimethylformamide) by addition of 4-10% by weight, preferably 6-8% by weight, of conc. sulphuric acid. The reaction proceeds, surprisingly, even with 2.5-5 eq. or 5 eq. of orthoester. It has been found that it is much more convenient to use the corresponding triethyl orthoacetate in the reaction, since it reacts much more cleanly on the one hand and is much less inflammable, making it particularly appropriate for the technical procedure. The reaction is preferably carried out in DMA (dimethylacetamide) and/or NMP (1-methyl-2-pyrrolidone), at temperatures of 100-120° C., preferably 115° C. Before starting the actual reaction, it has proven advantageous to distill off some of the solvent (DMA and/or NMP) at elevated temperature (100-120° C. under vacuum) in order to remove any residues of isopropanol present from the precursor, as otherwise undesirable by-products occur. Reaction: Stir for 1.5-3 hours, preferably 2 hours. For the work-up, water is added directly to the mixture, wherein the product crystallizes out. In order to have a particularly stable and reproducible process, a portion of the water (e.g. ⅓) is first added, then it is seeded, and the remaining amount of the water is added. This procedure guarantees that the same crystal polymorph is always obtained, which shows the optimum isolation characteristics. The product is washed with water and dried. The yields are >92% of theory.

Starting from the ethyl ether (XI), the acid (XII) is obtained by alkaline saponification and subsequent acidic work-up.

In the research scale synthesis, the saponification was carried out at high dilution (33.9 fold) in a mixture of DME/water 3:1. Here, it was essential primarily to increase throughput and to replace the DME (dimethoxyethane) used, which has a very low flash point and is therefore considered to be particularly critical for large-scale use. It has been found, surprisingly, that the reaction can also be conducted very readily highly concentrated in mixtures of THF/water. For this purpose, the reaction is preferably performed in a mixture of THF/water 2:1 (9-fold), the aqueous sodium hydroxide solution is added at 0-5° C., then the mixture is stirred at 0-5° C. for 1-2 hours. Aqueous potassium hydroxide can also be used but NaOH is preferably used. For the work-up, the mixture is extracted with MTBE (methyl tert-butyl ether) and ethyl acetate and for the isolation the pH is adjusted with a mineral acid such as hydrochloric acid, sulphuric acid or phosphoric acid, but preferably hydrochloric acid, to pH 6.5-7.0 or pH 7. The mixture is then mixed with saturated ammonium salt solution of the corresponding acid, but preferably ammonium chloride solution, wherein the product quantitatively crystallizes out. After isolation, the product is washed with water and with ethyl acetate or acetonitrile or acetone, but preferably acetonitrile, and dried under vacuum at 40-50° C. The yield is virtually quantitative (99%). Alternative preferred work-up: As an alternative work-up, toluene is added to the mixture, sodium acetate is added and the mixture is stirred at 20° C., the phases are then separated and the aqueous phase is adjusted at 0° C. with 10% aqueous hydrochloric acid to pH 6.5-7.0 (may optionally be seeded at pH 9.5-10). The mixture is briefly stirred and the product filtered off, washed with a little water and toluene and dried at 40-50° C. under vacuum. The yields achieved are also quantitative in this case.

The subsequent conversion of the acid to the amide (XIII) was carried out in the research stage as follows: The acid (XII) was dissolved in ca. 10-fold DMF, 1.25 eq. of 1,1'-carbodiimidazole and 0.1 eq. of DMAP (4-(dimethylamino) pyridine) were added and the mixture was stirred at room temperature for 4 hours. Subsequently, 20 eq. of ammonia in the form of an aqueous 25% solution were added and this mixture transferred to an oilbath pre-heated to 110° C. In this procedure, relatively large amounts of ammonia gas form instantaneously, which escape the system and in addition ensure a sharp increase in pressure. This mixture was added to ca. 90-fold water and adjusted to pH 7 by addition of sodium acetate. The precipitated product was filtered off and dried (yield: 59% of theory). A further portion was isolated from the mother liquor by exhaustive extraction (ca. 100 fold ethyl acetate), which was stirred with highly flammable diethyl ether and comprised ca. 14% DMF. It is clear that such a method cannot be achieved in such a manner in an operational framework and therefore there is a high demand for an alternative procedure. The effort required for the isolation of this portion is disproportionate to the amount isolated in this case.

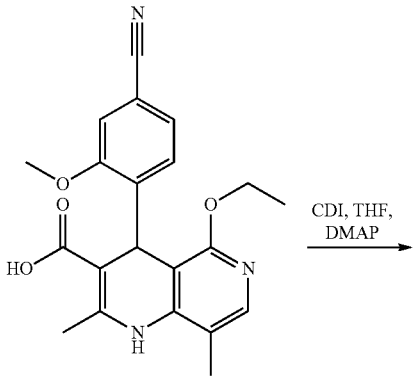

(XII)

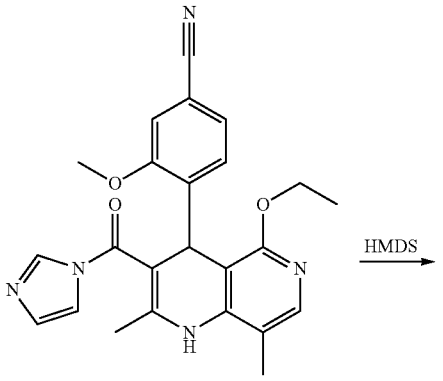

-continued

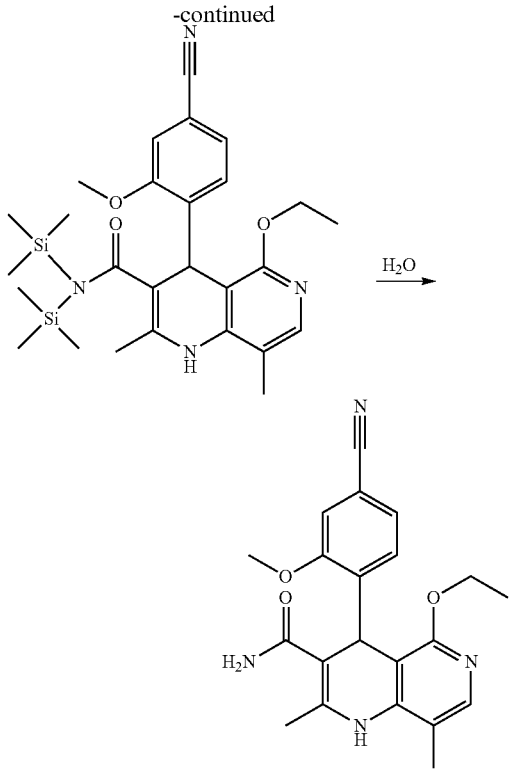

(XIII)

It has been found, surprisingly, that in the reaction of the acid (XII) in THF, the amide (XIII) crystallises out directly from the solution and can be obtained in high yield and purity. For this purpose, the carboxylic acid (XII) in THF is reacted with 1.1 to 1.6 eq., preferably 1.3-1.4 eq. of 1,1'-carbodiimidazole under DMAP catalysis (5-15 mol %, preferably 10 mol %) to give the imidazolide, which takes place at temperatures between 20-50° C., the preferred approach having proven to be initially starting at 20° C., then stirring 1 to 2 hours at this temperature and then further stirring at 50° C. for 2 to 3 hours. After completion of the activation, 3-8 eq, preferably 4.5 eq. of hexamethyldisilazane is added and the mixture is boiled under reflux for 16-24 hours, but preferably 16 hours. The resulting disilylamide compound here can optionally be isolated but it has been proven to be advantageous to continue in a one-pot reaction. Therefore, on completion of the reaction, the mixture is cooled to 0-3° C. and a mixture of water/or in a mixture with THF is added, it having proven to be advantageous to use an amount of water of 0.5 to 0.7 fold (with respect to reactant), particularly advantageous being an amount of water of 0.52 fold. The water can be added directly or as a mixture with approximately an equivalent up to double the amount of THF by volume. After quenching is complete, the mixture is heated under reflux for 1-3 hours in total, preferably 1 hour. The mixture is cooled to 0° C. and stirred for 1-5 hours, preferably 3 hours, at this temperature, then the product is isolated by filtration or centrifugation. The product is washed with THF and water and dried under vacuum at elevated temperature (30 to 100° C., preferably at 60° C. to 90° C. or at 40° C. to 70° C.). The yields are very high and are generally >93% of theory. The purity is generally >99% (HPLC, 100% method). The compound (XIII) may also be obtained directly by reacting with ammonia gas in the autoclave (ca. 25 to 30 bar). For this purpose, the preactivation described above is carried out and the reaction mixture is heated under pressure under gaseous ammonia. On completion of the reaction, it is cooled and the product filtered off. The yields and purities thus achieved are comparable.

To obtain the compound of the formula (I), the racemic mixture of amides (XIII) must be separated into the antipodes. In the published research scale synthesis, a specifically synthesized chiral phase was used for this purpose (prepared in-house), which comprised N-(dicyclopropylmethyl)-$N^2$-methacryloyl-D-leucinamide as chiral selector. This selector was prepared in a multi-stage process and then polymerized on special silica gel. Methanol/ethyl acetate served as eluent. A major disadvantage of this method was the very low loading, 30 mg per separation on a 500*63 mm chromatography column, such that there was a high need to find as effective a separation method as possible which allows separation of antipodes to be performed in the multi-tonne range. It has been found, surprisingly, that the separation can be performed on a readily commercially available phase. This takes the form of the phase Chiralpak AS-V, 20 μm. The eluent used was a mixture of methanol/acetonitrile 60:40. This mixture has the major advantage that it can be recovered as eluent after distillative work-up having the identical composition (60:40 corresponds to the azeotrope. A very efficient process is achieved in this way in which the yield of the separation is >47% of theory (50% is theoretically possible). The optical purity here is >93% e.e. but preferably >98.5% e.e. In this case, the chromatography may be carried out on a conventional chromatography column, but preferably the techniques known to those skilled in the art such as SMB or Varicol (Computers and Chemical Engineering 27 (2003) 1883-1901) are used. For instance, ca. 500 kg of the racemic amide (XIII) was separated using an SMB system, in which a yield of 48% was achieved. The product is obtained as a 3-8%, preferably 5-7% solution in a mixture of methanol/acetonitrile 60:40 and can be used directly in "final processing". Other solvent mixture ratios of acetonitrile to methanol are also conceivable (90:10 to 10:90). Alternatively, other solvent mixtures can also be used, however, for the SMB separation, such as acetonitrile/ethanol in mixture ratios of 10:90 to 90:10. The particular solvent ratio depends partly on the technical properties of the SMB system and must be adjusted, if appropriate (e.g. varying flow rate, recycling of the solvent on a thin film evaporator).

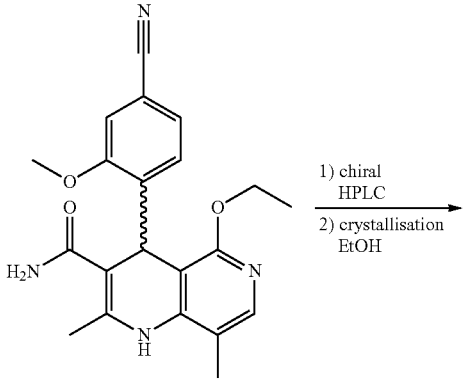

racemic
(XIII)

-continued

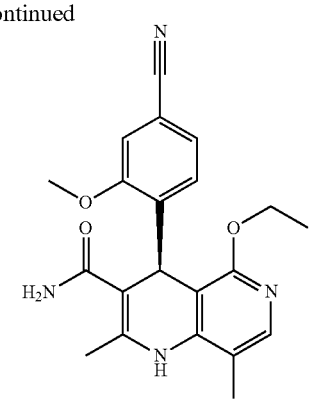

(I)

Since the compound of the formula (I) has been developed in the form of a tablet, there exists a high demand that the isolated compound of the formula (I) is isolated in a defined crystalline form in a reproducible manner such that a reproducible bioavailability can be ensured. It has been found, surprisingly, that the compound of the formula (I) can be crystallized from methanol, ethanol, THF, acetonitrile, and also mixtures thereof with water, wherein only one polymorph I is reproducibly formed, which has a defined melting point of 252° C. By way of advantage, ethanol or denatured ethanol is used.

Final crystallization process: For this purpose, the ca. 5-7% product solution in methanol/acetonitrile 60:40 (or, if ethanol/acetonitrile was employed, a ca. 3-4% solution of ethanol/acetonitrile 50:50) originating from the chromatography is firstly subjected to a particle filtration for GMP technical reasons and subsequently a solvent exchange with ethanol is performed, preferably using ethanol denatured with toluene. For this purpose, the solution is repeatedly redistilled, concentrated and fresh ethanol added each time. After exchange, as much ethanol is added until a solution phase is passed through at the boiling point and then it is concentrated under atmospheric pressure or under slightly reduced pressure to ca. 3 to 4 fold by volume, whereupon the product crystallizes out. This is cooled to 0° C. and the crystals then isolated and dried at 40-50° C. under vacuum. The yields are generally >90% of theory. The chemical purity achieved is >99.8% and the content ~100% correspond to the criteria for commercial products according to ICH guidelines. Residual solvent, in the case of ethanol, is <0.02%. The optical purity is >>99% e.e.

The present invention provides the compound of the formula (I) in crystalline form of polymorph I (I)

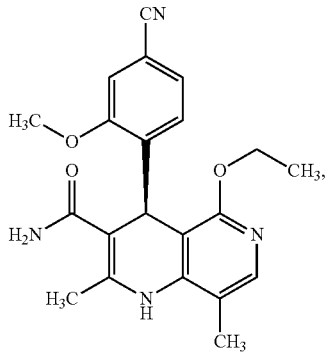

characterized in that the x-ray diffractogram of the compound exhibits peak maxima of the 2 theta angle at 8.5, 14.1, 17.2, 19.0, 20.5, 25.6, 26.5.

The present invention further provides the compound of the formula (I) in crystalline form of polymorph I (I)

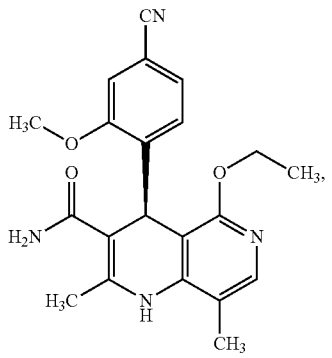

characterized in that the IR spectrum (IR-ATR) of the compound exhibits band maxima at 3475, 2230, 1681, 1658, 1606, 1572, 1485, 1255, 1136 and 1031 $cm^{-1}$.

The present invention further provides the compound of the formula (I) in crystalline form of polymorph I (I)

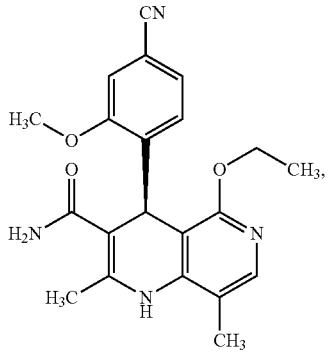

characterized in that the Raman spectrum of the compound exhibits band maxima at 3074, 2920, 2231, 1601, 1577, 1443, 1327, 1267, 827 and 155 $cm^{-1}$.

The present invention further provides a process for preparing the compound of the formula (I) in crystalline form of polymorph I, characterized in that the compound of the formula (I), present in one or more polymorphs or as a solvate in an inert solvent, is stirred at a temperature of 20° C.-120° C. and the compound of the formula (I) is isolated in crystalline polymorph I.

Preferred solvents for the process for preparing the compound of the formula (I) in crystalline form of polymorph I are methanol, ethanol, THF, acetonitrile, and also mixtures thereof. Particular preference is given to ethanol or denatured ethanol.

A preferred temperature range for the process for preparing the compound of the formula (I) in crystalline form of polymorph I is from 20° C. to 90° C.

The present invention further provides a compound of the formula (I) in crystalline form of polymorph (I) as described above for treatment of disorders.

The present invention further provides a medicament comprising a compound of the formula (I) in crystalline form of polymorph (I) as described above and no greater proportions of any other form of the compound of the formula (I) in crystalline form of polymorph (I) as described above. The present invention further provides a medicament comprising a compound of the formula (I) in crystalline form of polymorph (I) as described above in more than 90 percent by weight based on the total amount of the compound of the formula (I) present in crystalline form of polymorph (I) as described above.

The present invention further provides for the use of the compound of the formula (I) in crystalline form of polymorph I as described above. To prepare a medicament for the treatment of cardiovascular disorders.

The present invention further provides the method for treatment of cardiovascular disorders by administering an effective amount of a compound of the formula (I) in crystalline form of polymorph (I) as described above.

The present invention further provides a process for preparing compound (I), characterized in that the compound of the formula (XIV) or the formula (XIVa)

(XIV)

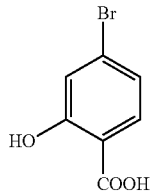

(XIVa)

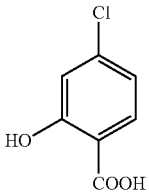

are reacted by addition of dimethyl sulphate to give the compound of the formula (XV) or (XVa)

(XV)

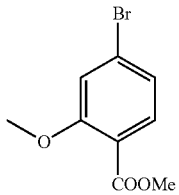

(XVa)

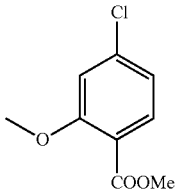

and the non-isolated methyl esters of the formula (XV) or (XVa) are reduced with 1.21 eq of REDAL (solution bis(2-methoxyethoxy)aluminium dihydride and 1.28 eq of N-methylpiperazine to give the aldehyde of the formula (XVI) or (XVIa)

(XVI)

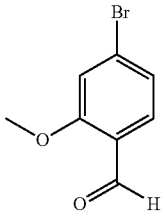

(XVIa)

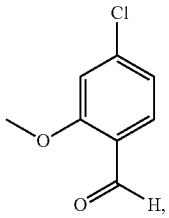

and the aldehyde (XVI) or (XVIa) is reacted further without isolation to give the nitrile of the formula (VI)

(VI)

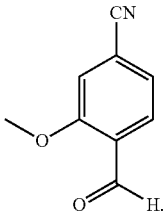

The present invention further provides a process for preparing compound of the formula (I), characterized in that the compound of the formula (VI)

(VI)

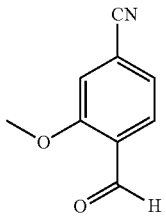

dissolved in isopropanol (3-7 fold), 5-10 mol % of piperidine and 5-10 mol % of glacial acetic acid at 30° C. is reacted with the compound of the formula (VII)

(VII)

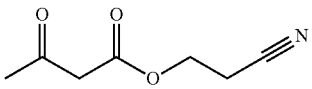

to give the compounds (VIIIa+b).

(VIII a+b)

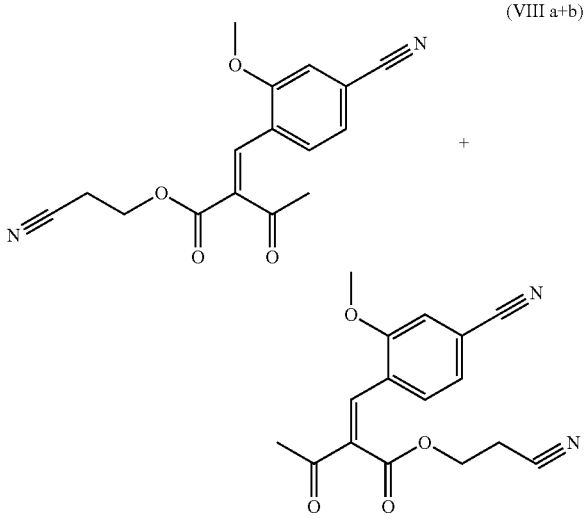

The present invention further provides a process for preparing compound of the formula (I), characterized in that the compound of the formula (X)

(X)

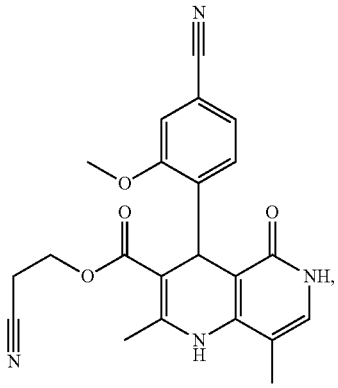

is reacted while stirring with 2.5-5 eq of triethyl orthoacetate in dimethylacetamide at 100 to 120° C. for 1.5 to 3 hours to give the compound of the formula (XI)

(XI)

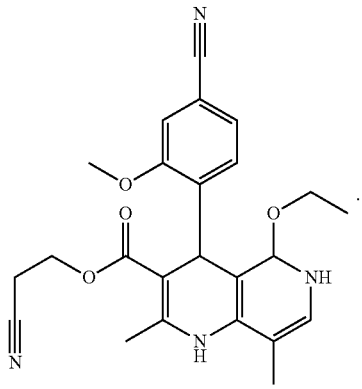

-continued (XI)

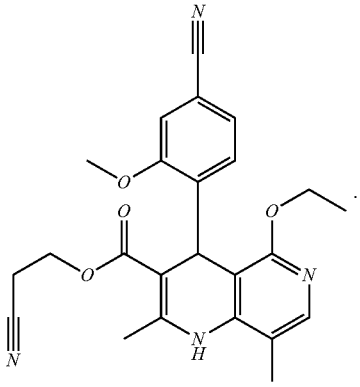

The present invention further provides a process for preparing compound of the formula (I), characterized in that the compound of the formula (XI)

[

(XI)

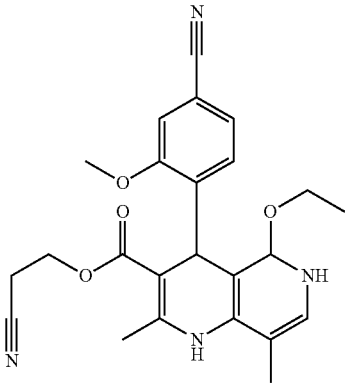

]

(XI)

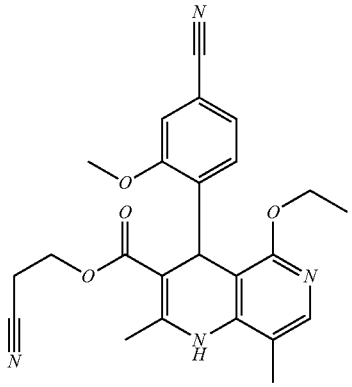

is saponified in a THF/water mixture (2:1, 9-fold) with aqueous sodium hydroxide solution to give the compound of the formula (XII)

[

(XII)

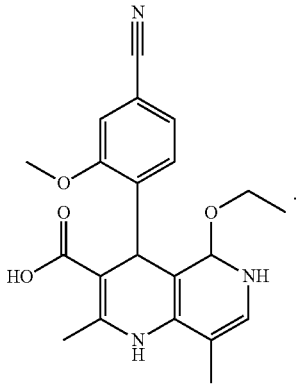

]

(XII)

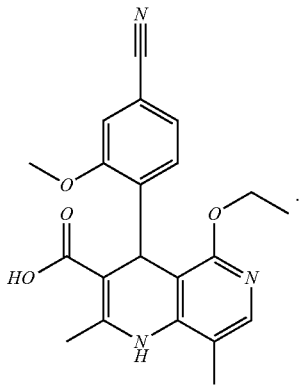

The present invention further provides a process for preparing compound of the formula (I), characterized in that the compound of the formula (XII)

[

(XII)

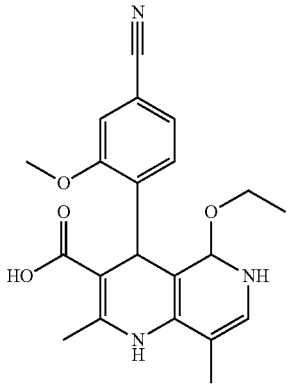

]

-continued (XII)

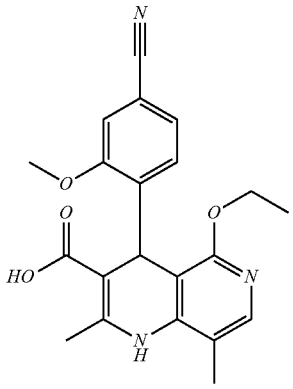

is reacted in a one-pot reaction in THF firstly with carbodiimidazole and catalytic amounts of 4-(dimethylamino) pyridine, in a second step is heated under reflux together with hexamethyldisilazane for 16 to 24 hours and in a third step is hydrolysed in water with THF or water to give the compound of the formula (XIII)

(XIII)

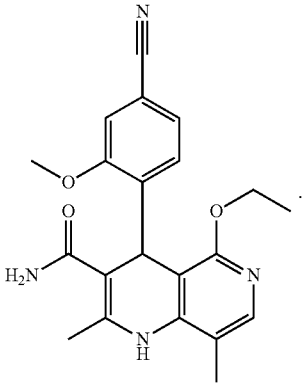

The present invention further provides a process for preparing compound of the formula (I), characterized in that the compound of the formula (XIV) or the formula (XIVa)

(XIV)

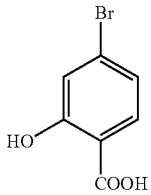

(XIVa)

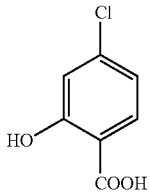

are reacted by addition of dimethyl sulphate to give the compound of the formula (XV) or (XVa)

(XV)

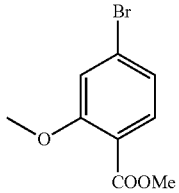

(XVa)

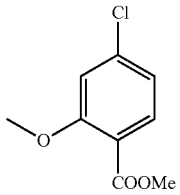

and the non-isolated methyl esters of the formula (XV) or (XVa) are reduced with 1.21 eq of REDAL (sodium bis(2-methoxyethoxy)aluminium dihydride and 1.28 eq of N-methylpiperazine to give the aldehyde of the formula (XVI) or (XVIa)

(XVI)

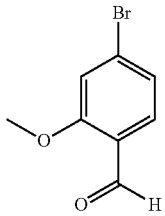

(XVIa)

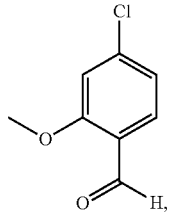

and the aldehyde (XVI) or (XVIa) is reacted further without isolation to give the nitrile of the formula (VI)

(VI)

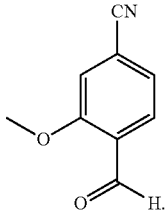

and the compound of the formula (VI)

(VI)

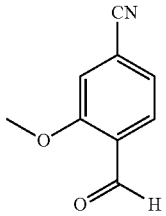

dissolved in isopropanol (3-7 fold), 5-10 mol % of piperdine and 5-10 mol % of glacial acetic acid at 30° C. is reacted with the compound of the formula (VII)

(VII)

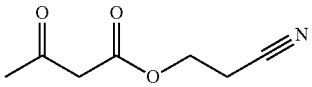

to give the compounds (VIIIa+b).

(VIII a+b)

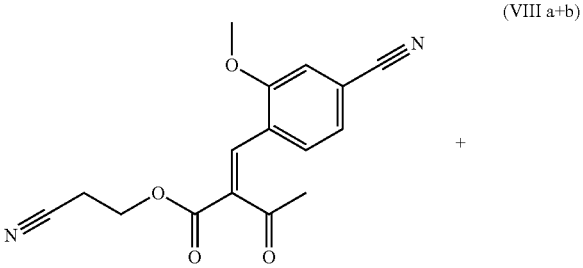

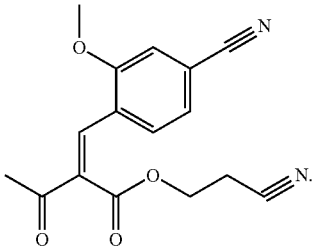

The present invention further provides a process for preparing compound of the formula (I), characterized in that the compound of the formula (VI)

(VI)

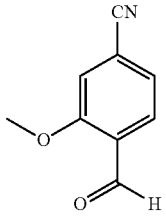

dissolved in isopropanol (3-7 fold), 5-10 mol % of piperidine and 5-10 mol % of glacial acetic acid at 30° C. is reacted with the compound of the formula (VII)

(VII)

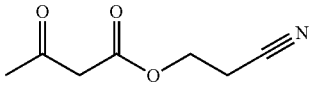

to give the compounds (VIIIa+b)

(VIII a+b)

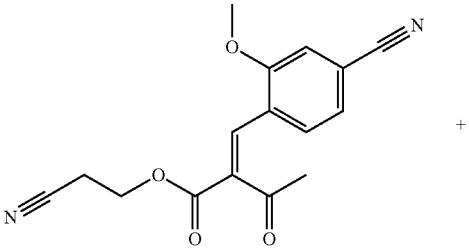

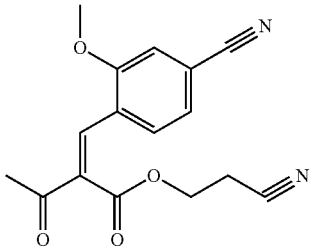

and that the compound of the formula (X)

(X)

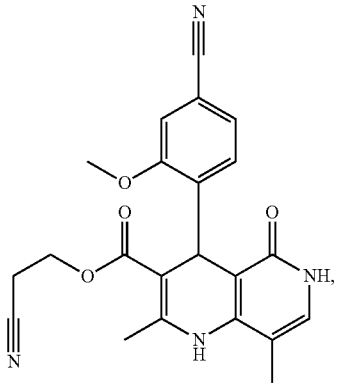

is reacted while stirring with 2.5-5 eq of triethyl orthoacetate in dimethylacetamide at 100 to 120° C. for 1.5 to 3 hours to give the compound of the formula (XI)

(XI)
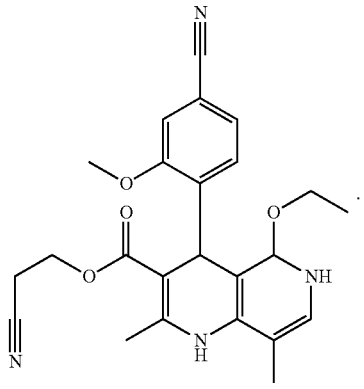
(XI)
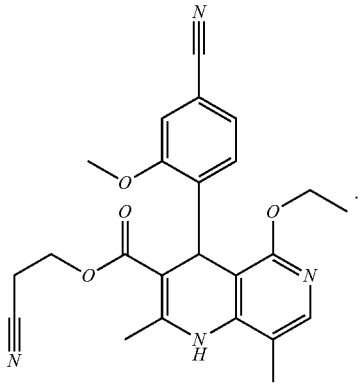
The present invention further provides a process for preparing compound of the formula (I), characterized in that the compound of the formula (X)
(X)
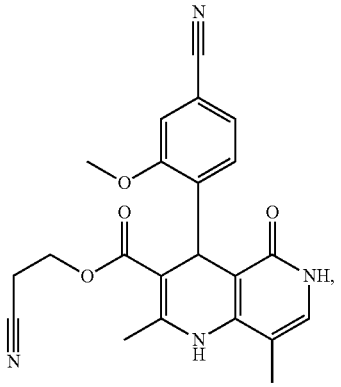
is reacted while stirring with 2.5-5 eq of triethyl orthoacetate in dimethylacetamide at 100 to 120° C. for 1.5 to 3 hours to give the compound of the formula (XI)
(XI)
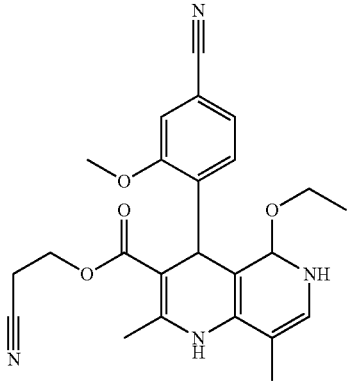
(XI)
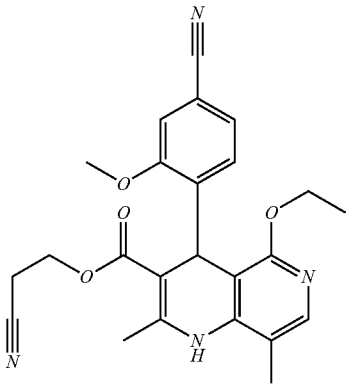
and that the compound of the formula (XI)
(XI)
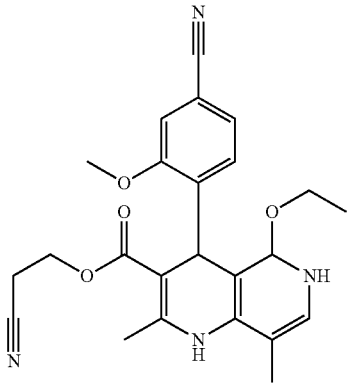

-continued (XI)

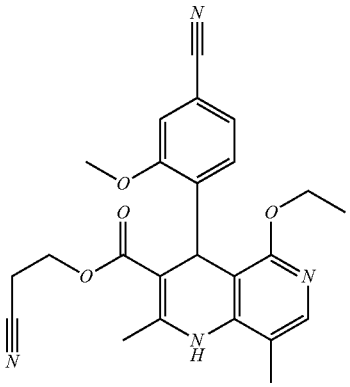

is saponified in a THF/water mixture (2:1, 9-fold) with aqueous sodium hydroxide solution to give the compound of the formula (XII)

(XII)

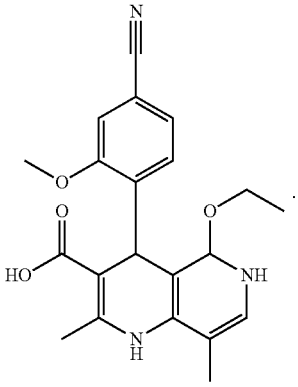

(XII)

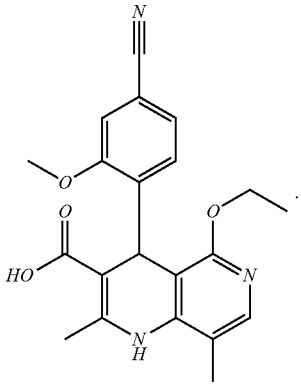

The present invention further provides a process for preparing compound of the formula (I), characterized in that the compound of the formula (XI)

(XI)

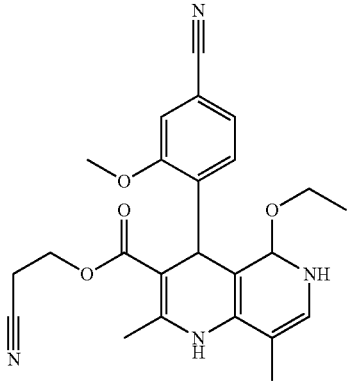

(XI)

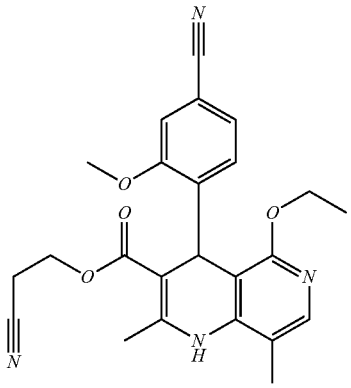

is saponified in a THF/water mixture (2:1, 9-fold) with aqueous sodium hydroxide solution to give the compound of the formula (XII)

(XII)

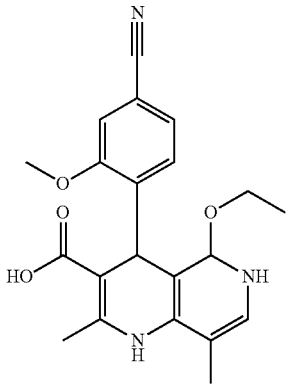

-continued (XII)

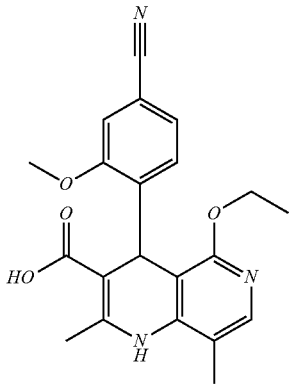

and that the compound of the formula (XII)

(XII)

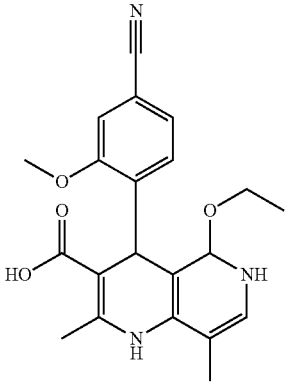

(XII)

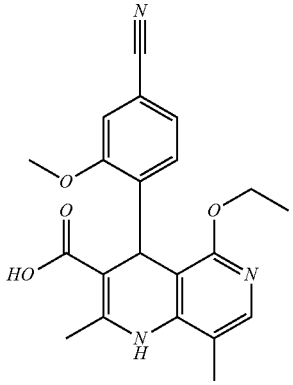

is reacted in a one-pot reaction in THF firstly with carbodiimidazole and catalytic amounts of 4-(dimethylamino) pyridine, in a second step is heated under reflux together with hexamethyldisilazane for 16 to 24 hours and in a third step is hydrolysed in water with THF or water to give the compound of the formula (XIII)

(XIII)

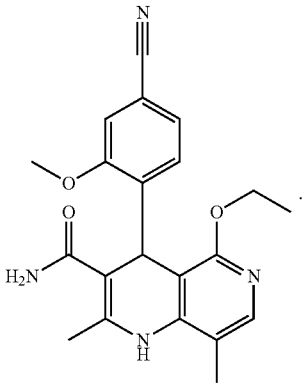

The present invention further provides a process for preparing compound of the formula (I), characterized in that the compound of the formula (XIV) or the formula (XIVa)

(XIV)

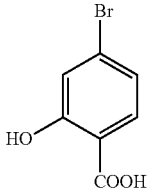

(XIVa)

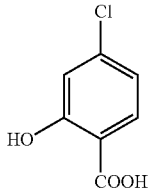

are reacted by addition of dimethyl sulphate to give the compound of the formula (XV) or (XVa)

(XV)

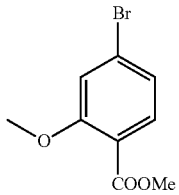

(XVa)

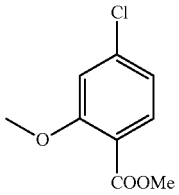

and the non-isolated methyl esters of the formula (XV) or (XVa) are reduced with 1.21 eq of REDAL (sodium bis(2-methoxyethoxy)aluminium dihydride and 1.28 eq of N-methylpiperazine to give the aldehyde of the formula (XVI) or (XVIa)

(XVI)

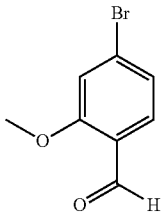

(XVIa)

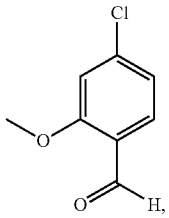

and the aldehyde (XVI) or (XVIa) is reacted further without isolation to give the nitrile of the formula (VI)

(VI)

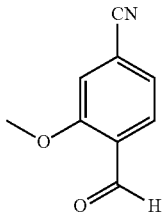

and the compound of the formula (VI)

(VI)

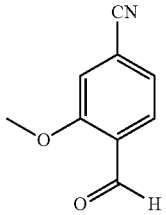

dissolved in isopropanol (3-7 fold), 5-10 mol % of piperidine and 5-10 mol % of glacial acetic acid at 30° C. is reacted with the compound of the formula (VII)

(VII)

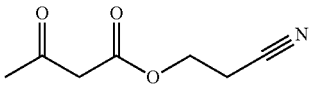

to give the compounds (VIIIa+b)

(VIII a+b)

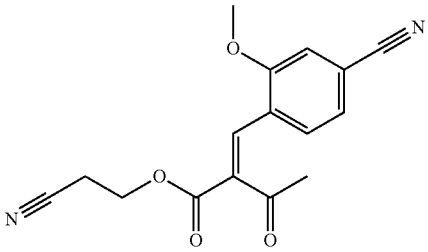

+

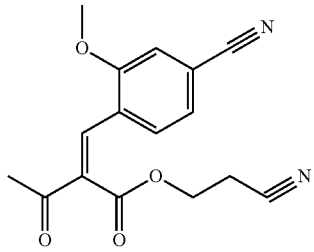

and that the compound of the formula (X)

(X)

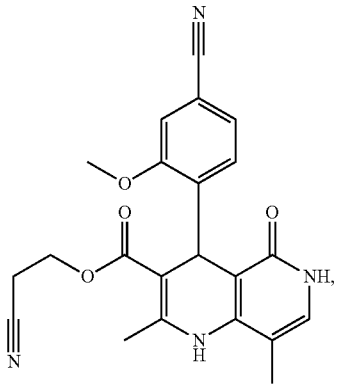

is reacted while stirring with 2.5-5 eq of triethyl orthoacetate in dimethylacetamide at 100 to 120° C. for 1.5 to 3 hours to give the compound of the formula (XI)

(XI)

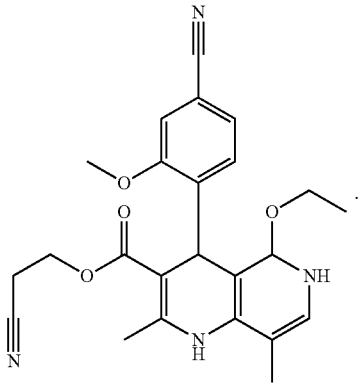

-continued (XI)

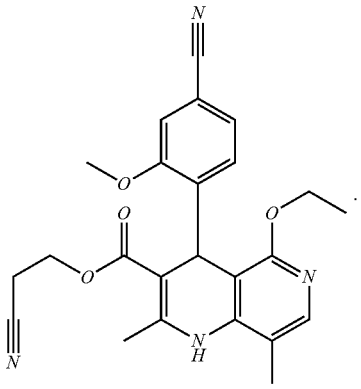

The present invention further provides a process for preparing compound of the formula (I), characterized in that the compound of the formula (VI)

(VI)

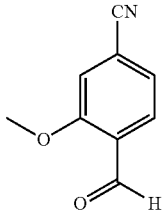

dissolved in isopropanol (3-7 fold), 5-10 mol % of piperidine and 5-10 mol % of glacial acetic acid at 30° C. is reacted with the compound of the formula (VII)

(VII)

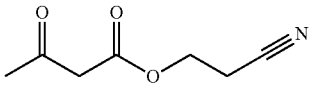

to give the compounds (VIIIa+b)

(VIII a+b)

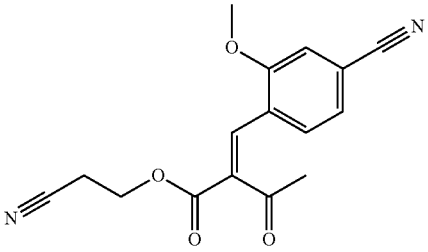

-continued

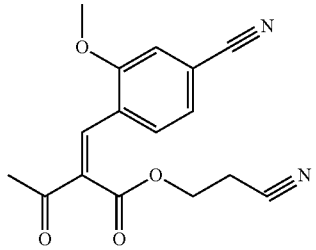

and that the compound of the formula (X)

(X)

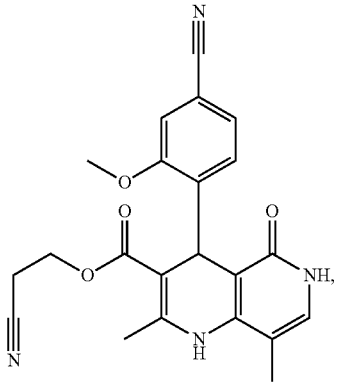

is reacted while stirring with 2.5-5 eq of triethyl orthoacetate in dimethylacetamide at 100 to 120° C. for 1.5 to 3 hours to give the compound of the formula (XI)

(XI)

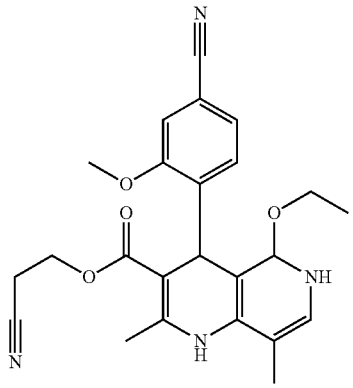

-continued (XI)

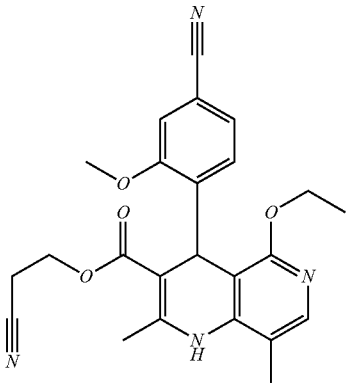

and that the compound of the formula (XI)

(XI)

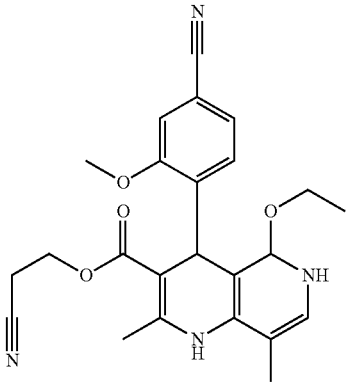

(XI)

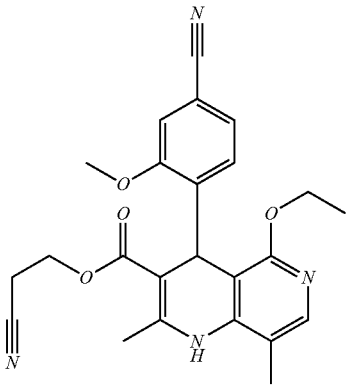

is saponified in a THF/water mixture (2:1, 9-fold) with aqueous sodium hydroxide solution to give the compound of the formula (XII)

(XII)

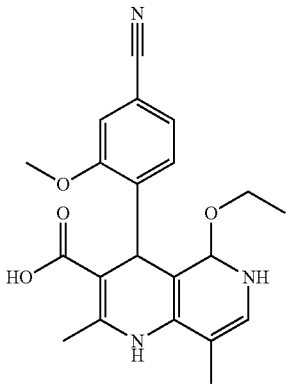

(XII)

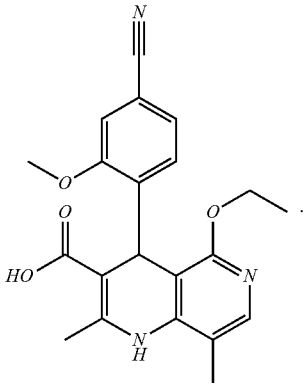

The present invention further provides a process for preparing compound of the formula (I), characterized in that the compound of the formula (X)

(X)

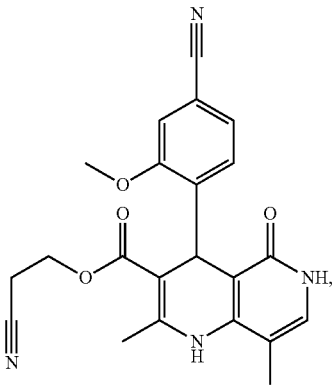

is reacted while stirring with 2.5-5 eq of triethyl orthoacetate in dimethylacetamide at 100 to 120° C. for 1.5 to 3 hours to give the compound of the formula (XI)

(XI)
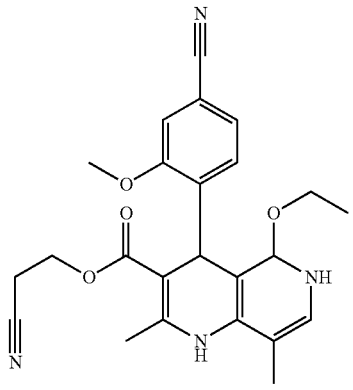
(XI)
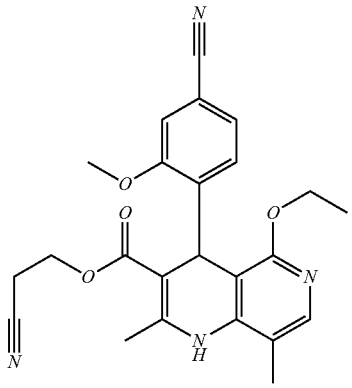
and that the compound of the formula (XI)
(XI)
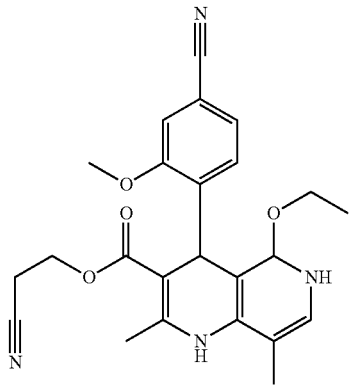
-continued
(XI)
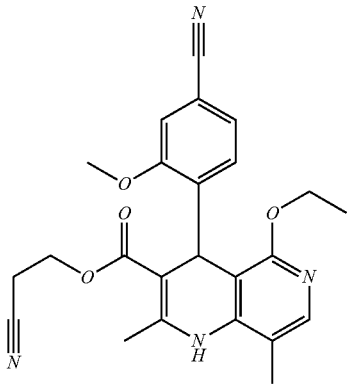
is saponified in a THF/water mixture (2:1, 9-fold) with aqueous sodium hydroxide solution to give the compound of the formula (XII)
(XII)
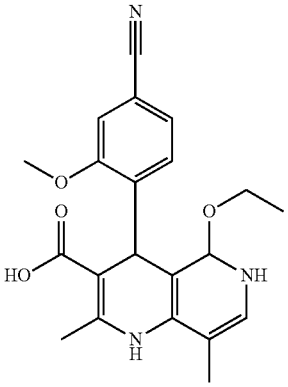
(XII)
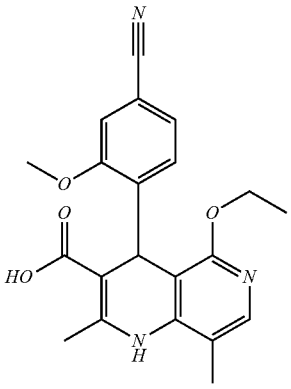

and that the compound of the formula (XII)

(XII)

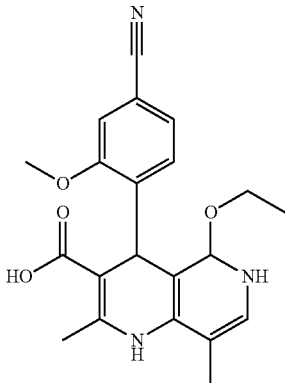

(XII)

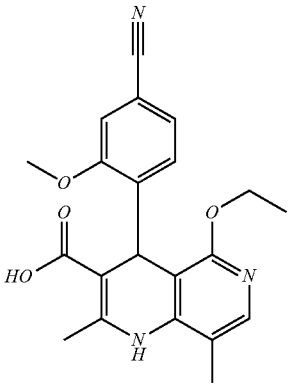

is reacted in a one-pot reaction in THF firstly with carbodiimidazole and catalytic amounts of 4-(dimethylamino) pyridine, in a second step is heated under reflux together with hexamethyldisilazane for 16 to 24 hours and in a third step is hydrolysed in water with THF or water to give the compound of the formula (XIII)

(XIII)

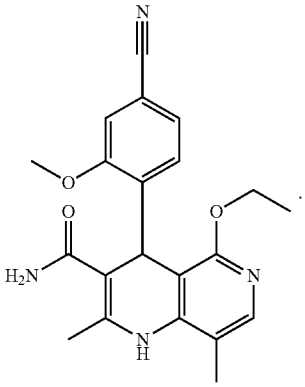

The present invention further provides a process for preparing compound of the formula (I), characterized in that the compound of the formula (XIV) or the formula (XIVa)

(XIV)

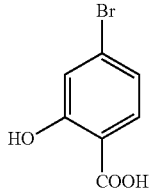

(XIVa)

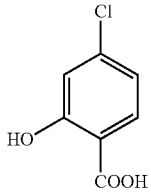

are reacted by addition of dimethyl sulphate to give the compound of the formula (XV) or (XVa)

(XV)

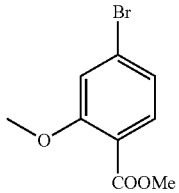

(XVa)

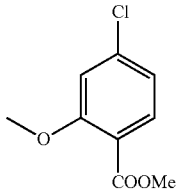

and the non-isolated methyl esters of the formula (XV) or (XVa) are reduced with 1.21 eq of REDAL (sodium bis(2-methoxyethoxy)aluminium dihydride and 1.28 eq of N-methylpiperazine to give the aldehyde of the formula (XVI) or (XVIa)

(XVI)

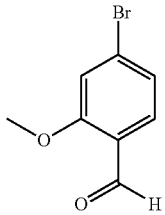

(XVIa)

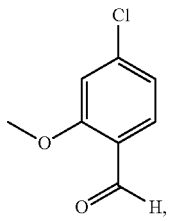

and the aldehyde (XVI) or (XVIa) is reacted further without isolation to give the nitrile of the formula (VI)

(VI)

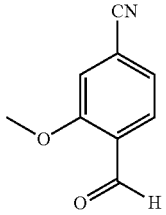

and the compound of the formula (VI)

(VI)

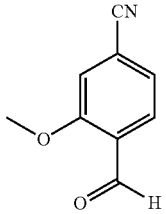

dissolved in isopropanol (3-7 fold), 5-10 mol % of piperidine and 5-10 mol % of glacial acetic acid at 30° C. is reacted with the compound of the formula (VII)

(VII)

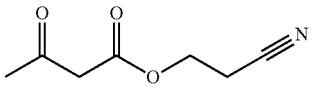

to give the compounds (VIIIa+b)

(VIII a+b)

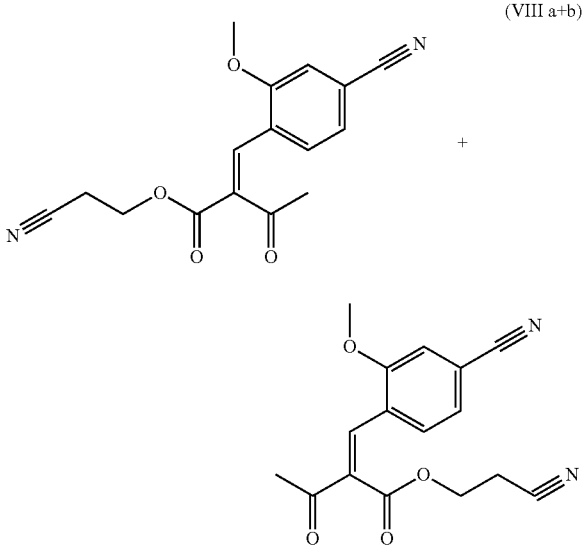

and that the compound of the formula (X)

(X)

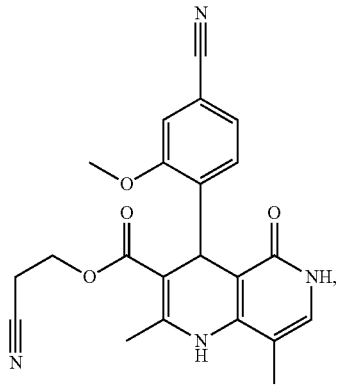

is reacted while stirring with 2.5-5 eq of triethyl orthoacetate in dimethylacetamide at 100 to 120° C. for 1.5 to 3 hours to give the compound of the formula (XI)

(XI)

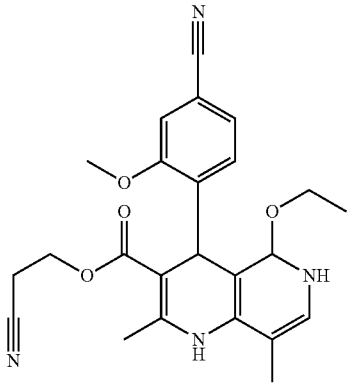

(XI)

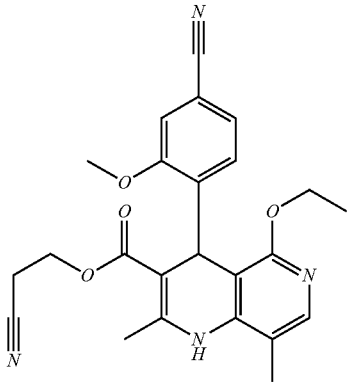

and that the compound of the formula (XI)

(XI)

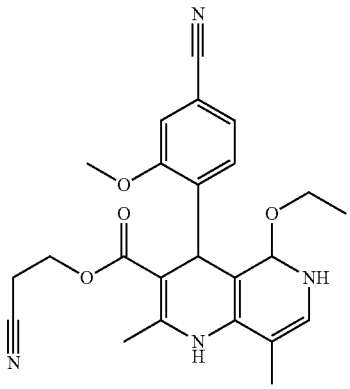

(XI)

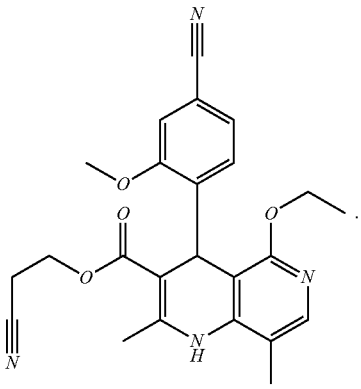

is saponified in a THF/water mixture (2:1, 9-fold) with aqueous sodium hydroxide solution to give the compound of the formula (XII)

(XII)

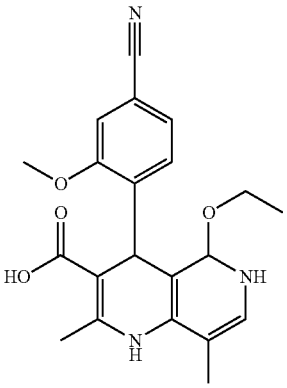

-continued (XII)

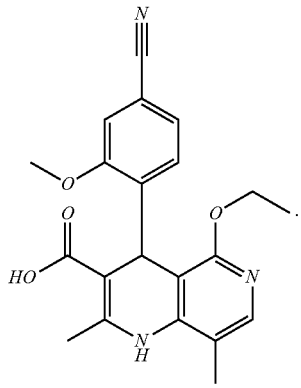

The present invention further provides a process for preparing compound of the formula (I), characterized in that the compound of the formula (VI)

(VI)

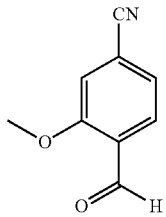

dissolved in isopropanol (3-7 fold), 5-10 mol % of piperidine and 5-10 mol % of glacial acetic acid at 30° C. is reacted with the compound of the formula (VII)

(VII)

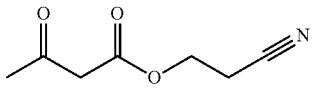

to give the compounds (VIIIa+b)

(VIII a + b)

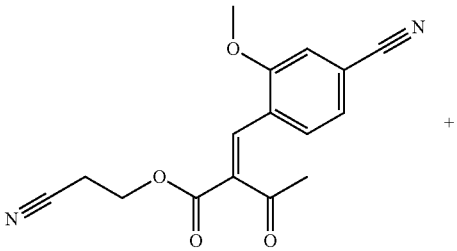

-continued

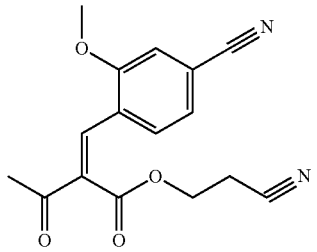

and that the compound of the formula (X)

(X)

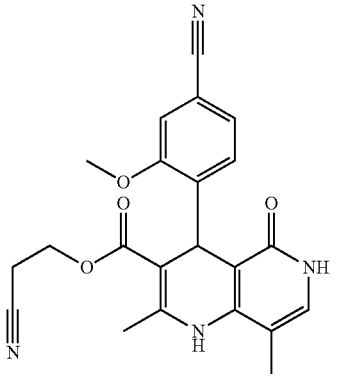

is reacted while stirring with 2.5-5 eq of triethyl orthoacetate in dimethylacetamide at 100 to 120° C. for 1.5 to 3 hours to give the compound of the formula (XI)

[ (XI)

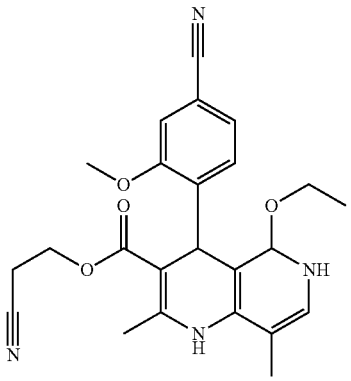

]

-continued (XI)

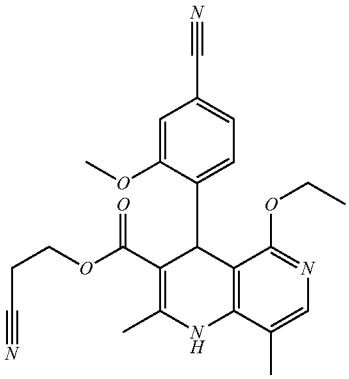

and that the compound of the formula (XI)

[ (XI)

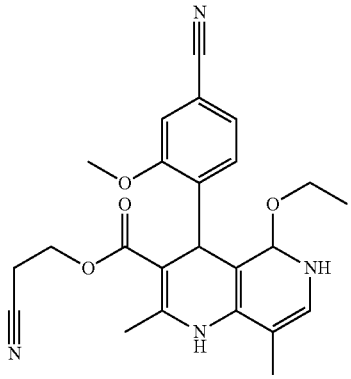

]

(XI)

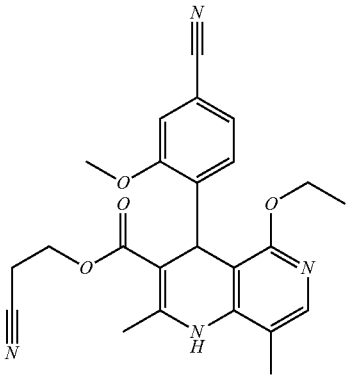

is saponified in a THF/water mixture (2:1, 9-fold) with aqueous sodium hydroxide solution to give the compound of the formula (XII)

[ (XII)

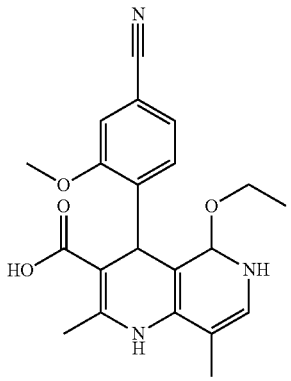

]

(XII)

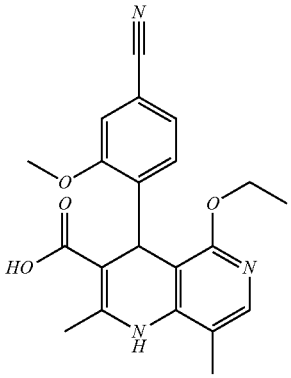

and that the compound of the formula (XII)

[ (XII)

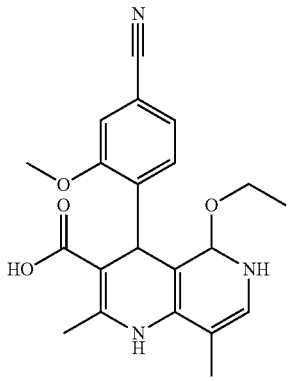

]

-continued (XII)

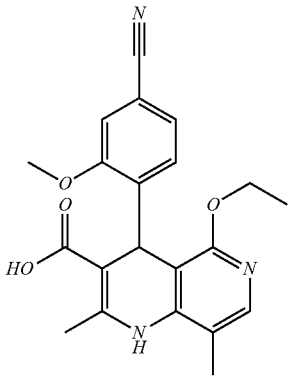

is reacted in a one-pot reaction in THF firstly with carbodiimidazole and catalytic amounts of 4-(dimethylamino) pyridine, in a second step is heated under reflux together with hexamethyldisilazane for 16 to 24 hours and in a third step is hydrolysed in water with THF or water to give the compound of the formula (XIII)

(XIII)

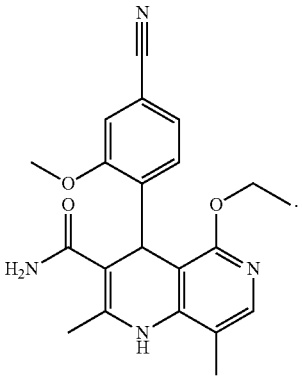

The present invention further provides a process for preparing compound of the formula (I), characterized in that the compound of the formula (XIV) or the formula (XIVa)

(XIV)

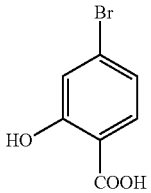

(XIVa)

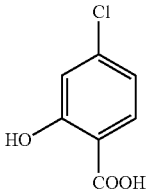

are reacted by addition of dimethyl sulphate to give the compound of the formula (XV) or (XVa)

(XV)

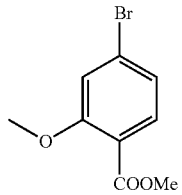

(XVa)

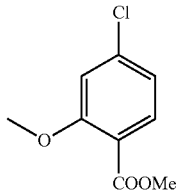

and the non-isolated methyl esters of the formula (XV) or (XVa) are reduced with 1.21 eq of REDAL (sodium bis(2-methoxyethoxy)aluminium dihydride and 1.28 eq of N-methylpiperazine to give the aldehyde of the formula (XVI) or (XVIa)

(XVI)

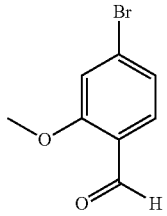

(XVIa)

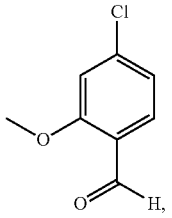

and the aldehyde (XVI) or (XVIa) is reacted further without isolation to give the nitrile of the formula (VI)

(VI)

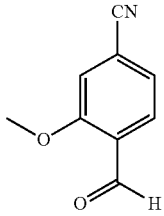

and the compound of the formula (VI)

(VI)

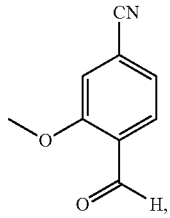

dissolved in isopropanol (3-7 fold), 5-10 mol % of piperidine and 5-10 mol % of glacial acetic acid at 30° C. is reacted with the compound of the formula (VII)

(VII)

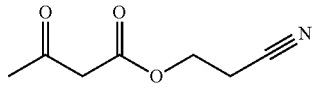

to give the compounds (VIIIa+b)

(VIII a + b)

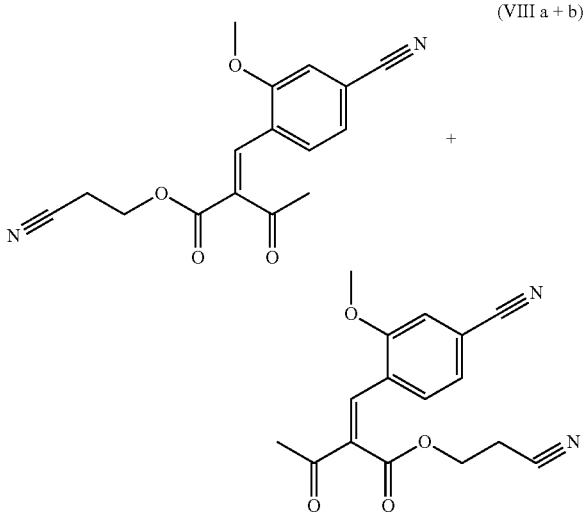

and that the compound of the formula (X)

(X)

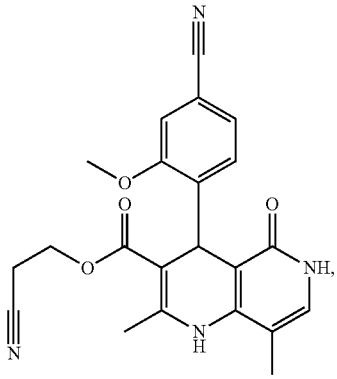

is reacted while stirring with 2.5-5 eq of triethyl orthoacetate in dimethylacetamide at 100 to 120° C. for 1.5 to 3 hours to give the compound of the formula (XI)
(XI)
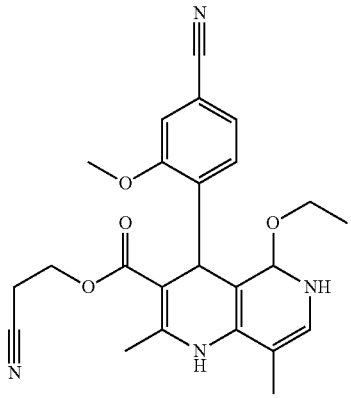
(I)
(XI)
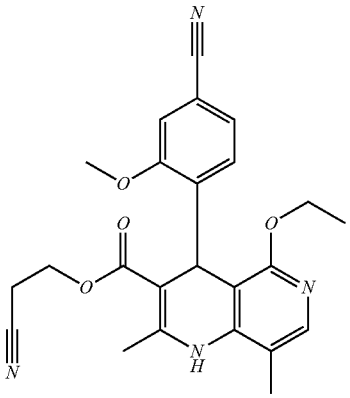
and that the compound of the formula (XI)
(XI)
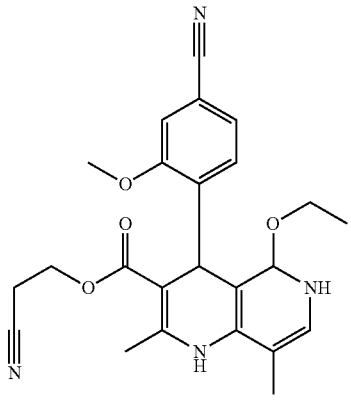
-continued
(XI)
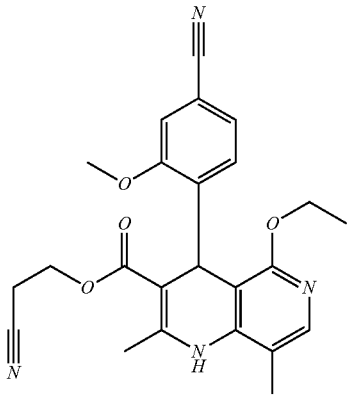
is saponified in a THF/water mixture (2:1, 9-fold) with aqueous sodium hydroxide solution to give the compound of the formula (XII)
(XII)
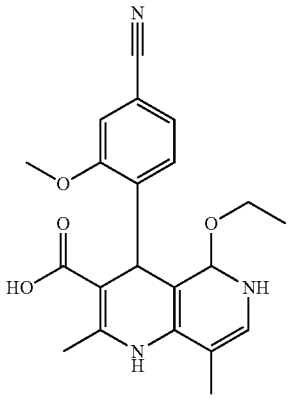
(XII)
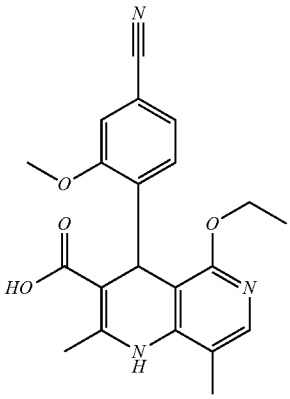

and that the compound of the formula (XII)

(XII)

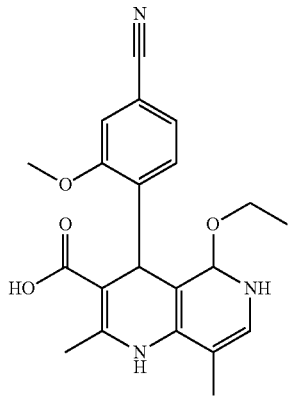

(XII)

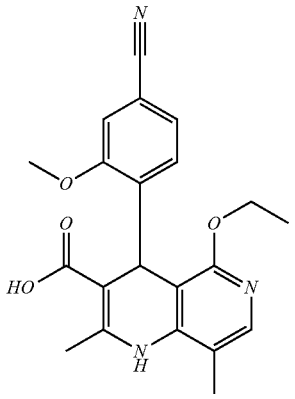

is reacted in a one-pot reaction in THF firstly with carbodiimidazole and catalytic amounts of 4-(dimethylamino) pyridine, in a second step is heated under reflux together with hexamethyldisilazane for 16 to 24 hours and in a third step is hydrolysed in water with THF or water to give the compound of the formula (XIII)

(XIII)

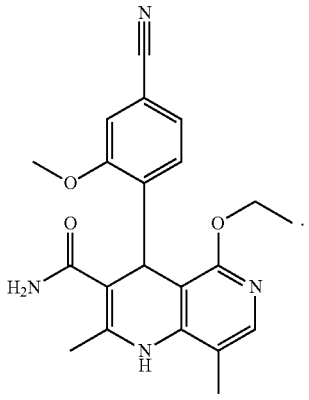

The crystallization process is very robust and affords the compound of the formula I in crystalline form of polymorph I in a reproducible manner (m.p. 252° C.). Surprisingly, it is also possible to use material with lower optical purities in the crystallization process and it was shown that even a material of 93% e.e. still gives rise after crystallization to >99% e.e.

The compound of the formula (I) is generally micronized and to be formulated into the pharmaceutical. It is found that the compound of the formula (I) in crystalline form of polymorph I has very good stability properties (even at high atmospheric humidity) and can be stored without any problem for >2 years.

With the novel synthesis according to the invention, it is possible to prepare the compound of the formula (I) in a very efficient manner. The process offers considerable advantages compared to the prior art relating to scalability and technical performance. The overall yield is significantly higher compared to published data and excellent purities of the active ingredient are also achieved. The novel process enables the reproducible, economic preparation of the defined compound of the formula (I) in crystalline form of polymorph I, of which the existence in the prior art has nowhere been described.

Using the process according to the invention presented here, 200 kg of material has already been successfully prepared for clinical trials.

The compounds according to the invention, the compound of the formula (I) and of which the compound of the formula (I) in crystalline form of polymorph I act as antagonists of the mineralocorticoid receptor and exhibit an unforeseeable, useful spectrum of pharmacological activity. They are therefore suitable for use as medicaments for treatment and/or prophylaxis of disorders in humans and animals.

The inventive compounds are suitable for the prophylaxis and/or treatment of various disorders and disease-related conditions, especially of disorders characterized either by an increase in the aldosterone concentration in the plasma or by a change in the aldosterone plasma concentration relative to the renin plasma concentration, or associated with these changes. Examples include: idiopathic primary hyperaldosteronism, hyperaldosteronism associated with adrenal hyperplasia, adrenal adenomas and/or adrenal carcinomas, hyperaldosteronism associated with cirrhosis of the liver, hyperaldosteronism associated with heart failure, and (relative) hyperaldosteronism associated with essential hypertension.

The inventive compounds are also suitable, because of their mechanism of action, for the prophylaxis of sudden cardiac death in patients at increased risk of dying of sudden cardiac death. In particular, these are patients who suffer, for example, from any of the folllowing disorders: primary and secondary hypertension, hypertensive heart disease with or without congestive heart failure, treatment-resistant hypertension, acute and chronic heart failure, coronary heart disease, stable and unstable angina pectoris, myocardial ischaemia, myocardial infarction, dilative cardiomyopathies, inherited primary cardiomyopathies, for example Brugada syndrome, cardiomyopathies caused by Chagas disease, shock, arteriosclerosis, atrial and ventricular arrhythmia, transient and ischaemic attacks, stroke, inflammatory cardiovascular disorders, peripheral and cardiac vascular disorders, peripheral blood flow disturbances, arterial occlusive disorders such as intermittent claudication, asymptomatic left-ventricular dysfunction, myocarditis, hypertrophic changes to the heart, pulmonary hypertension, spasms of the coronary arteries and peripheral arteries, thromboses, thromboembolic disorders, and vasculitis.

The inventive compounds can also be used for the prophylaxis and/or treatment of edema formation, for example pulmonary oedema, renal oedema or heart failure-related oedema, and of restenoses such as following thrombolysis therapies, percutaneous transluminal angioplasties (PTA) and percutaneous transluminal coronary angioplasties (PTCA), heart transplants and bypass operations.

The inventive compounds are further suitable for use as a potassium-saving diuretic and for electrolyte disturbances, for example hypercalcaemia, hypernatraemia or hypokalaemia.

The inventive compounds are equally suitable for treatment of renal disorders, such as acute and chronic renal failure, hypertensive renal disease, arteriosclerotic nephritis (chronic and interstitial), nephrosclerosis, chronic renal insufficiency and cystic renal disorders, for prevention of renal damage which can be caused, for example, by immunosuppressives such as cyclosporin A in the case of organ transplants, and for renal cancer.

The inventive compounds can additionally be used for the prophylaxis and/or treatment of diabetes mellitus and diabetic sequelae, for example neuropathy and nephropathy.

The inventive compounds can also be used for the prophylaxis and/or treatment of microalbuminuria, for example caused by diabetes mellitus or high blood pressure, and of proteinuria.

The inventive compounds are also suitable for the prophylaxis and/or treatment of disorders associated either with an increase in the plasma glucocorticoid concentration or with a local increase in the concentration of glucocorticoids in tissue (e.g. of the heart). Examples include: adrenal dysfunctions leading to overproduction of glucocorticoids (Cushing's syndrome), adrenocortical tumours with resulting overproduction of glucocorticoids, and pituitary tumours which autonomously produce ACTH (adrenocorticotropic hormone) and thus lead to adrenal hyperplasias with resulting Cushing's disease.

The inventive compounds can additionally be used for the prophylaxis and/or treatment of obesity, of metabolic syndrome and of obstructive sleep apnoea.

The inventive compounds can also be used for the prophylaxis and/or treatment of inflammatory disorders caused for example by viruses, spirochetes, fungi, bacteria or mycobacteria, and of inflammatory disorders of unknown etiology, such as polyarthritis, lupus erythematosus, peri- or polyarteritis, dermatomyositis, scleroderma and sarcoidosis.

The inventive compounds can further be employed for the treatment of central nervous disorders such as depression, states of anxiety and chronic pain, especially migraine, and for neurodegenerative disorders such as Alzheimer's disease and Parkinson's syndrome.

The inventive compounds are also suitable for the prophylaxis and/or treatment of vascular damage, for example following procedures such as percutaneous transluminal coronary angioplasty (PTCA), implantation of stents, coronary angioscopy, reocclusion or restenosis following bypass operations, and for endothelial dysfunction, for Raynaud's disease, for thromboangiitis obliterans (Buerger' s syndrome) and for tinnitus syndrome.

The present invention further provides for the use of the compounds according to the invention for treatment and/or prevention of disorders, especially the aforementioned disorders.

The present invention further provides for the use of the compounds according to the invention for producing a medicament for the treatment and/or prevention of disorders, in particular the disorders mentioned above.

The present invention further provides a process for treatment and/or prevention of disorders, in particular the disorders mentioned above, using an effective amount of at least one of the compounds according to the invention.

The compounds according to the invention can be used alone or, if required, in combination with other active compounds. The present invention furthermore provides medicaments containing at least one of the compounds according to the invention and one or more further active compounds, in particular for treatment and/or prevention of the abovementioned disorders. Preferred examples of active compounds suitable for combinations include:

- active compounds which lower blood pressure, for example and with preference from the group of calcium antagonists, angiotensin AII antagonists, ACE inhibitors, endothelin antagonists, renin inhibitors, alpha-receptor blockers, beta-receptor blockers and Rho kinase inhibitors;
- diuretics, especially loop diuretics, and thiazides and thiazide-like diuretics;
- antithrombotic agents, by way of example and with preference from the group of the platelet aggregation inhibitors, the anticoagulants or the profibrinolytic substances;
- active compounds altering lipid metabolism, for example and with preference from the group of the thyroid receptor agonists, cholesterol synthesis inhibitors such as, by way of example and preferably, HMG-CoA reductase inhibitors or squalene synthesis inhibitors, the ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists;
- organic nitrates and NO donors, for example sodium nitroprusside, nitroglycerin, isosorbide mononitrate, isosorbide dinitrate, molsidomine or SIN-I, and inhaled NO;
- compounds having a positive inotropic effect, for example cardiac glycosides (digoxin), beta-adrenergic and dopaminergic agonists such as isoproterenol, adrenaline, noradrenaline, dopamine and dobutamine;
- compounds which inhibit the degradation of cyclic guanosine monophosphate (cGMP) and/or cyclic adenosine monophosphate (cAMP), for example inhibitors of phosphodiesterases (PDE) 1, 2, 3, 4 and/or 5, especially PDE 5 inhibitors such as sildenafil, vardenafil and tadalafil, and PDE 3 inhibitors such as amrinone and milrinone;
- natriuretic peptides, for example "atrial natriuretic peptide" (ANP, anaritide), "B-type natriuretic peptide" or "brain natriuretic peptide" (BNP, nesiritide), "C-type natriuretic peptide" (CNP) and urodilatin;
- calcium sensitizers, a preferred example being levosimendan;
- NO-independent but haem-dependent stimulators of guanylate cyclase, such as especially the compounds described in WO 00/06568, WO 00/06569, WO 02/42301 and WO 03/095451;
- NO- and haem-independent activators of guanylate cyclase, such as especially the compounds described in WO 01/19355, WO 01/19776, WO 01/19778, WO 01/19780, WO 02/070462 and WO 02/070510;
- inhibitors of human neutrophil elastase (HNE), for example sivelestat or DX-890 (Reltran);
- compounds which inhibit the signal transduction cascade, for example tyrosine kinase inhibitors, especially sorafenib, imatinib, gefitinib and erlotinib; and/or compounds which influence the energy metabolism of the heart, preferred examples being etomoxir, dichloroacetate, ranolazine or trimetazidine.

In a preferred embodiment of the invention, the compounds according to the invention are administered in combination with a diuretic, by way of example and with preference furosemide, bumetanide, torsemide, bendroflumethiazide, chlorthiazide, hydrochlorthiazide, hydroflumethiazide, methyclothiazide, polythiazide, trichlormethiazide, chlorthalidone, indapamide, metolazone, quinethazone, acetazolamide, dichlorphenamide, methazolamide, glycerol, isosorbide, mannitol, amiloride or triamterene.

Agents which lower blood pressure are preferably understood to mean compounds from the group of calcium antagonists, angiotensin AII antagonists, ACE inhibitors, endothelin antagonists, renin inhibitors, alpha-receptor blockers, beta-receptor blockers, Rho kinase inhibitors, and the diuretics.

In a preferred embodiment of the invention, the compounds according to the invention are administered in combination with a calcium antagonist, by way of example and with preference nifedipine, amlodipine, verapamil or diltiazem.

In a preferred embodiment of the invention, the inventive compounds are administered in combination with an angiotensin AII antagonist, preferred examples being losartan, candesartan, valsartan, telmisartan or embusartan.

In a preferred embodiment of the invention, the compounds according to the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds according to the invention are administered in combination with an endothelin antagonist, by way of example and with preference bosentan, darusentan, ambrisentan or sitaxsentan.

In a preferred embodiment of the invention, the inventive compounds are administered in combination with a renin inhibitor, preferred examples being aliskiren, SPP-600, SPP-635, SPP-676, SPP-800 or SPP-1148.

In a preferred embodiment of the invention, the compounds according to the invention are administered in combination with an alpha-1-receptor blocker, by way of example and with preference prazosin.

In a preferred embodiment of the invention, the compounds according to the invention are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with a rho kinase inhibitor, by way of example and with preference fasudil, Y-27632, SLx-2119, BF-66851, BF-66852, BF-66853, KI-23095 or BA-1049.

Antithrombotic agents (antithrombotics) are preferably understood to mean compounds from the group of platelet aggregation inhibitors, of anticoagulants or of profibrinolytic substances.

In a preferred embodiment of the invention, the compounds according to the invention are administered in combination with a platelet aggregation inhibitor, by way of example and with preference aspirin, clopidogrel, ticlopidine or dipyridamole.

In a preferred embodiment of the invention, the compounds according to the invention are administered in combination with a thrombin inhibitor, by way of example and with preference ximelagatran, melagatran, bivalirudin or clexane.

In a preferred embodiment of the invention, the compounds according to the invention are administered in combination with a GPIIb/IIIa antagonist, by way of example and with preference tirofiban or abciximab.

In a preferred embodiment of the invention, the compounds according to the invention are administered in combination with a factor Xa inhibitor, by way of example and with preference rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist, by way of example and with preference coumarin.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and the lipoprotein(a) antagonists.

In a preferred embodiment of the invention, the compounds according to the invention are administered in combination with a CETP inhibitor, by way of example and with preference torcetrapib (CP-529 414), JJT-705, BAY 60-5521, BAY 78-7499 or CETP vaccine (Avant).

In a preferred embodiment of the invention, the compounds according to the invention are administered in combination with a thyroid receptor agonist, by way of example and with preference D-thyroxin, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of statins, by way of example and with preference lovastatin, simvastatin, pravastatin, fluvastatin, atorvastatin, rosuvastatin, cerivastatin or pitavastatin.

In a preferred embodiment of the invention, the compounds according to the invention are administered in combination with a squalene synthesis inhibitor, by way of example and with preference BMS-188494 or TAK-475.

In a preferred embodiment of the invention, the compounds according to the invention are administered in combination with an ACAT inhibitor, by way of example and with preference avasimibe, melinamide, pactimibe, eflucimibe or SMP-797.

In a preferred embodiment of the invention, the compounds according to the invention are administered in combination with an MTP inhibitor, by way of example and with preference implitapide, BMS-201038, R-103757 or JTT-130.

In a preferred embodiment of the invention, the compounds according to the invention are administered in combination with a PPAR-gamma agonist, by way of example and with preference pioglitazone or rosiglitazone.

In a preferred embodiment of the invention, the inventive compounds are administered in combination with a PPAR-delta agonist, preferred examples being GW-501516 or BAY 68-5042.

In a preferred embodiment of the invention, the compounds according to the invention are administered in combination with a cholesterol absorption inhibitor, by way of example and with preference ezetimibe, tiqueside or pamaqueside.

In a preferred embodiment of the invention, the compounds according to the invention are administered in combination with a lipase inhibitor, by way of example and with preference orlistat.

In a preferred embodiment of the invention, the compounds according to the invention are administered in combination with a polymeric bile acid adsorbent, by way of example and with preference cholestyramine, colestipol, colesolvam, CholestaGel or colestimide. In a preferred embodiment of the invention, the compounds according to the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds according to the invention are administered in combination with a lipoprotein(a) antagonist, by way of example and with preference gemcabene calcium (CI-1027) or nicotinic acid.

The present invention further provides medicaments which comprise at least one compound according to the invention, typically together with one or more inert, non-toxic, pharmaceutically suitable excipients, and the use thereof for the aforementioned purposes.

The compounds according to the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds according to the invention can be administered in suitable administration forms for these administration routes.

Suitable administration forms for oral administration are those which work according to the prior art and release the compounds according to the invention rapidly and/or in a modified manner and which contain the compounds according to the invention in crystalline and/or amorphized and/or dissolved form, for example tablets (uncoated or coated tablets, for example with gastric juice-resistant or retarded-dissolution or insoluble coatings which control the release of the compound according to the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Oral and parenteral administration are preferred, especially oral and intravenous administration.

The compounds according to the invention can be converted to the administration forms mentioned. This can be accomplished in a manner known per se by mixing with inert, non-toxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavour and/or odour correctants.

In general, it has been found to be advantageous in the case of parenteral administration to administer amounts of from about 0.001 to 1 mg/kg, preferably about 0.01 to 0.5 mg/kg, of body weight to achieve effective results. In the case of oral administration the dosage is about 0.01 to 100 mg/kg, preferably about 0.01 to 20 mg/kg and very particularly preferably 0.1 to 10 mg/kg of body weight.

It may nevertheless be necessary where appropriate to deviate from the stated amounts, specifically as a function of body weight, route of administration, individual response to the active compound, nature of the preparation and time or interval over which administration takes place. Thus, in some cases less than the abovementioned minimum amount may be sufficient, while in other cases the upper limit mentioned must be exceeded. In the case of administration of greater amounts, it may be advisable to divide them into several individual doses over the day.

The working examples which follow illustrate the invention. The invention is not restricted to the examples.

Unless stated otherwise, the percentages in the tests and examples which follow are percentages by weight; parts are parts by weight. Solvent ratios, dilution ratios and concentration data for the liquid/liquid solutions are in each case based on volume.

EXPERIMENTAL PART

Abbreviations and Acronyms

MS: mass from mass spectrometry

HPLC: high-performance liquid chromatography

DMF: dimethylformamide

Red-A1 solution in toluene: sodium bis(2-methoxyethoxy) aluminium dihydride in toluene THF: tetrahydrofuran Aqu. HCl: aqueous hydrochloric acid DMAP: 4-(dimethylamino)pyridine

EXAMPLES

Example 1

Methyl 4-bromo-2-methoxybenzoate (XV)

3.06 kg (22.12 mol) of potassium carbonate are initially charged in 3.6 l of acetone and heated to reflux. To this suspension are added 1.2 kg of 4-bromo-2-hydroxybenzoic acid (5.53 mol), suspended in 7.8 l of acetone and is further rinsed with 0.6 l of acetone. The suspension is heated under reflux for 1 hour (vigorous evolution of gas!). 2.65 kg (21.01 mol) of dimethyl sulphate are then added over 4 hours while boiling. The mixture is subsequently stirred under reflux for 2.5 hours. The solvent is largely distilled off (to the point of stirrability) and 12 l of toluene are added and the residual acetone is then distilled off at 110° C. About 3 l of distillate are distilled off, this being supplemented by addition of a further 3 l of toluene to the mixture. The mixture is allowed to cool to 20° C. and 10.8 l of water are added and vigorously stirred in. The organic phase is separated off and the aqueous phase is extracted once more with 6.1 l of toluene. The combined organic phases are washed with 3 l of saturated sodium chloride solution and the toluene phase is concentrated to ca. 4 l. Determination of the content by evaporation of a portion results in a converted yield of 1.306 kg (96.4% of theory). The solution is used directly in the subsequent stage.

HPLC method A: RT ca. 11.9 min.

MS (EIpos): m/z=245 $[M+H]^+$ $^1$H NMR (400 MHz, $CD_2Cl_2$): δ=3.84 (s, 3H), 3.90 (s, 3H), 7.12-7.20 (m, 2H), 7.62 (d, 1H).

Example 2

4-Bromo-2-methoxybenzaldehyde (XVI)

1.936 kg (6.22 mol) of a 65% Red-A1 solution in toluene is charged with 1.25 l of toluene at −5° C. To this solution is added 0.66 kg (6.59 mol) of 1-methylpiperazine, which is rinsed with 150 ml of toluene, keeping the temperature between −7 and −5° C. The mixture is then allowed to stir at 0° C. for 30 minutes. This solution is then added to a solution of 1.261 kg (5.147 mol) of methyl 4-bromo-2-methoxybenzoate (XV), dissolved in 4 l of toluene, keeping the temperature at −8 to 0° C. After further rinsing twice with 0.7 l of toluene, the mixture is then stirred at 0° C. for 1.5 hours. For the work-up, the solution is added to cold aqueous sulphuric acid at 0° C. (12.5 l of water+1.4 kg of conc. sulphuric acid). The temperature should increase at maximum to 10° C. (slow addition). The pH is adjusted to pH 1, if necessary, by addition of further sulphuric acid. The organic phase is separated off and the aqueous phase is extracted with 7.61 of toluene. The combined organic phases are washed with 5.1 l of water and then substantially concentrated and the residue taken up in 10 l of DMF. The solution is again concentrated to a volume of ca. 5 l. Determination of the content by evaporation of a portion results in a converted yield of 1.041 kg (94.1% of theory). The solution is used directly in the subsequent stage.

HPLC method A: RT ca. 12.1 min.

MS (EIpos): m/z=162 $[M+H]^+$ $^1$H-NMR ($CDC_3$, 400 MHz): δ=3.93 (3H, s), 7.17 (2H, m), 7.68 (1H, d), 10.40 (1H, s)

Example 3

4-Formyl-3-methoxybenzonitrile (VI)

719 g (3.34 mol) of 4-bromo-2-methoxybenzaldehyde (XVI) as a solution in 4.5 l of DMF are charged with 313 g (0.74 mol) of potassium hexacyanoferrate ($K_4[Fe(CN)_6]$) and 354 g (3.34 mol) of sodium carbonate and a further 1.2 l of DMF and 3.8 g (0.017 mol) of palladium acetate are added. The mixture is stirred at 120° C. for 3 hours. The mixture is allowed to cool to 20° C. and 5.7 l of water is added to the mixture. The mixture is extracted with 17 l of ethyl acetate and the aqueous phase washed once more with 17 l of ethyl acetate. The organic phases are combined and substantially concentrated, taken up in 5 l of isopropanol and concentrated to ca. 2 l. The mixture is heated to boiling and 2 l of water added dropwise. The mixture is allowed to cool to 50° C. and 2 l of water added anew. The mixture is cooled to 3° C. and stirred at this temperature for one hour. The product is filtered off and washed with water (2 times 1.2 l). The product is dried at 40° C. under vacuum.

Yield: 469 g (87% of theory) of a beige solid.

HPLC method A: RT ca. 8.3 min.

MS (EIpos): m/z=162 [M+H]+

1H-NMR (300 MHz, DMSO-d6): δ=3.98 (s, 3H), 7.53 (d, 1H), 7.80 (s, 1H), 7.81 (d, 1H), 10.37 (s, 1H).

Example 4

2-Cyanoethyl 4-(4-cyano-2-methoxyphenol)-2,8-dimethyl-5-oxo-1,4,5,6-tetrahydro-1,6-naphthyridin-3-carboxylate (X)

Variant A 1.035 kg (6.422 mol) of 4-formyl-3-methoxybenzonitrile (VI), 1.246 kg (8.028 mol) of 2-cyanoethyl 3-oxobutanoate, 54.6 g (0.642 mol) of piperidine and 38.5 g (0.642 mol) of glacial acetic acid are heated under reflux in 10 l of dichloromethane for 6.5 hours on a water separator. The mixture is allowed to cool to room temperature and the organic phase is washed twice with 5 l of water each time. The dichloromethane phase is then concentrated at atmospheric pressure and the still stirrable residue is taken up in 15.47 kg of 2-butanol and 0.717 kg (5.78 mol) of 4-amino-5-methylpyridone is added. The residual dichloromethane is distilled off until an internal temperature of 98° C. is reached. The mixture is subsequently heated under reflux for 20 hours. The mixture is cooled to 0° C., allowed to stir at this temperature for 4 hours and the product is filtered off. The product is dried at 40° C. under vacuum under entraining gas.

Yield: 2.049 kg (87.6% of theory based on 4-amino-5-methylpyridone, since this component is used substoichiometrically) of a pale yellow solid.

HPLC method A: RT ca. 9.7 min.

MS (EIpos): m/z=405 $[M+H]^+$ $^1$H-NMR (300 MHz, DMSO-$d_6$): δ=2.03 (s, 3H), 2.35 (s, 3H), 2.80 (m, 2H), 3.74 (s, 3H), 4.04 (m, 1H), 4.11 (m, 1H), 5.20 (s, 1H), 6.95 (s, 1H), 7.23 (dd, 1H), 7.28-7.33 (m, 2H), 8.18 (s, 1H), 10.76 (s, 1H).

Variant B 1.344 kg (8.34 mol) of 4-formyl-3-methoxybenzonitrile (VI), 71 g (0.834 mol) of piperidine and 50.1 g (0.834 mol) of glacial acetic acid are charged in 6 l of isopropanol and at 30° C. a solution of 1.747 kg (11.26 mol) of 2-cyanoethyl 3-oxobutanoate in 670 ml of isopropanol is added over 3 hours. The mixture is then stirred at 30° C. for one hour. The mixture is cooled to 0-3° C. and stirred for 0.5 hours. The product is filtered off and washed twice with 450 ml of cold isopropanol each time. To determine the yield, the product is dried at 50° C. under vacuum (2.413 kg, 97% of theory); however, due to the high yield, the isopropanol-moist product is generally further processed directly. For this purpose, the product is taken up in 29 l of isopropanol and 1.277 kg (7.92 mol) of 4-amino-5-methylpyridone are added and then the mixture is heated to an internal temperature of 100° C. under a positive pressure of ca. 1.4 bar for 24 h in a closed vessel. The mixture is then cooled to 0° C. by means of a gradient over a period of 5 h and then stirred at 0° C. for 3 hours. The product is then filtered off and washed with 2.1 l of cold isopropanol. The product is dried at 60° C. under vacuum.

Yield: 2.819 kg (88% of theory based on 4-amino-5-methylpyridone, since this component is used substoichiometrically) of a pale yellow solid.

HPLC method A: RT ca. 9.7 min.

MS (EIpos): m/z=405 $[M+H]^+$ $^1$H-NMR (300 MHz, DMSO-$d_6$): δ=2.03 (s, 3H), 2.35 (s, 3H), 2.80 (m, 2H), 3.74 (s, 3H), 4.04 (m, 1H), 4.11 (m, 1H), 5.20 (s, 1H), 6.95 (s, 1H), 7.23 (dd, 1H), 7.28-7.33 (m, 2H), 8.18 (s, 1H), 10.76 (s, 1H).

Example 5

2-Cyanoethyl 4-(4-cyano-2-methoxyphenol)-5-ethoxy-2,8-dimethyl-1,4-dihydro-1,6-naphthyridine-3-carboxylate (XI)

2.142 kg (5.3 mol) of 2-cyanoethyl 4-(4-cyano-2-methoxyphenyl)-2,8-dimethyl-5-oxo-1,4,5,6-tetrahydro-1,6-naphthyridine-3-carboxylate (X) and 4.70 kg (29 mol) of triethyl orthoacetate are dissolved in 12.15 l of dimethylacetamide and 157.5 g of concentrated sulphuric acid are added. The mixture is heated at 115° C. for 1.5 hours and then cooled to 50° C. At 50° C., 12.15 l of water are added dropwise over 30 minutes. After completion of the addition, the mixture is seeded with 10 g of the title compound (XI) and a further 12.15 l of water are added dropwise over 30 minutes at 50° C. The mixture is cooled to 0° C. (gradient, 2 hours) and stirred at 0° C. for two hours. The product is filtered off, washed twice with 7.7 l each time of water and dried at 50° C. under vacuum.

Yield: 2114.2 g (92.2% of theory) of a pale yellow solid.

HPLC method B: RT ca. 10.2 min.

MS (EIpos): m/z=433 $[M+H]^+$ $^1$H-NMR (300 MHz, DMSO-$d_6$): δ=1.11 (t, 3H), 2.16 (s, 3H), 2.42 (s, 3H), 2.78 (m, 2H), 3.77 (s, 3H), 4.01-4.13 (m, 4H), 5.37 (s, 1H), 7.25 (d, 1H), 7.28-7.33 (m, 2H), 7.60 (s, 1H), 8.35 (s, 1H).

Alternatively, the reaction may be carried out in NMP (1-methyl-2-pyrrolidone)

2-Cyanoethyl 4-(4-cyano-2-methoxyphenyl)-5-ethoxy-2,8-dimethyl-1,4-dihydro-1,6-naphthyridine-3-carboxylate (XI)

2.142 kg (5.3 mol) of 2-cyanoethyl 4-(4-cyano-2-methoxyphenyl)-2,8-dimethyl-5-oxo-1,4,5,6-tetrahydro-1,6-naphthyridine-3-carboxylate (X) and 2.35 kg (14.5 mol) of triethyl orthoacetate are dissolved in 3.21 kg of NMP (1-methyl-2-pyrrolidone) and 157.5 g of concentrated sulphuric acid are added. The mixture is heated at 115° C. for 1.5 hours and then cooled to 50° C. At 50° C., 2.2 l of water are added dropwise over 30 minutes. After completion of the addition, the mixture is seeded with 10 g of the title compound (XI) and a further 4.4 l of water are added dropwise over 30 minutes at 50° C. The mixture is cooled to 0° C. (gradient, 2 hours) and then stirred at 0° C. for two hours. The product is filtered off, washed twice with 4 l each time of water and dried at 50° C. under vacuum.

Yield: 2180.7 g (95.1% of theory) of a pale yellow solid.

HPLC method B: RT ca. 10.2 min.

Example 6

4-(4-Cyano-2-methoxyphenyl)-5-ethoxy-2,8-dimethyl-1,4-dihydro-1,6-naphthyridine-3-carboxylic acid (XII)

2.00 kg (4.624 mol) of 2-cyanoethyl 4-(4-cyano-2-methoxyphenyl)-5-ethoxy-2,8-dimethyl-1,4-dihydro-1,6-naphthyridine-3-carboxylate (XI) are dissolved in a mixture of 12 l of THF and 6 l of water and cooled to 0° C. To this solution at 0° C. is added dropwise over 15 minutes an aqueous sodium hydroxide solution (prepared from 0.82 kg of 45% aq. NaOH (9.248 mol) and 4.23 l of water and the mixture is then stirred at 0° C. for 1.5 hours. The mixture is extracted twice with 4.8 l of methyl tert-butyl ether each time and once with 4.8 l of ethyl acetate. The aqueous solution at 0° C. is adjusted to pH 7 with dilute hydrochloric acid (prepared from 0.371 kg of 37% HCl and 1.51 l of water). The solution is allowed to warm to 20° C. and an aqueous solution of 2.05 kg of ammonium chloride in 5.54 l of water is added. The solution is stirred at 20° C. for 1 hour, the product filtered and washed twice with 1.5 l of water each time and once with 4 l of acetonitrile. The product is dried at 40° C. under entraining gas.

Yield: 1736.9 g (99% of theory) of an almost colourless powder (very light yellow tint).

HPLC method C: RT: ca. 6.8 min.

MS (EIpos): m/z=380 $[M+H]^+$ $^1$H-NMR (300 MHz, DMSO-$d_6$): δ=1.14 (t, 3H), 2.14 (s, 3H), 2.37 (s, 3H), 3.73 (s, 3H), 4.04 (m, 2H), 5.33 (s, 1H), 7.26 (m, 2H), 7.32 (s, 1H), 7.57 (s, 1H), 8.16 (s, 1H), 11.43 (br. s, 1H).

Alternative work-up using toluene for the extraction:

4-(4-Cyano-2-methoxyphenyl)-5-ethoxy-2,8-dimethyl-1,4-dihydro-1,6-naphthyridine-3-carboxylic acid (XII)

2.00 kg (4.624 mol) of 2-cyanoethyl 4-(4-cyano-2-methoxyphenyl)-5-ethoxy-2,8-dimethyl-1,4-dihydro-1,6-naphthyridine-3-carboxylate (XI) are dissolved in a mixture of 12 l of THF and 6 l of water and cooled to 0° C. To this solution at 0° C. is added dropwise over 15 minutes an aqueous sodium hydroxide solution (prepared from 0.82 kg of 45% aq. NaOH (9.248 mol) and 4.23 l of water and the mixture is then stirred at 0° C. for 1.5 hours. 5 L of toluene and 381.3 g of sodium acetate are added and stirred in vigorously. The phases are allowed to settle and the organic phase is separated. The aqueous phase is adjusted to pH 6.9 with 10% hydrochloric acid (at ca. pH 9.5 the solution is seeded with 10 g of the title compound). After precipitation of the product is complete, the mixture is stirred at 0° C. for one hour and is then filtered and washed twice with 4 l of water each time and twice with 153 ml of toluene each time. The product is dried at 40° C. under vacuum under entraining gas (nitrogen, 200 mbar. Yield: 1719.5 g (98% of theory) of an almost colourless powder (very slight yellow tint).

HPLC method C: RT: ca. 6.8 min.)

Example 7

4-(4-Cyano-2-methoxyphenol)-5-ethoxy-2,8-dimethyl-1,4-dihydro-1,6-naphthyridine-3-carboxamide (XIII)

1.60 kg (4.22 mol) of 4-(4-cyano-2-methoxyphenyl)-5-ethoxy-2,8-dimethyl-1,4-dihydro-1,6-naphthyridine-3-carboxylic acid (XII) and 958 g (5.91 mol) of 1,1-carbodiimidazole are charged in 8 l of THF and 51 g (0.417 mol) of DMAP is added at 20° C. The mixture is stirred at 20° C. (evolution of gas!) for one hour and then heated to 50° C. for 2.5 hours. 2.973 kg (18.42 mol) of hexamethyldisilazane is added to this solution and is boiled under reflux for 22 hours. A further 1.8 l of THF is added and the mixture cooled to 5° C. A mixture of 1.17 l of THF and 835 g of water is added over 3 hours such that the temperature remains between 5 and 20° C. The mixture is subsequently boiled under relux for one hour, then cooled via a gradient (3 hours) to 0° C. and stirred at this temperature for one hour. The product is filtered off and washed twice with 2.4 l of THF each time and twice with 3.2 l of water each time. The product is dried at 70° C. under vacuum under entraining gas.

Yield: 1.501 kg (94% of theory) of an almost colourless powder (very slight yellow tint).

HPLC method B: RT ca. 6.7 min.

MS (EIpos): m/z=379 $[M+H]^+$ $^1$H-NMR (300 MHz, DMSO-$d_6$): δ=1.05 (t, 3H), 2.12 (s, 3H), 2.18 (s, 3H), 3.82 (s, 3H), 3.99-4.07 (m, 2H), 5.37 (s, 1H), 6.60-6.84 (m, 2H), 7.14 (d, 1H), 7.28 (dd, 1H), 7.37 (d, 1H), 7.55 (s, 1H), 7.69 (s, 1H).

Example 8

(4S)-4-(4-Cyano-2-methoxyphenyl)-5-ethoxy-2,8-dimethyl-1,4-dihydro-1,6-naphthyridine-3-carboxamide (I) as a solution in acetonitrile/methanol 40:60

Enantiomer Separation on an SMB System

The feed solution is a solution corresponding to a concentration consisting of 50 g of racemic 4-(4-cyano-2-methoxyphenyl)-5-ethoxy-2,8-dimethyl-1,4-dihydro-1,6-naphthyridine-3-carboxamide (XIII), dissolved in 1 liter of a mixture of methanol/acetonitrile 60:40.

The solution is chromatographed by means of an SMB system on a stationary phase: Chiralpak AS-V, 20 μm. The pressure is 30 bar and a mixture of methanol/acetonitrile 60:40 is used as eluent.

9.00 kg of 4-(4-cyano-2-methoxyphenyl)-5-ethoxy-2,8-dimethyl-1,4-dihydro-1,6-naphthyridine-3-carboxamide (XII) are dissolved in 180 l of a mixture consisting of methanol/acetonitrile 60:40 and chromatographed by means of SMB. After concentrating the product-containing fractions, 69.68 liters of a 6.2% solution (corresponding to 4.32 kg of (4S)-4-(4-cyano-2-methoxyphenyl)-5-ethoxy-2,8-dimethyl-1,4-dihydro-1,6-naphthyridine-3-carboxamide (I) is obtained as a solution in acetonitrile/methanol 40:60).

Yield: 4.32 kg (48% of theory), as a colourless fraction dissolved in 69.68 liters of acetonitrile/methanol 40:60.

Enantiomeric purity: >98.5% e.e. (HPLC, method D)

A sample is concentrated under vacuum and gives: MS (EIpos): m/z=379 $[M+H]^+$ $^1$H-NMR (300 MHz, DMSO-$d_6$): δ=1.05 (t, 3H), 2.12 (s, 3H), 2.18 (s, 3H), 3.82 (s, 3H), 3.99-4.07 (m, 2H), 5.37 (s, 1H), 6.60-6.84 (m, 2H), 7.14 (d, 1H), 7.28 (dd, 1H), 7.37 (d, 1H), 7.55 (s, 1H), 7.69 (s, 1H).

Example 9

(4S)-4-(4-Cyano-2-methoxyphenyl)-5-ethoxy-2,8-dimethyl-1,4-dihydro-1,6-naphthridine-3-carboxamide (I)

Crystallization and Polymorph Adjustment 64.52 liters of a 6.2% solution from Example 8 in a mixture of acetonitrile/methanol 40:60 (corresponding to 4.00 kg of compound 1) were filtered through a filter cartridge (1.2 um) and subsequently sufficiently concentrated at 250 mbar such that the solution is still stirrable. 48 l of ethanol, denatured with toluene, was added and distilled again at 250 mbar up to the limit of stirrability (redistillation in ethanol). A further 48 l of ethanol, denatured with toluene, was added and then distilled off at atmospheric pressure down to a total volume of ca. 14 l (jacket temperature 98° C.). The mixture was cooled via a gradient (4 hours) to 0° C., stirred at 0° C. for 2 hours and the product filtered off. The product was washed twice with 4 l of cold ethanol each time and then dried at 50° C. under vacuum.

Yield: 3.64 kg (91% of theory) of a colourless crystalline powder.

Enantiomeric purity: >>99% e.e. (HPLC method D); Retention times/RRT: (4S)-4-(4-cyano-2-methoxyphenyl)-5-ethoxy-2,8-dimethyl-1,4-dihydro-16-naphthyridine-3-carboxamide (1) ca. 11 min. RRT: 1.00; (4R)-4-(4-cyano-2-methoxyphenyl)-5-ethoxy-2,8-dimethyl-1,4-dihydro-1,6-naphthyridine-3-carboxamide (I) ca. 9 min. RRT: 0.82

Purity: >99.8% (HPLC method B), RT: ca. 6.7 min.

Content: 99.9% (relative to external standard)

specific rotation (chloroform, 589 nm, 19.7° C., c=0.38600 g/100 ml): −148.8°.

MS (EIpos): m/z=379 $[M+H]^+$ $^1$H NMR (300 MHz, DMSO-$d_6$): δ=1.05 (t, 3H), 2.12 (s, 3H), 2.18 (s, 3H), 3.82 (s, 3H), 3.99-4.07 (m, 2H), 5.37 (s, 1H), 6.60-6.84 (m, 2H), 7.14 (d, 1H), 7.28 (dd, 1H), 7.37 (d, 1H), 7.55 (s, 1H), 7.69 (s, 1H).

Melting point: 252° C. (compound of the formula (I) in crystalline form of polymorph I)

Physicochemical Characterization of Compound of the Formula (I) in Crystalline Form of Polymorph I Compound of the formula (I) in crystalline form of polymorph I melts at 252° C., ΔH=95-113 $Jg^{-1}$ (heating rate 20 $Kmin^{-1}$, FIG. 1).

A depression of the melting point was observed depending on the heating rate.

The melting point decreases at a lower heating rate (e.g. 2 $Kmin^{-1}$) since decomposition occurs.

No other phase transitions were observed. A loss of mass of ca. 0.1% was observed up to a temperature of 175° C.

Stability and Moisture Absorption

Samples of compound of the formula (I) in crystalline form of polymorph I were stored at 85% and 97% rel. humidity (25° C.). The samples were evaluated after 12 months by DSC, TGA and XRPD. After 12 months, a mass change of <0.1% is observed in both cases. This means that compound of the formula (I) in crystalline form of polymorph I shows no significant absorption of water under these storage conditions. According to DSC, TGA and XRPD, no difference exists in compound of the formula (I) in crystalline form of polymorph I.

Pharmaceutical formulation of (4S)-4-(4-cyano-2-methoxyphenyl)-5-ethoxy-2,8-dimethyl-1,4-dihydro-1,6-naphthyridine-3-carboxamide of the formula (I)

A granular solution of the compound of the formula (I) in crystalline form of polymorph I in micronized form, hypromellose 5 cP and sodium lauryl sulphate was prepared in purified water.

Microcrystalline cellulose, lactose monohydrate and croscarmellose sodium were mixed (premix) in a container or a fluidized bed granulator.

The premix and the granular solution were granulated in the fluid-bed granulator.

The lubricant magnesium stearate was added after which the granulate was dried and sieved. A ready to press mixture was thus prepared.

The ready to press mixture was compressed to give tablets using a rotary tablet press.

A homogeneous coating suspension was prepared from hypromellose, talc, titanium dioxide, yellow iron oxide, red iron oxide and purified water. The coating suspension was sprayed onto the tablets in a suitable coating device.

| Composition | Ph IIb [mg] | Ph IIb [mg] | Ph IIb [mg] | Ph IIb [mg] | Ph IIb [mg] | Ph IIb [mg] | Ph IIb [mg] |
|---|---|---|---|---|---|---|---|
| Compound of the formula (I) in polymorph I micronized | 1.25 | 2.50 | 5.00 | 7.50 | 10.00 | 15.00 | 20.00 |
| Excipients | | | | | | | |
| Microcrystalline cellulose | 73.80 | 72.50 | 69.90 | 67.30 | 64.70 | 62.00 | 59.30 |
| Croscarmellose sodium | 4.50 | 4.50 | 4.50 | 4.50 | 4.50 | 4.50 | 4.50 |
| Hypromellose 5 cP | 4.50 | 4.50 | 4.50 | 4.50 | 4.50 | 4.50 | 4.50 |
| Lactose monohydrate | 45.00 | 45.00 | 45.00 | 45.00 | 45.00 | 42.50 | 40.00 |
| Magnesium stearate | 0.90 | 0.90 | 0.90 | 0.90 | 0.90 | 0.90 | 0.90 |
| Sodium lauryl sulphate | 0.05 | 0.10 | 0.20 | 0.30 | 0.40 | 0.60 | 0.80 |
| Weight (uncoated tablet) | 130.00 | 130.00 | 130.00 | 130.00 | 130.00 | 130.00 | 130.00 |
| Film-coating | | | | | | | |
| Hypromellose 5 cP | 3.0336 | 3.0336 | 3.0336 | 3.0336 | 3.0336 | 3.0336 | 3.0336 |
| Titanium dioxide | 2.3196 | 2.3196 | 2.3196 | 2.3196 | 2.3196 | 2.3196 | 2.3196 |
| Talc | 0.6072 | 0.6072 | 0.6072 | 0.6072 | 0.6072 | 0.6072 | 0.6072 |
| Yellow iron oxide | 0.0324 | 0.0324 | 0.0324 | 0.0324 | 0.0324 | 0.0324 | 0.0324 |
| Red iron oxide | 0.0072 | 0.0072 | 0.0072 | 0.0072 | 0.0072 | 0.0072 | 0.0072 |
| Weight (film-coating) | 6.0000 | 6.0000 | 6.0000 | 6.0000 | 6.0000 | 6.0000 | 6.0000 |
| Weight (coated tablet) | 136.00 | 136.00 | 136.00 | 136.00 | 136.00 | 136.00 | 136.00 |

HPLC Conditions/Methods

Method A

YMC Hydrosphere C18
150*4.6 mm, 3.0 μm
25° C., 1 ml/min, 270 nm, 4 nm
0': 70% TFA 0.1%*; 30% acetonitrile
17': 20% TFA 0.1%*; 80% acetonitrile
18': 70% TFA 0.1%*; 30% acetonitrile
*: TFA in water Method B YMC Hydrosphere C18
150*4.6 mm, 3.0 μm
25° C., 1 ml/min., 255 nm, 6 nm
0': 90% TFA 0.1%; 10% acetonitrile
20': 10% TFA 0.1%; 90% acetonitrile
18': 10% TFA 0.1%; 90% acetonitrile Method C Nucleodur Gravity C18
150*2 mm, 3.0 μm
35° C.; 0.22 ml/min., 255 nm, 6 nm
Solution A: 0.58 g of ammonium hydrogen phosphate and 0.66 g of ammonium dihydrogen
phosphate in 1 L of water (ammonium phosphate buffer pH 7.2)
Solution B: acetonitrile
0': 30% B; 70%/A
15': 80% B; 20% A
25': 80% B; 20% A Method D Column length: 25 cm
Internal Diameter: 4.6 mm
Packing: Chiralpak IA, 5 μm
Reagents: 1. Acetonitrile HPLC grade
2. Methyl tert-butyl ether (MTBE), p.a.
Test solution The sample is dissolved at a concentration of 1.0 mg/mL
in acetonitrile.
(e.g. ca. 25 mg of sample, weighed exactly, dissolved in acetonitrile to 25.0 mL).
Eluent A. acetonitrile
B. Methyl tert-butyl ether (MTBE), p.a.
Flow rate 0.8 ml/min
Column oven temperature 25° C.
Detection measuring wavelength: 255 nm
Band width: 6 nm
Injection volumes 5 μL
Mix composition of eluents A and B in ratio by volume of 90:10
Chromatogram run time 30 min Retention times/RRT:

(4S)-4-(4-cyano-2-methoxyphenyl)-5-ethoxy-2,8-dimethyl-1,4-dihydro-1,6-naphthyridine-3-carboxamide (1) ca. 11 min. RRT: 1.00

(4R)-4-(4-cyano-2-methoxyphenyl)-5-ethoxy-2,8-dimethyl-1,4-dihydro-1,6-naphthyridine-3-carboxamide (1) ca. 9 min. RRT: 0.82

Lattice Constants of Compound of the Formula (I) in Crystalline Form of Polymorph I Polymorph I
Crystal system orthorhombic
Space group P2(1)2(1)2(1)
Molecules per unit
cell 4
Length of axis a [Å] 7.8610(3)
Length of axis b [Å] 11.7797(6)
Length of axis c [Å] 20.1792(8)
α [°] 90
β [°] 90
γ [°] 90
Calculated density at
100 K [g cm-3] 1.345

Measuring Parameters of the X-ray Diffractometry for the Measurement of Compound of the Formula (I) in Crystalline Form of Polymorph I

| | |
|---|---|
| Data set name | 2429-08a r2 |
| Scan axis | 2Theta-Omega |
| Start position [°2Th.] | 2.0000 |
| End position [°2Th.] | 37.9900 |
| Type of divergence screen | Fixed |
| Size of divergence screen [°] | 1.0000 |
| Measurement temperature [° C.] | 25 |
| Anode material | Cu |
| K-Alpha1 [Å] | 1.54060 |
| Generator setting | 35 mA, 45 kV |
| Diffractometer type | Transmission diffractometer |
| Goniometer radius [mm] | 240.00 |
| Focus-div. screen gap [mm] | 91.00 |
| Primary beam monochromator | Yes |
| Sample rotation | Yes |

| Peak maximum [2 Theta] Polymorph I |
|---|
| 8.5 |
| 11.4 |
| 11.9 |
| 13.4 |
| 14.1 |
| 14.8 |
| 15.0 |
| 15.4 |
| 16.0 |
| 17.2 |
| 18.5 |
| 19.0 |
| 19.8 |
| 20.5 |
| 20.8 |
| 22.1 |
| 22.7 |
| 23.0 |
| 23.1 |
| 23.6 |
| 23.9 |
| 24.6 |
| 24.9 |
| 25.2 |
| 25.6 |

-continued

| Peak maximum [2 Theta] Polymorph I |
|---|
| 26.0 |
| 26.5 |
| 27.1 |
| 27.3 |
| 28.3 |
| 28.5 |
| 28.8 |
| 29.6 |
| 30.1 |
| 30.6 |
| 31.5 |
| 31.9 |
| 32.4 |
| 32.9 |
| 33.1 |
| 33.4 |
| 33.7 |
| 34.5 |
| 34.7 |
| 35.0 |
| 35.8 |
| 36.2 |
| 36.5 |
| 37.2 |
| 37.4 |

Measuring Conditions for the IR and Raman Spectroscopy for the Measurement of the Compound of the Formula (I) in Crystalline Form of Polymorph I:

IR:

| | |
|---|---|
| Instrument | Perkin Elmer Spectrum One |
| Number of scans | 32 |
| Resolution | 4 $cm^{-1}$ |
| Technique | Diamond ATR unit |
| Raman: | |
| Instrument | Bruker Raman RFS 100/S |
| Number of scans | 64 |
| Resolution | 2-4 $cm^{-1}$ |
| Laser Power | 350 mW |
| Laser wavelength | 1064 nm |

| Band maximum [$cm^{-1}$] | |
|---|---|
| IR-ATR Polymorph I | Raman Polymorph I |
| 3475 | 3074 |
| 3416 | 2997 |
| 3366 | 2970 |
| 3074 | 2941 |
| 2992 | 2920 |
| 2952 | 2836 |
| 2835 | 2231 |
| 2230 | 1659 |
| 1681 | 1641 |
| 1658 | 1623 |
| 1606 | 1601 |
| 1572 | 1577 |
| 1485 | 1487 |
| 1464 | 1443 |
| 1454 | 1383 |
| 1431 | 1362 |
| 1420 | 1327 |
| 1407 | 1303 |
| 1381 | 1267 |
| 1355 | 1230 |
| 1341 | 1191 |

-continued

| Band maximum [$cm^{-1}$] | |
|---|---|
| IR-ATR Polymorph I | Raman Polymorph I |
| 1325 | 1161 |
| 1303 | 1123 |
| 1285 | 1093 |
| 1267 | 1032 |
| 1255 | 991 |
| 1229 | 883 |
| 1222 | 827 |
| 1161 | 810 |
| 1136 | 759 |
| 1097 | 734 |
| 1031 | 708 |
| 991 | 671 |
| 976 | 613 |
| 967 | 528 |
| 924 | 505 |
| 909 | 471 |
| 875 | 442 |
| 847 | 346 |
| 827 | 320 |
| 810 | 297 |
| 776 | 186 |
| 758 | 155 |
| 746 | 114 |
| 733 | |
| 723 | |
| 706 | |
| 697 | |
| 670 | |

DESCRIPTION OF THE FIGURES

FIG. 1: DSC (20 $Kmin^{-1}$) and TGA of compound of the formula (I) in crystalline form of polymorph I FIG. 2: X-ray of a single crystal of polymorph I of (4S)-4-(4-cyano-2-methoxyphenyl)-5-ethoxy-2,8-dimethyl-1,4-dihydro-1,6-naphthyridine-3-carboxamide (1)

FIG. 3: X-ray diffractogram of compound of the formula (I) in crystalline form of polymorph I FIG. 4: Raman spectrum of compound of the formula (I) in crystalline form of polymorph I FIG. 5: FT-Infrared (IR) spectrum (KBr) of compound of the formula (I) in crystalline form of polymorph I FIG. 6: FT-Infrared (IR) spectrum (ATR) of compound of the formula (I) in crystalline form of polymorph I FIG. 7: FT-Near-infrared (NIR) spectrum of compound of the formula (I) in crystalline form of polymorph I FIG. 8: FT-Far-infrared (FIR) spectrum of compound of the formula (I) in crystalline form of polymorph I FIG. 9: Solid state $^{13}C$-NMR spectrum of compound of the formula (I) in crystalline form of polymorph I FIG. 10: Stability of compound of the formula (I) in crystalline form of polymorph I in air humidity (x-axis % relative humidity/y-axis weight change in %

The invention claimed is:

1. A process for preparing a compound of formula (VI)

(VI)

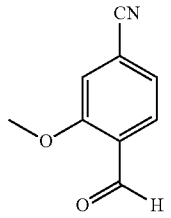

comprising reacting a compound of formula (XIV) or formula (XIVa)

(XIV)

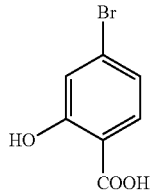

(XIVa)

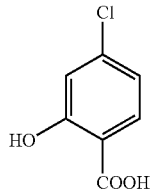

with dimethyl sulphate to give a compound of formula (XV) or (XVa)

(XV)

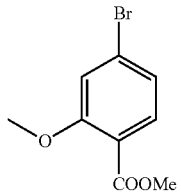

(XVa)

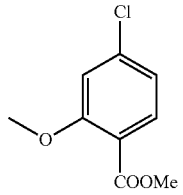

reducing the non-isolated methyl esters of the formula (XV) or (XVa) with 1.21 equivalents of REDAL (sodium bis(2-methoxyethoxy)aluminium dihydride) and 1.28 equivalents of N-methylpiperazine to give an aldehyde of formula (XVI) or (XVIa)

(XVI)

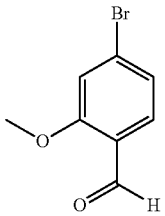

(XVIa)

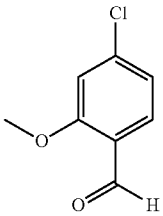

and reacting the aldehyde of formula (XVI) or (XVIa) without isolation to give the compound of formula (VI)

(VI)

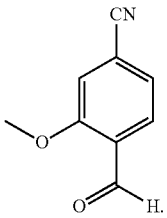

2. A process for preparing compounds of formulae [(Villa+b)] (*VIIIa+b*)

(VIII a+b)

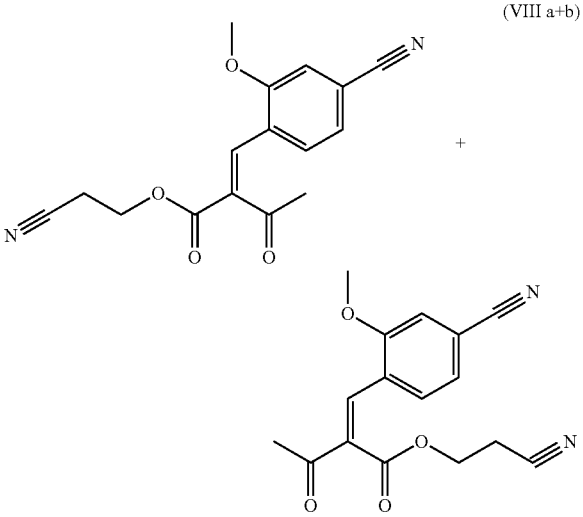

comprising dissolving a compound of formula (VI)

(VI)

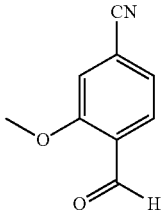

in isopropanol [(3-7 fold)] *3-7 fold*, 5-10 mol % of piperidine and 5-10 mol % of glacial acetic acid at 30° C. and reacting the dissolved compound of formula (VI) with a compound of formula (VII)

(VII)

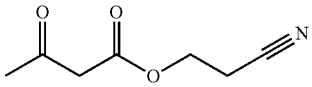

to give the compounds of formulae (VIII a+b)

(VIII a+b)

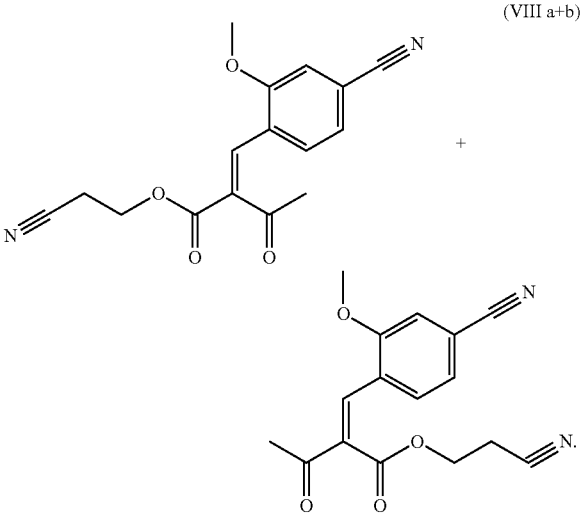

3. A process for preparing a compound of formula (XI)

(XI)

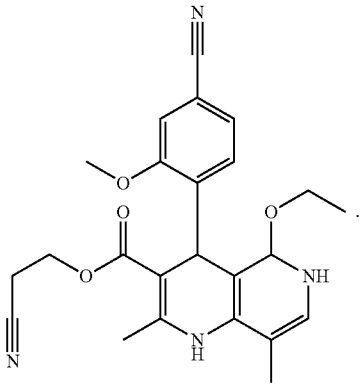

-continued
(XI)
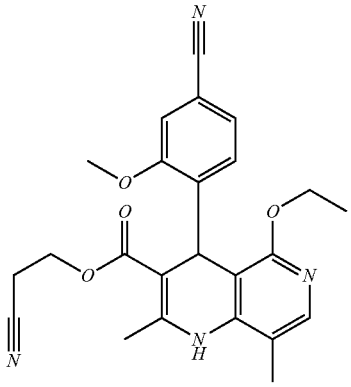
comprising stirring a compound of formula (X)
(X)
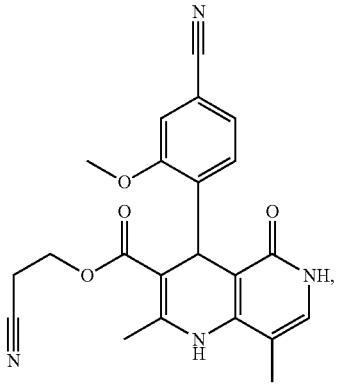
with 2.5-5 equivalents of triethyl orthoacetate in dimethylacetamide at 100 to 120° C. for 1.5 to 3 hours to give the compound of formula (XI)
(XI)
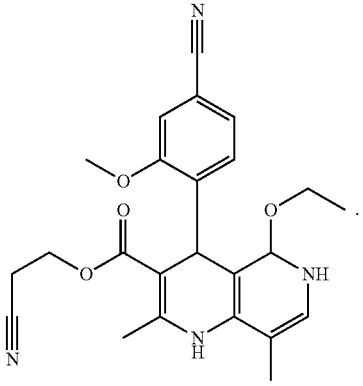
-continued
(XI)
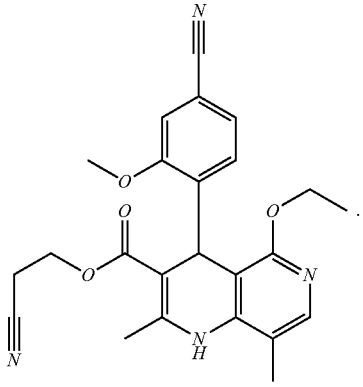
4. A process for preparing a compound of formula (XII)
(XII)
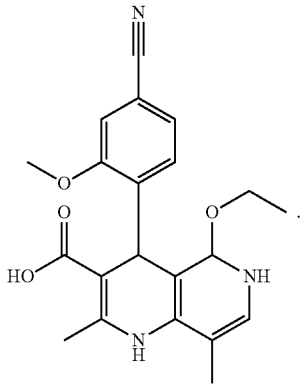
(XII)
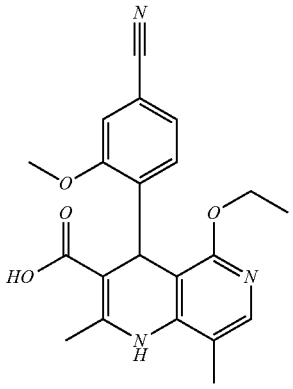

comprising saponifying a compound of formula (XI)
[ (XI)
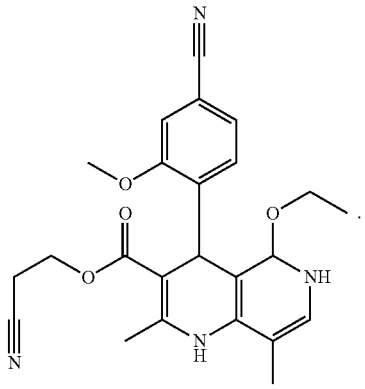
] (XI)
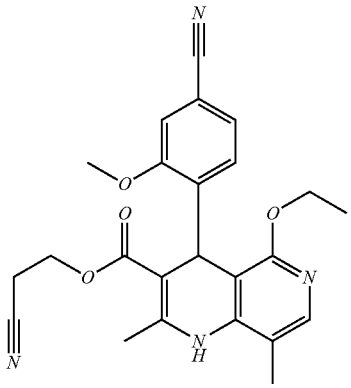
in a THF/water mixture [(2:1, 9-fold)] *2:1, 9-fold,* with aqueous sodium hydroxide solution to give the compound of formula (XII)
[ (XII)
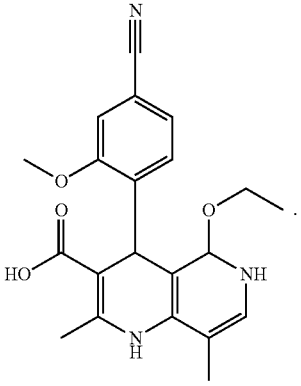
] (XII)
-continued
(XII)
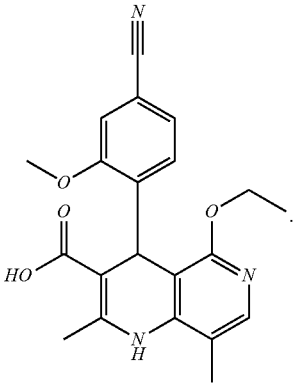
5. A process for preparing a compound of formula (XIII)
(XIII)
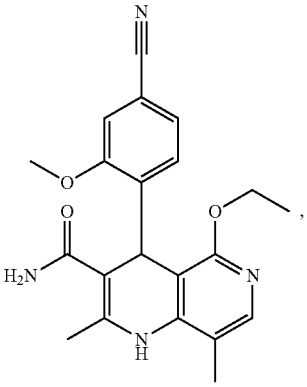
comprising reacting a compound of formula (XII)
[ (XII)
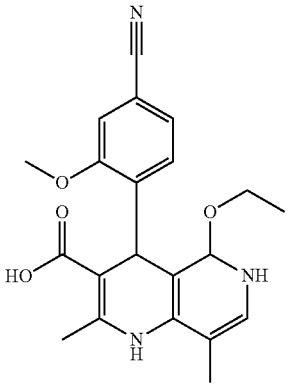
]

-continued (XII)

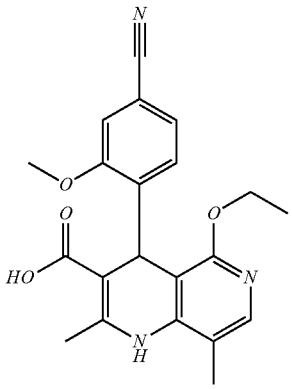

in a one-pot reaction in THF by first admixing with carbodiimidazole and catalytic amounts of 4-(dimethylamino)pyridine to form an admixture, heating the admixture under reflux together with hexamethyldisilazane for 16 to 24 hours and then in a third step hydrolysing in water with THF or water to give the compound of formula (XIII)

(XIII)

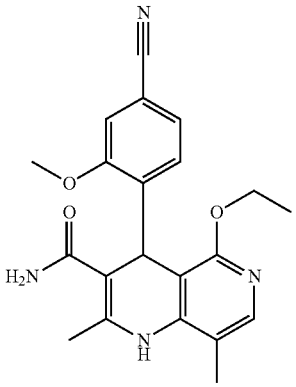

6. A process for preparing compounds of formulae (VIII a+b):

(VIII a+b)

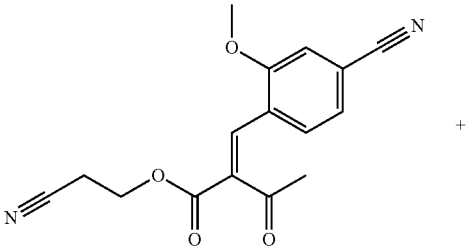

-continued

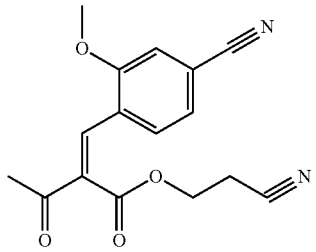

comprising preparing the compound of formula (VI)

(VI)

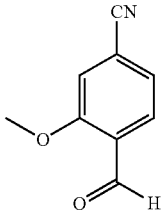

according to the process of claim 1, dissolving the compound of formula (VI) in isopropanol [(3-7 fold)], *3-7 fold*, 5-10 mol % of piperidine and 5-10 mol % of glacial acetic acid at 30° C. and reacting the dissolved compound of formula (VI) with a compound of formula (VII)

(VII)

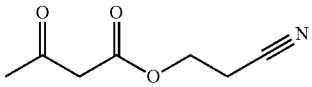

to give the compounds of formulae (VIII a+b):

(VIII a+b)

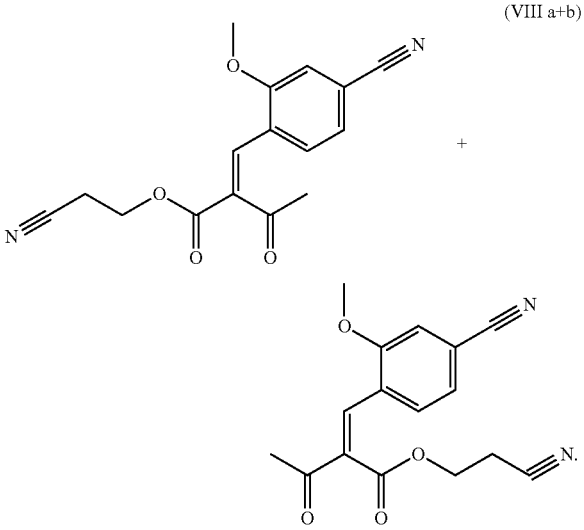

7. A process for preparing a compound of formula (XI)

(XI)

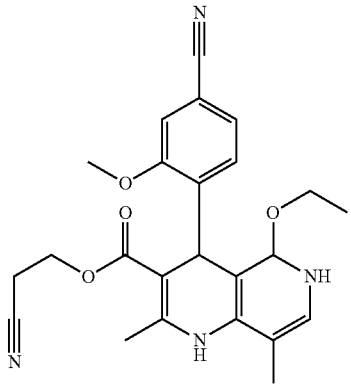

comprising preparing the compounds of formulae (VIII a+b) according to claim 2, reacting the compounds of formulae (VIII a+b) with a compound of formula (IX)

(IX)

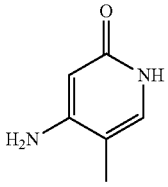

to give a compound of formula (X)

(X)

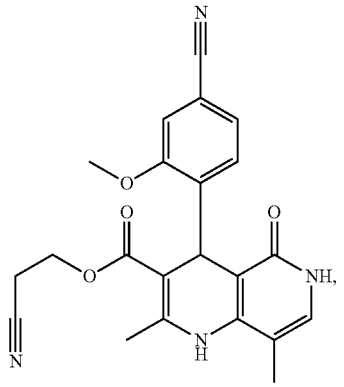

stirring the compound of formula (X) with 2.5-5 eq of triethyl orthoacetate in dimethylacetamide at 100 to 120° C. for 1.5 to 3 hours to give the compound of the formula (XI)

(XI)

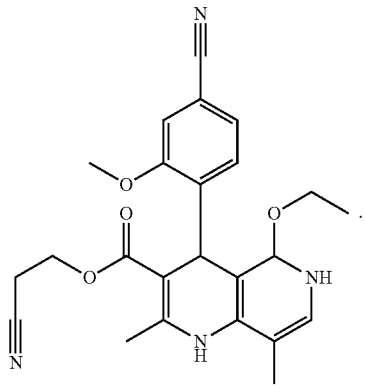

(XI)

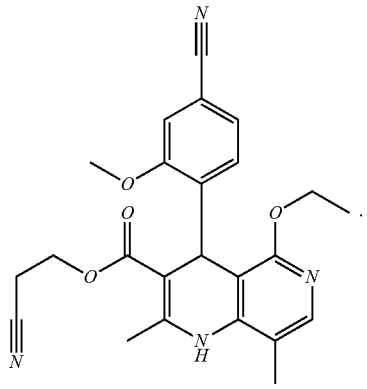

8. A process for preparing a compound of formula (XII)

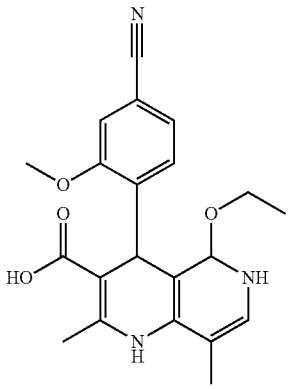

(XII)

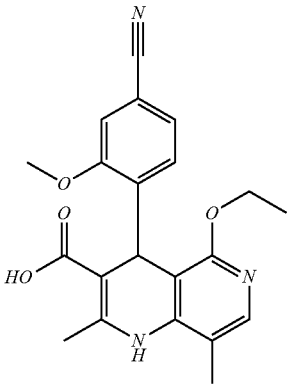

(XII)

comprising preparing the compound of formula (XI) according to claim 3, saponifying the compound of formula (XI) in a THF/water mixture [(2:1, 9-fold)] *2:1, 9-fold,* with aqueous sodium hydroxide solution to give the compound of formula (XII)

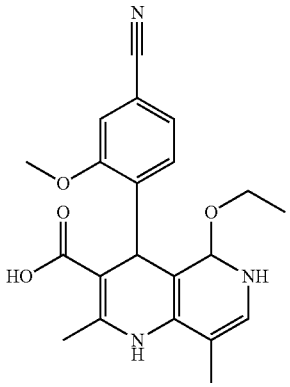

(XII)

-continued

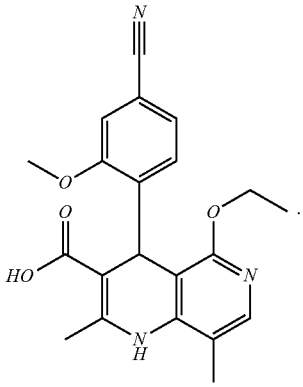

(XII)

9. A process for preparing a compound of formula (XIII)

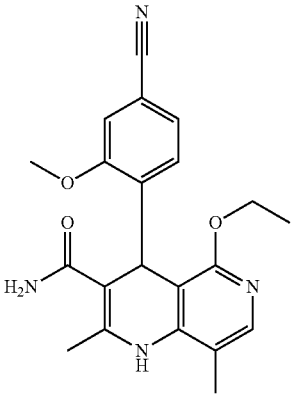

(XIII)

comprising preparing the compound of formula (XII)

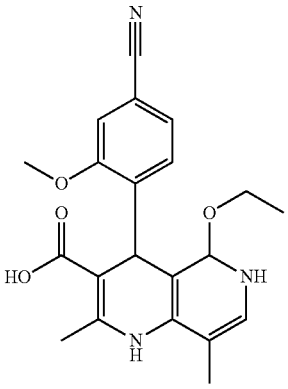

(XII)

-continued (XII)

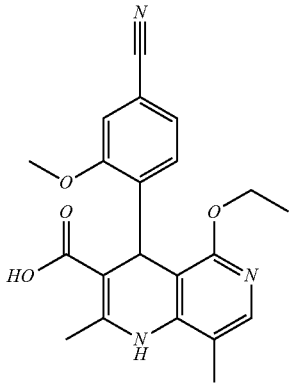

according to the process of claim 4, reacting the compound of formula (XII) in a one-pot reaction in THF by first admixing with carbodiimidazole and catalytic amounts of 4-(dimethylamino)pyridine to form an admixture, heating the admixture under reflux together with hexamethyldisilazane for 16 to 24 hours and then in a third step hydrolysing in water with THF or water to give the compound of formula (XIII)

(XIII)

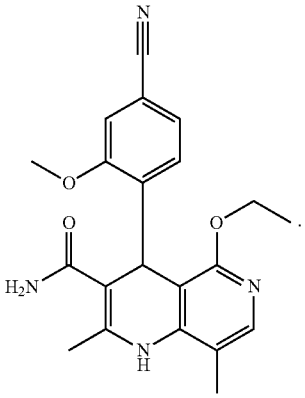

10. A process for preparing a compound of formula (XI)

(XI)

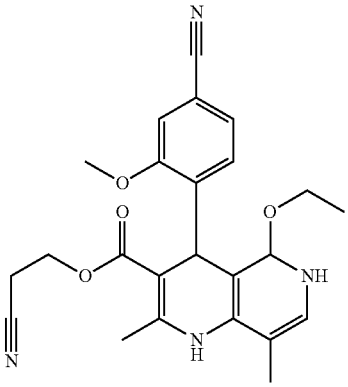

-continued (XI)

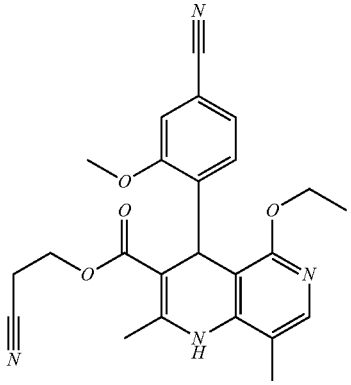

comprising preparing compounds of formulae (VIII a+b)

(VIII a+b)

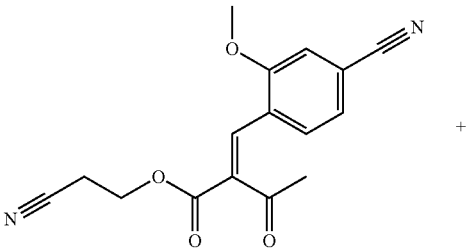

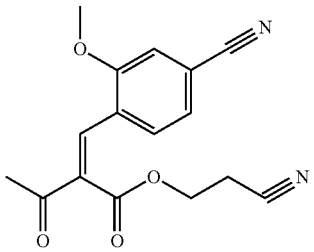

according to the process of claim 6 reacting the compounds of formulae (VIII a+b) with a compound of formula (IX)

(IX)

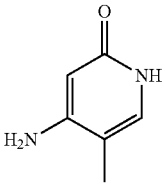

to give a compound of formula (X)

(X)

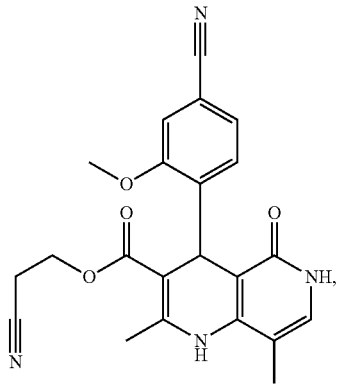

stirring the compound of formula (X) with 2.5-5 eq of triethyl orthoacetate in dimethylacetamide at 100 to 120° C. for 1.5 to 3 hours to give a compound of formula (XI)

[ (XI)

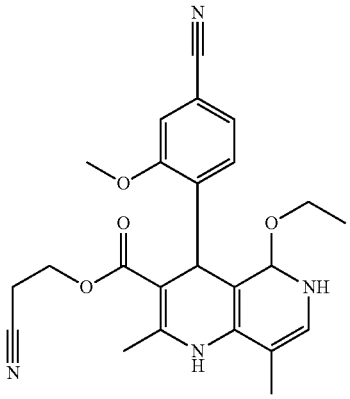

]

*(XI)*

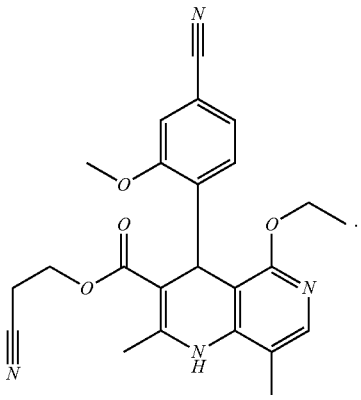

11. A process for preparing the compound of formula (XII)

[ (XII)

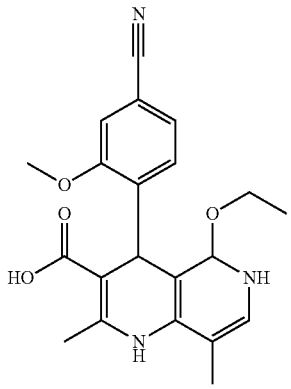

]

*(XII)*

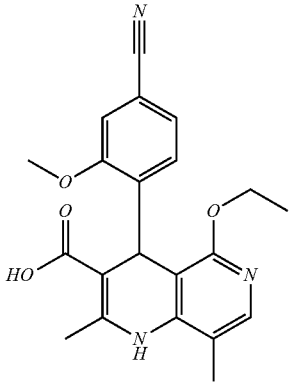

comprising preparing the compound of formula (XI) according to claim 7, and saponifying the compound of formula (XI) in a THF/water mixture [(2:1, 9-fold)] *2:1, 9-fold,* with aqueous sodium hydroxide solution to give the compound of formula (XII)

[ (XII)

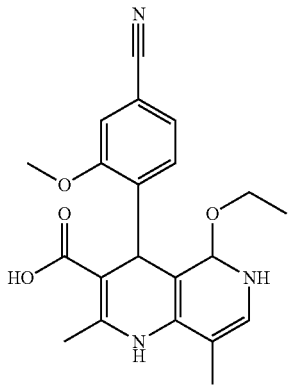

]

-continued (XII)

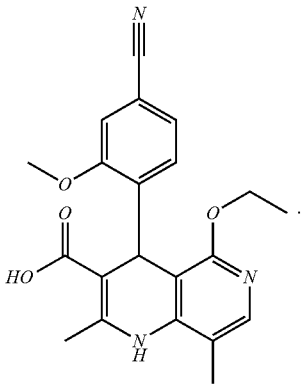

12. A process for preparing a compound of formula (XIII)

(XIII)

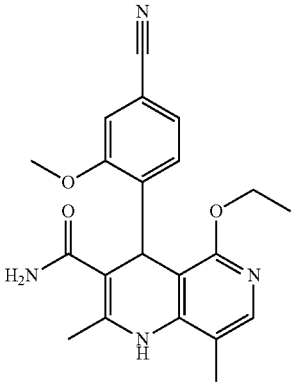

comprising preparing the compound of formula (XII)

(XII)

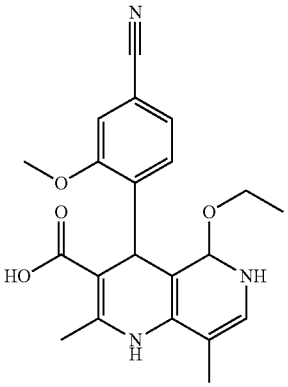

-continued (XII)

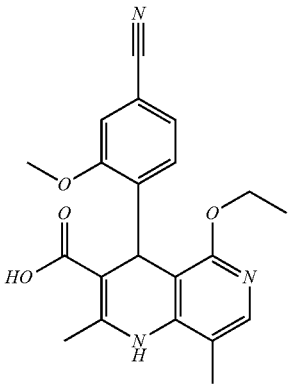

according to the process of claim 8, reacting the compound of formula (XII) in a one-pot reaction in THF by first admixing with carbodiimidazole and catalytic amounts of 4-(dimethylamino)pyridine to form an admixture, heating the admixture under reflux together with hexamethyldisilazane for 16 to 24 hours and then in a third step hydrolysing in water with THF or water to give the compound of formula (XIII)

(XIII)

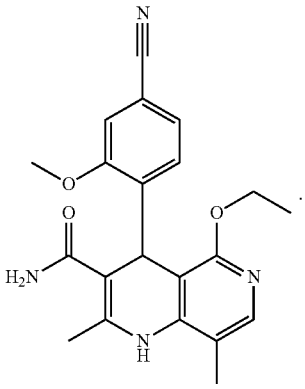

13. A process for preparing a compound of formula (XII)

(XII)

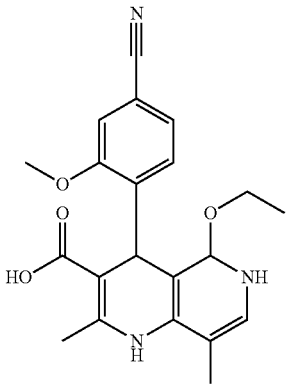

-continued
(XII)
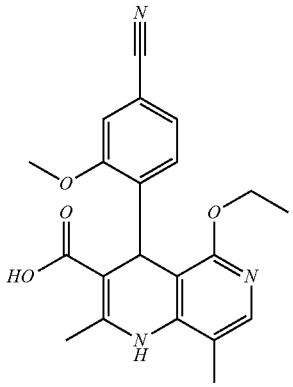
comprising preparing the compound of formula (XI)
[ (XI)
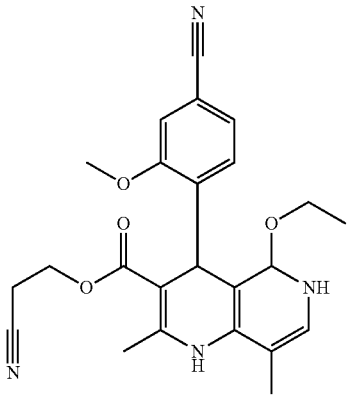
]
(XI)
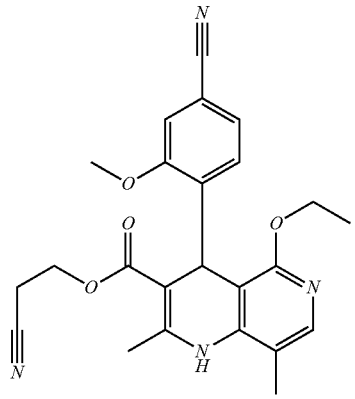
according to the process of claim 10, saponifying the compound of formula (XI) in a THF/water mixture [(2:1, 9-fold)] *2:1, 9-fold,* with aqueous sodium hydroxide solution to give a compound of formula (XII)
[ (XII)
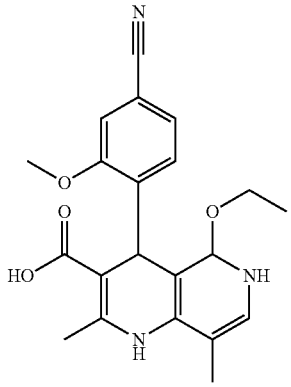
]
(XII)
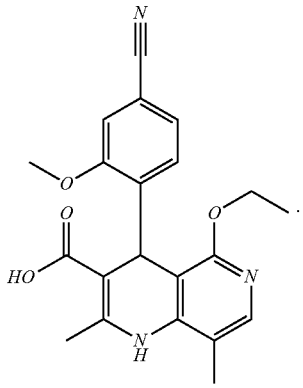
14. A process for preparing a compound of formula (XIII)
(XIII)
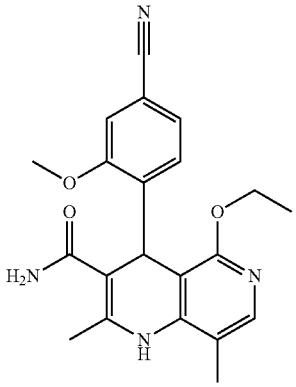

comprising preparing the compound of formula (XII)

(XII)

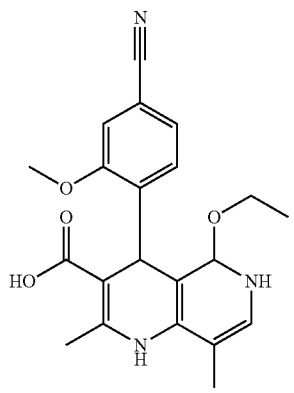

(XII)

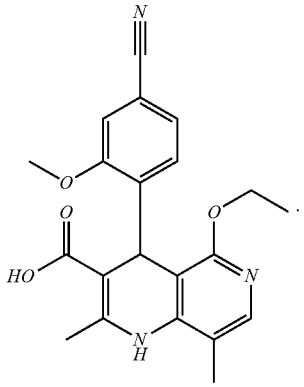

according to the process of claim 11, reacting the compound of formula (XII) in a one-pot reaction in THF by first admixing with carbodiimidazole and catalytic amounts of 4-(dimethylamino)pyridine to form an admixture, heating the admixture under reflux together with hexamethyldisilazane for 16 to 24 hours and then in a third step hydrolysing in water with THF or water to give the compound of formula (XIII)

(XIII)

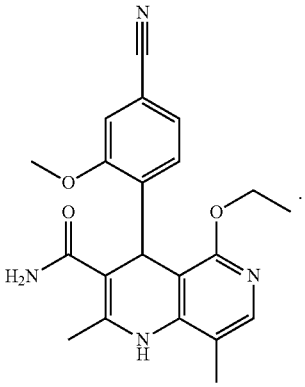

15. A process for preparing a compound of formula (XIII)

(XIII)

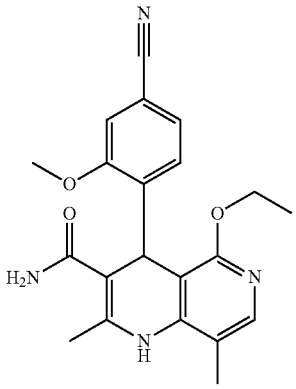

comprising preparing the compound of formula (XII)

(XII)

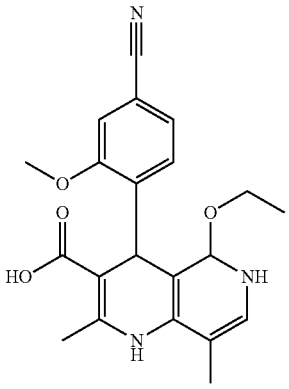

(XII)

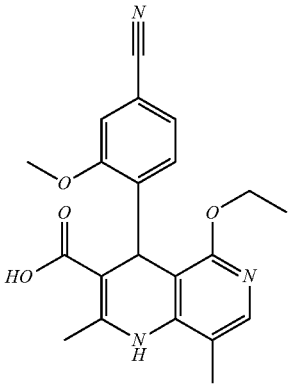

according to the process of claim 13, reacting the compound of formula (XII) in a one-pot reaction in THF by first admixing with carbodiimidazole and catalytic amounts of 4-(dimethylamino)pyridine to form an admixture, heating the admixture under reflux together with hexamethyldisilazane for 16 to 24 hours and then in a third step hydrolysing in water with THF or water to give the compound of formula (XIII)

(XIII)

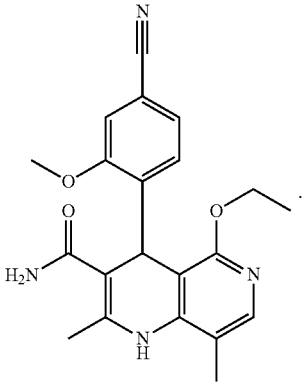

16. A process for preparing a compound of formula (I)

(I)

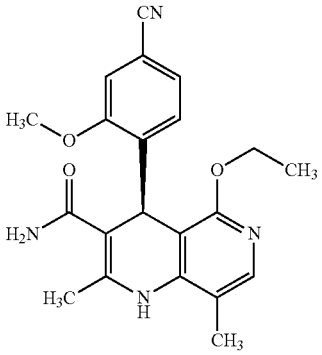

comprising preparing the compound of formula (XIII) in a mixture of enantiomers according to the process of claim 5 and isolating the compound of formula (I) from the mixture.

17. A process for preparing a compound of formula (I)

(I)

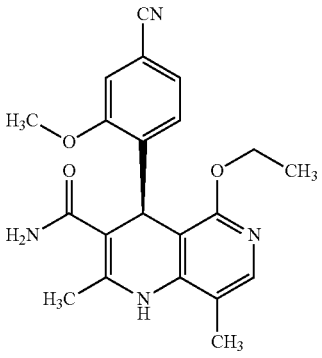

comprising preparing the compound of formula (XIII) in a mixture of enantiomers according to the process of claim 9 and isolating the compound of formula (I) from the mixture.

18. A process for preparing a compound of formula (I)

(I)

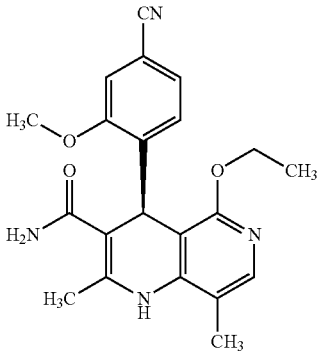

comprising preparing the compound of formula (XIII) in a mixture of enantiomers according to the process of claim 12 and isolating the compound of formula (I) from the mixture.

19. A process for preparing a compound of formula (I)

(I)

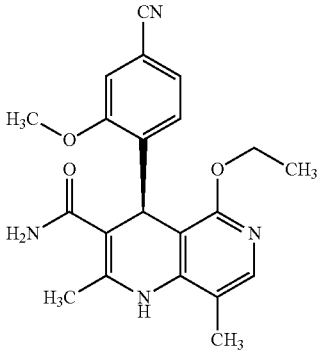

comprising preparing the compound of formula (XIII) in a mixture of enantiomers according to the process of claim 14 and isolating the compound of formula (I) from the mixture.

20. A process for preparing a compound of formula (I)

(I)

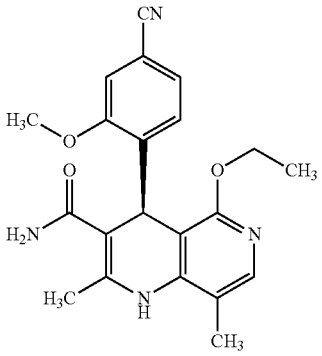

comprising preparing the compound of formula (XIII) in a mixture of enantiomers according to the process of claim 15 and isolating the compound of formula (I) from the mixture.

21. The process of claim 17, wherein the isolated compound of the formula (I) is present in one or more polymorphs or as a solvate in an inert solvent, further comprising stirring the inert solvent containing the isolated compound of formula (I) at a temperature of 20° C.-120° C. and isolating the compound of the formula (I) as crystalline polymorph I.

22. The process of claim 18, wherein the isolated compound of the formula (I) is present in one or more polymorphs or as a solvate in an inert solvent, further comprising stirring the inert solvent containing the isolated compound of formula (I) at a temperature of 20° C.-120° C. and isolating the compound of the formula (I) as crystalline polymorph I.

23. The process of claim 19, wherein the isolated compound of the formula (I) is present in one or more polymorphs or as a solvate in an inert solvent, further comprising stirring the inert solvent containing the isolated compound of formula (I) at a temperature of 20° C.-120° C. and isolating the compound of the formula (I) as crystalline polymorph I.

24. The process of claim 20, wherein the isolated compound of the formula (I) is present in one or more polymorphs or as a solvate in an inert solvent, further comprising stirring the inert solvent containing the isolated compound of formula (I) at a temperature of 20° C.-120° C. and isolating the compound of the formula (I) as crystalline polymorph I.

* * * * *